US012349891B2

(12) United States Patent
Garcia-Bengochea

(10) Patent No.: US 12,349,891 B2
(45) Date of Patent: Jul. 8, 2025

(54) APPARATUS FOR POSITIONING A PATIENT DURING SURGERY TO MAXIMIZE ACCESS TO A SURGICAL SITE OF INTEREST

(71) Applicant: JGMG BENGOCHEA, LLC, Jacksonville, FL (US)

(72) Inventor: Javier Garcia-Bengochea, Jacksonville, FL (US)

(73) Assignee: JGMG BENGOCHEA, LLC, Jacksonville, FL (US)

( * ) Notice: Subject to any disclaimer, the term of this patent is extended or adjusted under 35 U.S.C. 154(b) by 0 days.

(21) Appl. No.: 18/670,077

(22) Filed: May 21, 2024

(65) Prior Publication Data
US 2024/0307048 A1 Sep. 19, 2024

Related U.S. Application Data

(60) Continuation of application No. 18/345,719, filed on Jun. 30, 2023, now Pat. No. 12,070,202, which is a
(Continued)

(51) Int. Cl.
*A61B 17/02* (2006.01)
*A61B 17/00* (2006.01)
(Continued)

(52) U.S. Cl.
CPC ............ *A61B 17/025* (2013.01); *A61B 17/02* (2013.01); *A61B 17/0206* (2013.01);
(Continued)

(58) Field of Classification Search
CPC .............. A61G 13/1285; A61G 13/129; A61G 13/1295; A61G 13/123; A61G 13/0054; A61G 7/109; A61F 5/042; A61H 1/0218
See application file for complete search history.

(56) References Cited

U.S. PATENT DOCUMENTS 2,565,019 A * 8/1951 Buchanan ............ A61H 1/0222
606/237
3,420,229 A * 1/1969 Miller .................. A61H 1/0222
606/243
(Continued)

FOREIGN PATENT DOCUMENTS

RU 2288650 12/2006

OTHER PUBLICATIONS

Kamran Aghayev, Frank D. Vrionis, Mini-open lateral retroperitoneal lumbar spine approach using psoas muscle retraction technique. Technical report and initial results on six patients. Eur Spine J (2013), Ideas and Technical Innovations, Aug. 1, 2013, 22:2113-2119. Springer-Verlag Berlin Heidelberg 2013.
(Continued)

*Primary Examiner* — Justin C Mikowski
*Assistant Examiner* — Alison N Labarge
(74) *Attorney, Agent, or Firm* — McNees Wallace & Nurick LLC

(57) ABSTRACT

An apparatus for positioning a patient during surgery includes a surgical table frame having a longitudinal dimension, two or more longitudinal rails that are laterally spaced from a centerline between the longitudinal rails and defining a generally planar surface of the surgical table frame, and at least one rotatable support mounted on the surgical table frame for supporting a portion of a body of the patient when resting thereon the at least one rotatable support having a support surface that is substantially planar and generally parallel to the generally planar surface of the surgical table frame. The at least one rotatable support enables positional adjustment of the portion of the body of the patient when resting thereon by rotational movement of the at least one rotatable support to displace the supported body position in one of first and second directions of rotation to thereby allow
(Continued)

for manipulation of the patient's anatomy to maximize access to a surgical site of interest.

26 Claims, 58 Drawing Sheets

Related U.S. Application Data continuation of application No. 16/875,507, filed on May 15, 2020, now Pat. No. 11,779,322, which is a division of application No. 16/028,817, filed on Jul. 6, 2018, now abandoned, which is a division of application No. 14/791,881, filed on Jul. 6, 2015, now Pat. No. 10,045,768.

(60) Provisional application No. 62/080,609, filed on Nov. 17, 2014, provisional application No. 62/080,573, filed on Nov. 17, 2014, provisional application No. 62/080,578, filed on Nov. 17, 2014, provisional application No. 62/080,590, filed on Nov. 17, 2014, provisional application No. 62/080,557, filed on Nov. 17, 2014, provisional application No. 62/156,184, filed on May 1, 2015, provisional application No. 62/021,202, filed on Jul. 6, 2014.

(51) Int. Cl.
*A61B 90/00* (2016.01)
*A61F 2/44* (2006.01)
*A61F 2/46* (2006.01)
*A61G 13/12* (2006.01)

(52) U.S. Cl.
CPC ........ *A61B 17/0218* (2013.01); *A61F 2/4455* (2013.01); *A61F 2/4611* (2013.01); *A61F 2/4684* (2013.01); *A61G 13/1285* (2013.01); *A61B 2017/0092* (2013.01); *A61B 2017/0256* (2013.01); *A61B 2090/062* (2016.02); *A61B 2090/3966* (2016.02)

(56) References Cited

U.S. PATENT DOCUMENTS

| | | |
|---|---|---|
| 4,354,485 A | 10/1982 | Safadago |
| 5,020,519 A | 6/1991 | Hayes et al. |
| 5,489,307 A | 2/1996 | Kuslich et al. |
| 5,522,899 A | 6/1996 | Michelson |
| 5,562,736 A | 10/1996 | Ray et al. |
| 5,613,254 A * | 3/1997 | Clayman ............... A61G 13/12 5/613 |
| 5,772,583 A | 6/1998 | Wright et al. |
| 5,792,044 A | 8/1998 | Foley et al. |
| 5,795,291 A | 8/1998 | Koros et al. |
| 5,799,055 A | 8/1998 | Peshkin et al. |
| 5,888,197 A | 3/1999 | Mulac et al. |
| 5,902,233 A | 5/1999 | Farley et al. |
| 5,928,139 A | 7/1999 | Koros et al. |
| 5,944,658 A | 8/1999 | Koros et al. |
| 5,976,146 A | 11/1999 | Ogawa et al. |
| 5,980,504 A | 11/1999 | Sharkey et al. |
| 6,017,008 A | 1/2000 | Farley |
| 6,159,215 A | 12/2000 | Urbahns et al. |
| 6,187,000 B1 | 2/2001 | Davison et al. |
| 6,224,595 B1 | 5/2001 | Michelson |
| 6,224,607 B1 | 5/2001 | Michelson |
| 6,235,028 B1 | 5/2001 | Brumfield et al. |
| 6,287,313 B1 | 9/2001 | Sasso |
| 6,319,257 B1 | 11/2001 | Carignan et al. |
| 6,371,968 B1 | 4/2002 | Kogasaka et al. |
| 6,419,678 B1 | 7/2002 | Asfora |
| 6,428,497 B1 | 8/2002 | Crouch |
| 6,436,098 B1 | 8/2002 | Michelson |
| 6,447,512 B1 | 9/2002 | Landry et al. |
| 6,500,180 B1 | 12/2002 | Foley et al. |
| 6,511,423 B2 | 1/2003 | Farley |
| 6,520,907 B1 | 2/2003 | Foley et al. |
| 6,524,312 B2 | 2/2003 | Landry et al. |
| 6,524,318 B1 | 2/2003 | Longhini et al. |
| 6,524,320 B2 | 2/2003 | DiPoto |
| 6,530,926 B1 | 3/2003 | Davison |
| 6,530,929 B1 | 3/2003 | Justis et al. |
| 6,554,836 B2 | 4/2003 | Michelson |
| 6,558,390 B2 | 5/2003 | Cragg |
| 6,575,979 B1 | 6/2003 | Cragg |
| 6,595,998 B2 | 7/2003 | Johnson et al. |
| 6,638,299 B2 | 10/2003 | Cox |
| 6,663,637 B2 | 12/2003 | Dixon et al. |
| 6,733,496 B2 | 5/2004 | Sharkey et al. |
| 6,783,528 B2 | 8/2004 | Vincent-Prestigiacomo |
| 6,849,064 B2 | 2/2005 | Hamada |
| 6,851,430 B2 | 2/2005 | Tsou |
| 6,855,148 B2 | 2/2005 | Foley et al. |
| 6,896,680 B2 | 5/2005 | Michelson |
| 6,997,929 B2 | 2/2006 | Manzi et al. |
| 7,004,945 B2 | 2/2006 | Boyd et al. |
| 7,008,431 B2 | 3/2006 | Simonson |
| 7,118,579 B2 | 10/2006 | Michelson |
| 7,179,225 B2 | 2/2007 | Shluzas et al. |
| 7,207,991 B2 | 4/2007 | Michelson |
| 7,226,451 B2 | 6/2007 | Shluzas et al. |
| 7,232,411 B2 | 6/2007 | Dinkler, II et al. |
| 7,291,149 B1 | 11/2007 | Michelson |
| 7,326,203 B2 | 2/2008 | Papineau et al. |
| 7,416,553 B2 | 8/2008 | Patel et al. |
| 7,491,168 B2 | 2/2009 | Raymond et al. |
| 7,691,120 B2 | 4/2010 | Shluzas et al. |
| 7,713,281 B2 | 5/2010 | Leeflang et al. |
| 7,766,930 B2 | 8/2010 | DiPoto et al. |
| 7,776,047 B2 | 8/2010 | Fanger et al. |
| 7,799,033 B2 | 9/2010 | Assell et al. |
| 7,875,049 B2 | 1/2011 | Eversull et al. |
| 7,909,829 B2 | 3/2011 | Patel et al. |
| 7,909,848 B2 | 3/2011 | Patel et al. |
| 7,951,153 B2 | 5/2011 | Abdou |
| 7,981,029 B2 | 7/2011 | Branch et al. |
| 7,993,350 B2 | 8/2011 | Ventura et al. |
| 8,066,714 B2 | 11/2011 | Shipp et al. |
| 8,100,828 B2 | 1/2012 | Frey et al. |
| 8,114,088 B2 | 2/2012 | Miller |
| 8,152,714 B2 | 4/2012 | Garcia-Bengochea et al. |
| 8,206,292 B2 | 6/2012 | Eckman |
| 8,206,449 B2 | 6/2012 | Jansen et al. |
| 8,235,999 B2 | 8/2012 | Simonson |
| 8,277,486 B2 | 10/2012 | Davison |
| 8,292,896 B2 | 10/2012 | Abdou |
| 8,303,601 B2 | 11/2012 | Bandeira et al. |
| 8,343,163 B1 | 1/2013 | Arambula et al. |
| 8,357,184 B2 | 1/2013 | Woolley et al. |
| 8,361,151 B2 | 1/2013 | Simonson |
| 8,425,602 B2 | 4/2013 | Guyer et al. |
| 8,425,610 B2 | 4/2013 | Guyer et al. |
| 8,444,678 B2 | 5/2013 | Simonson et al. |
| 8,449,463 B2 | 5/2013 | Nunley et al. |
| 8,450,288 B2 | 5/2013 | Boyd |
| 8,568,306 B2 | 10/2013 | Hardenbrook |
| 8,673,013 B2 | 3/2014 | Abdou |
| 8,728,162 B2 | 5/2014 | Akyuz et al. |
| 8,808,305 B2 | 8/2014 | Kleiner |
| 8,840,622 B1 | 9/2014 | Vellido et al. |
| 8,864,770 B2 | 10/2014 | Blain et al. |
| 8,876,904 B2 | 11/2014 | Pimenta et al. |
| 8,882,661 B2 | 11/2014 | Hutton et al. |
| 8,911,364 B2 | 12/2014 | Feigenwinter et al. |
| 8,945,003 B2 | 2/2015 | Bass et al. |
| 2003/0178027 A1 | 9/2003 | DeMayo |
| 2003/0199885 A1 | 10/2003 | Davison et al. |
| 2005/0165405 A1 | 7/2005 | Tsou |
| 2005/0081865 A1 | 9/2005 | Hubert et al. |
| 2005/0197623 A1 | 9/2005 | Leeflang et al. |
| 2006/0089652 A1 | 4/2006 | Eckman |
| 2006/0111728 A1 | 5/2006 | Abdou |

(56) References Cited

U.S. PATENT DOCUMENTS

| | | |
|---|---|---|
| 2006/0229627 A1 | 10/2006 | Hunt et al. |
| 2006/0229636 A1 | 10/2006 | Woodburn et al. |
| 2006/0248650 A1* | 11/2006 | Skripps ............... A61G 13/0054 5/624 |
| 2006/0264960 A1 | 11/2006 | Kuslich et al. |
| 2006/0293678 A1 | 12/2006 | Davison et al. |
| 2007/0123402 A1* | 5/2007 | Cantrell ............... A61H 1/0218 482/148 |
| 2007/0213739 A1 | 9/2007 | Michelson |
| 2007/0260270 A1 | 11/2007 | Assell et al. |
| 2007/0270866 A1 | 11/2007 | von Jako |
| 2007/0293796 A1* | 12/2007 | Graham ............... A61H 1/0292 602/19 |
| 2008/0108940 A1 | 5/2008 | Sharkey et al. |
| 2008/0221586 A1 | 9/2008 | Garcia-Bengochea et al. |
| 2009/0234399 A1 | 9/2009 | Cragg |
| 2009/0247917 A1 | 10/2009 | Park |
| 2009/0264941 A1 | 10/2009 | Banouskou |
| 2010/0076502 A1 | 3/2010 | Guyer et al. |
| 2010/0137922 A1 | 6/2010 | Hunt et al. |
| 2011/0125163 A1 | 5/2011 | Rutten et al. |
| 2011/0166611 A1 | 7/2011 | Stinson |
| 2011/0201897 A1 | 8/2011 | Bertagnoli et al. |
| 2011/0237898 A1 | 9/2011 | Stone et al. |
| 2012/0029635 A1 | 2/2012 | Schoenhoeffer et al. |
| 2012/0071980 A1 | 3/2012 | Purcell et al. |
| 2012/0083887 A1 | 4/2012 | Purcell et al. |
| 2012/0101506 A1 | 4/2012 | Shim et al. |
| 2012/0215229 A1 | 8/2012 | Garcia-Bengochea et al. |
| 2012/0232350 A1 | 9/2012 | Seex |
| 2012/0259343 A1 | 10/2012 | Clark et al. |
| 2012/0265310 A1 | 10/2012 | Fabian |
| 2012/0271120 A1 | 10/2012 | Seex |
| 2013/0225935 A1 | 8/2013 | Nunley et al. |
| 2014/0039267 A1 | 2/2014 | Seex et al. |
| 2014/0100446 A1* | 4/2014 | Lee ............... A61B 6/12 600/424 |
| 2014/0172029 A1 | 6/2014 | Guyer et al. |
| 2014/0194697 A1 | 7/2014 | Seex |
| 2014/0316212 A1 | 10/2014 | Reimels |
| 2014/0371540 A1 | 12/2014 | Hutton et al. |
| 2015/0250466 A1 | 9/2015 | Thornburg |
| 2016/0193098 A1 | 7/2016 | Nichols |

OTHER PUBLICATIONS

Brian Hood, Steven Vanni, Minimally Invasive Extreme Lateral Trans-Psoas Approach to the Lumbar Spine; Applications and Techniques, University of Miami, Miller School of Medicine, Jackson Memorial Hospital, InTechOpen.

PCT International Search Report issued Dec. 25, 2015, PCT/US/2015/039200.

PCT Written Opinion, issued Dec. 10, 2015, PCT/US2015/039200.

* cited by examiner

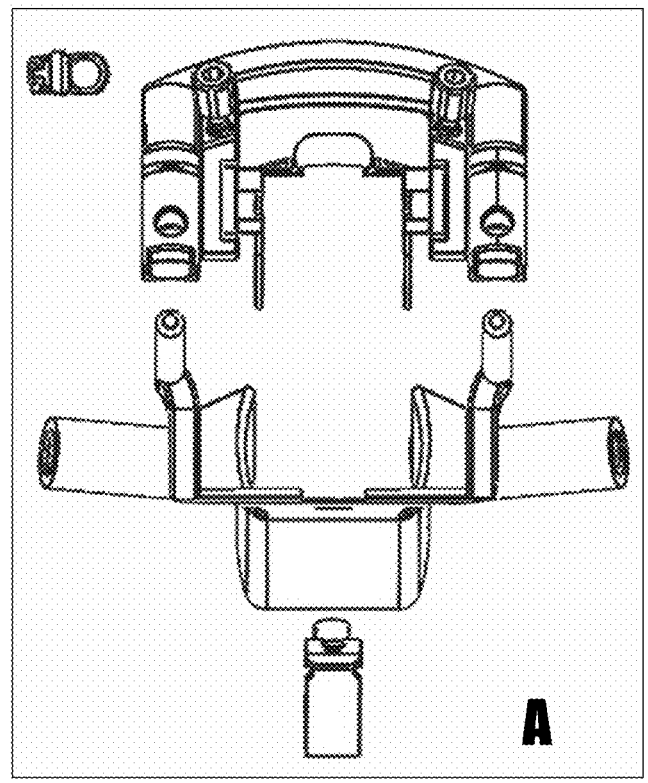
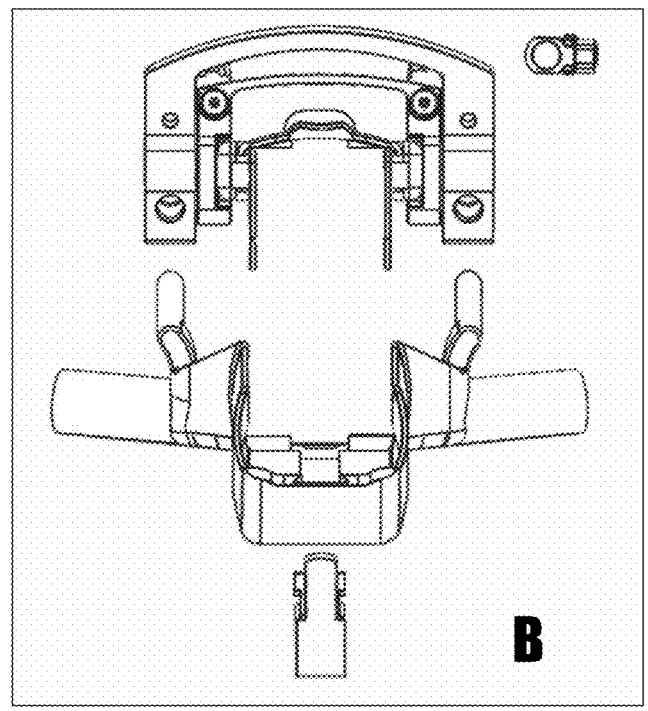
FIG. 7

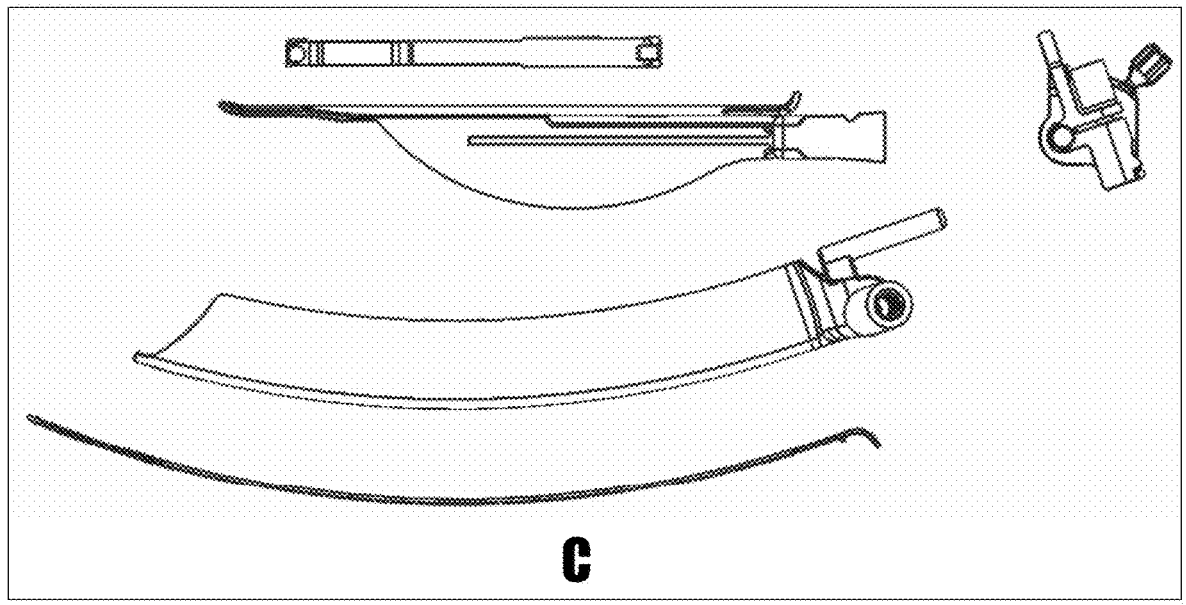
C
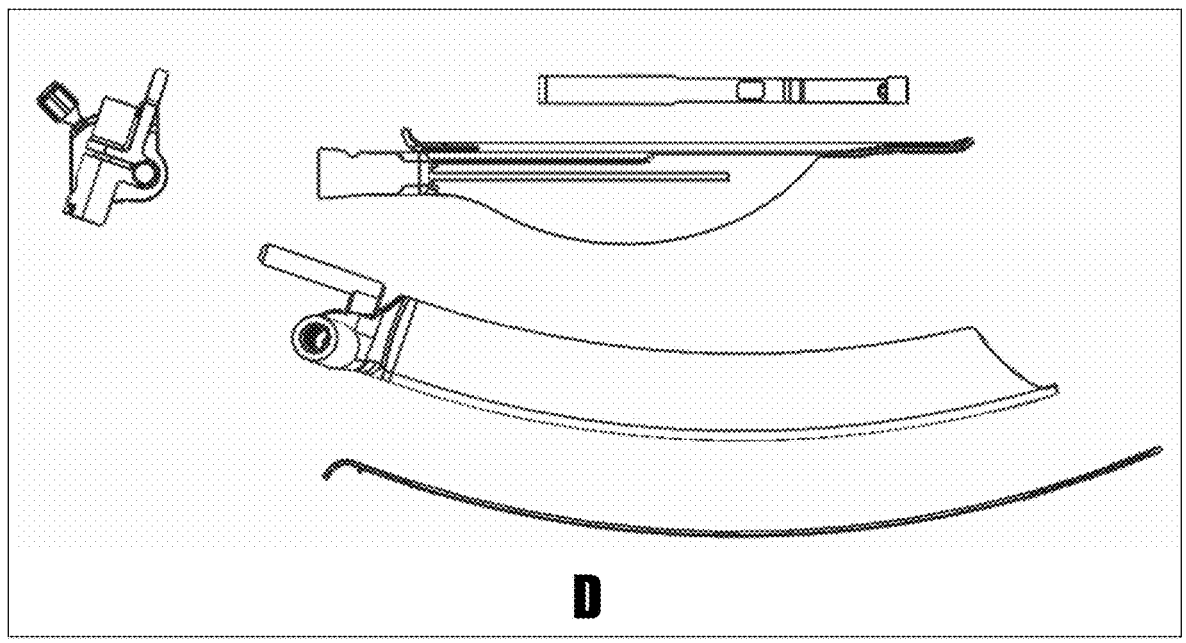
D
FIG. 7 (CONT)

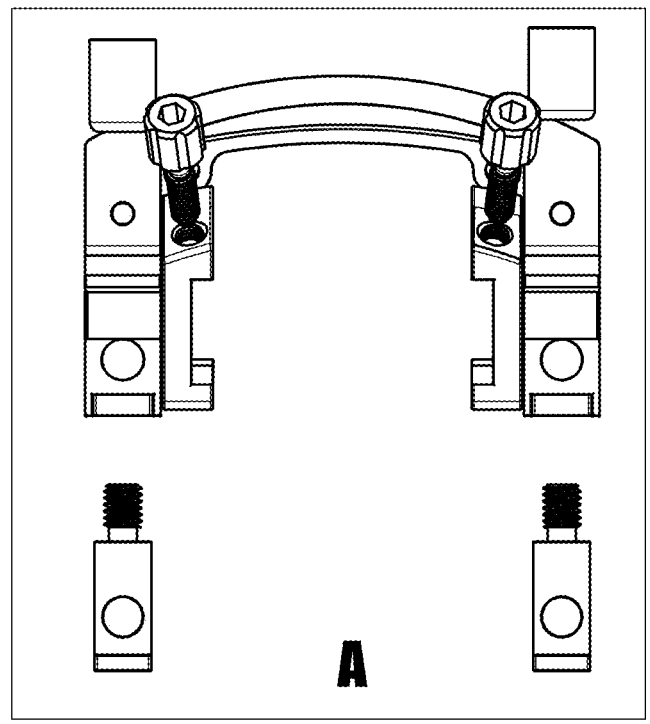
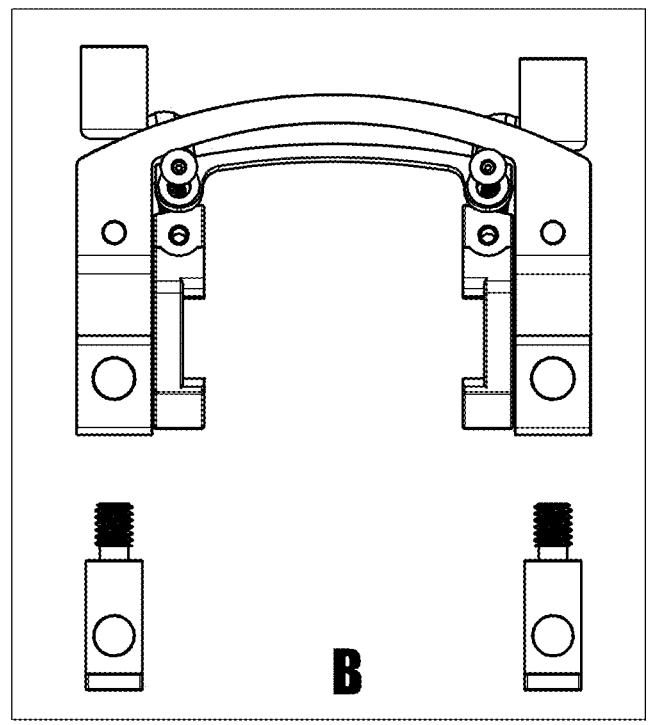
FIG. 8

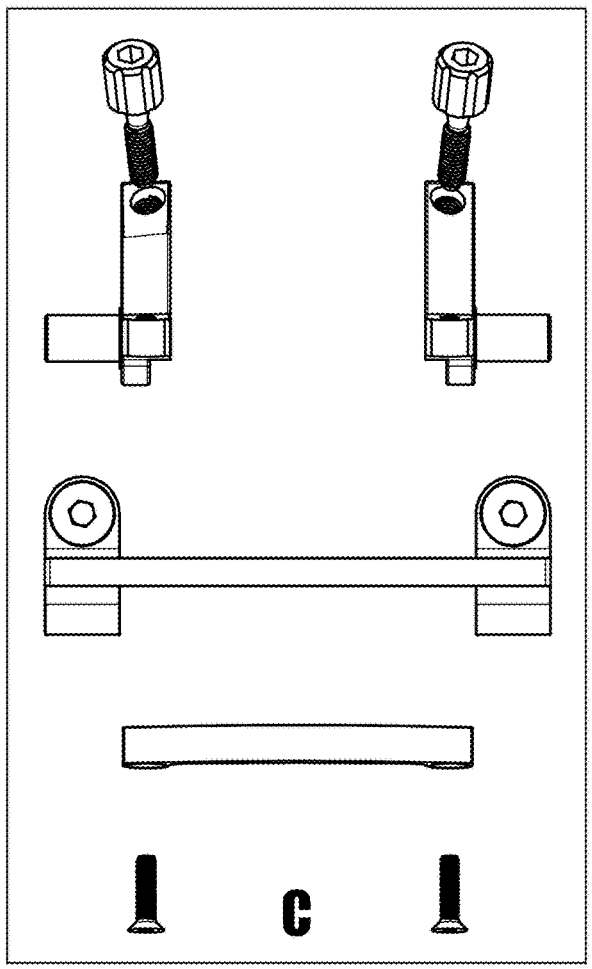
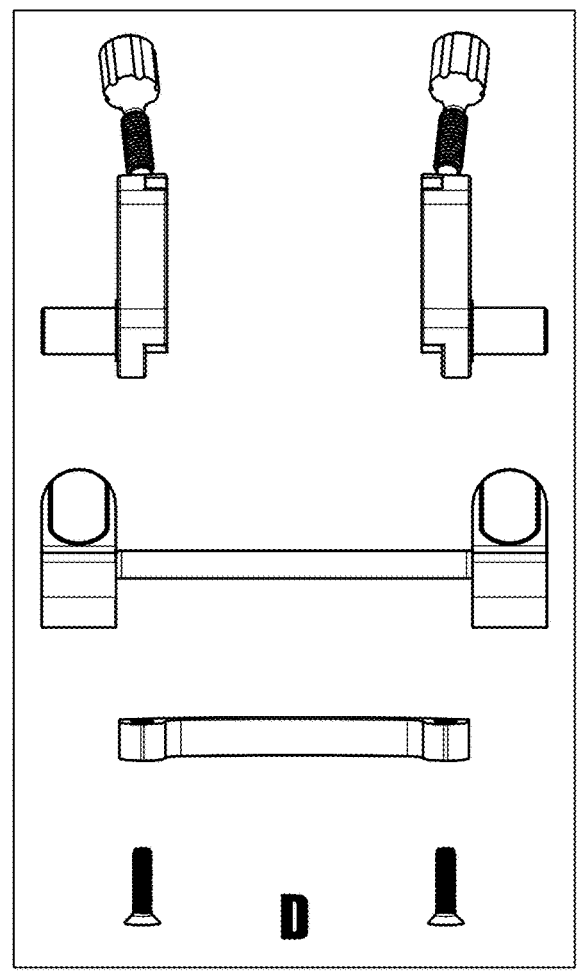
FIG. 8 (CONT)

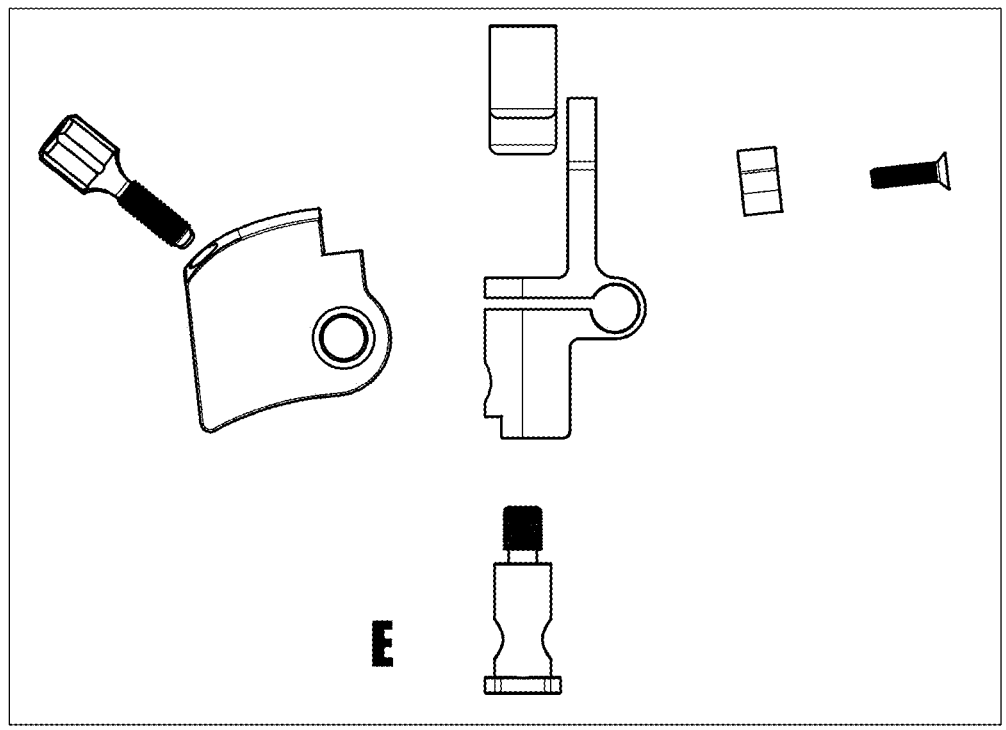
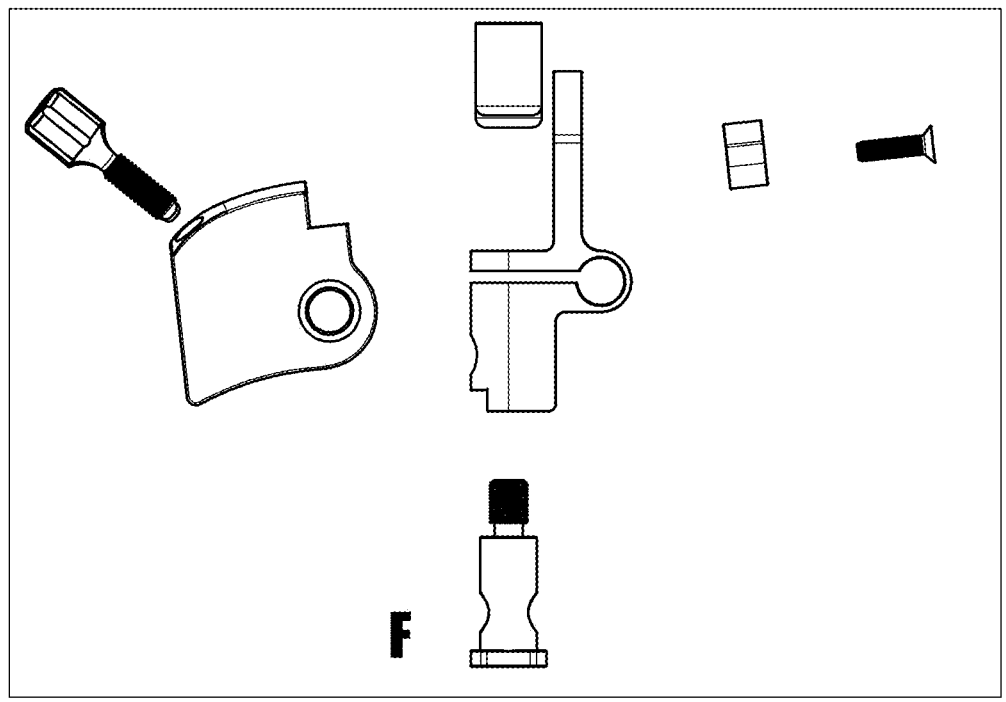
FIG. 8 (CONT)

G

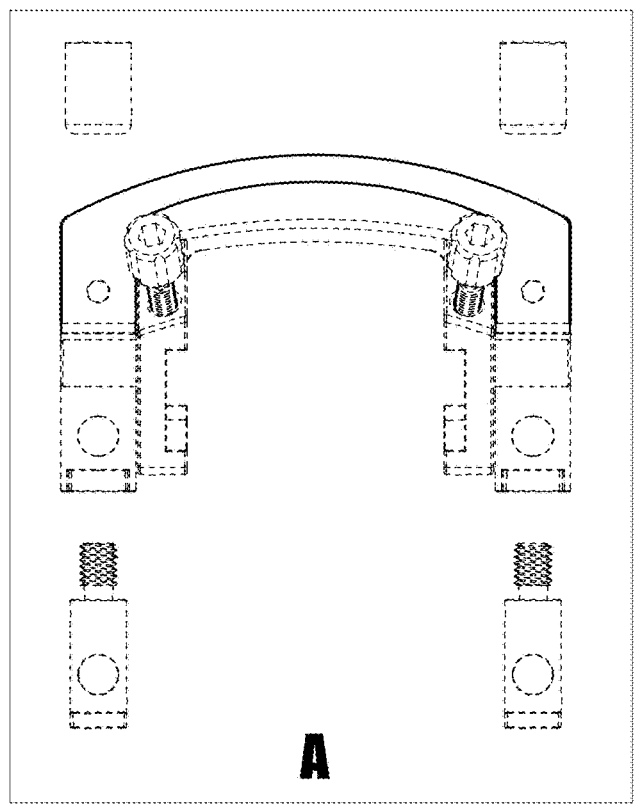
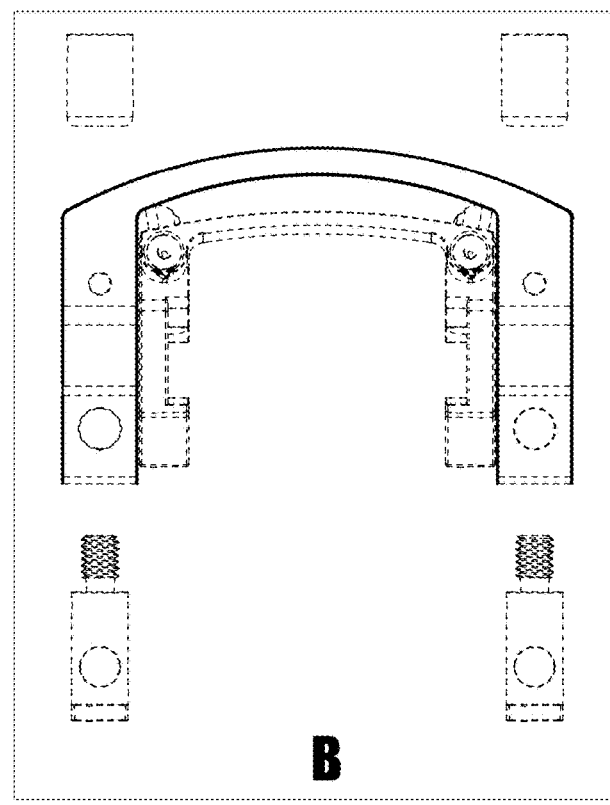
FIG. 11

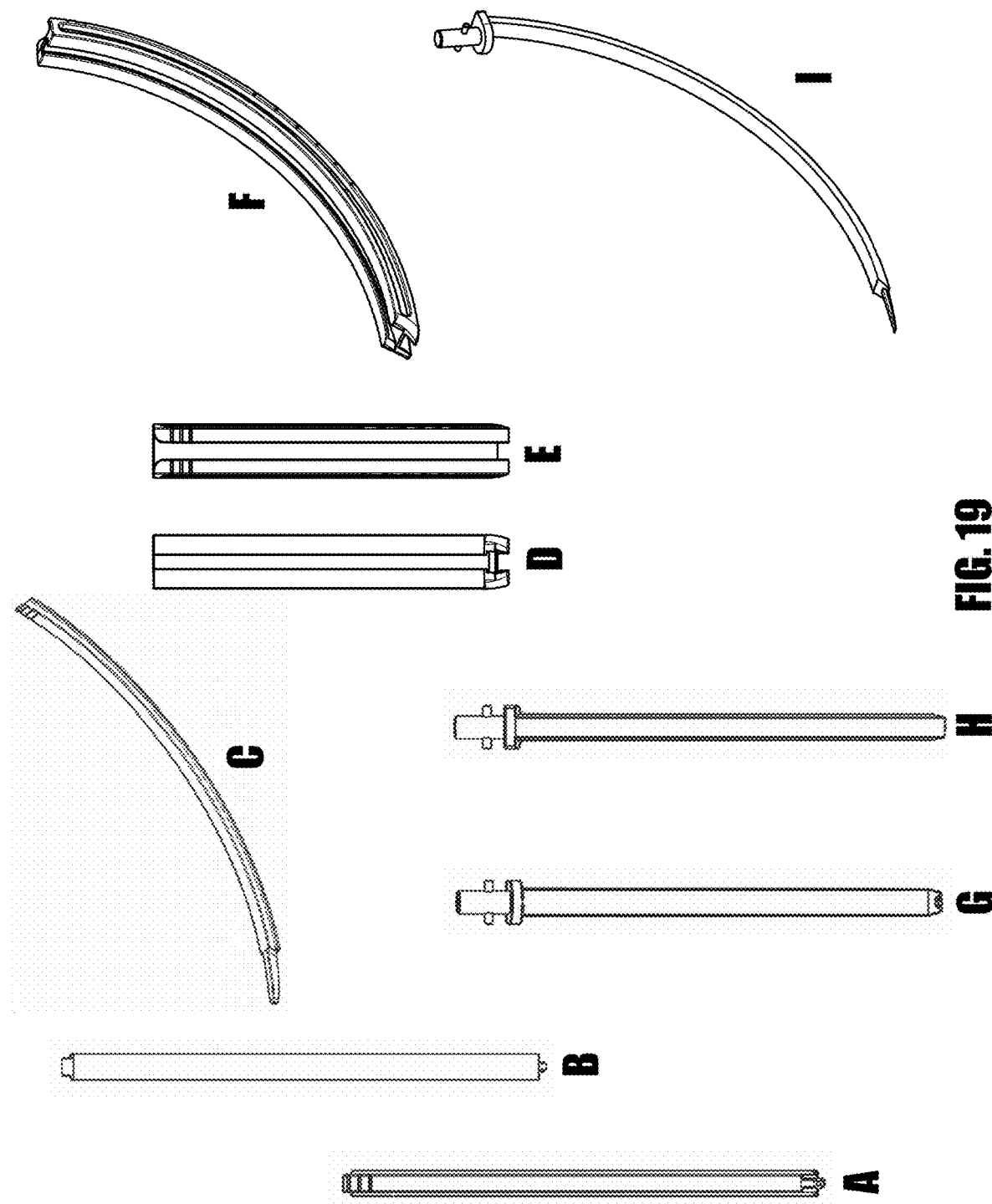

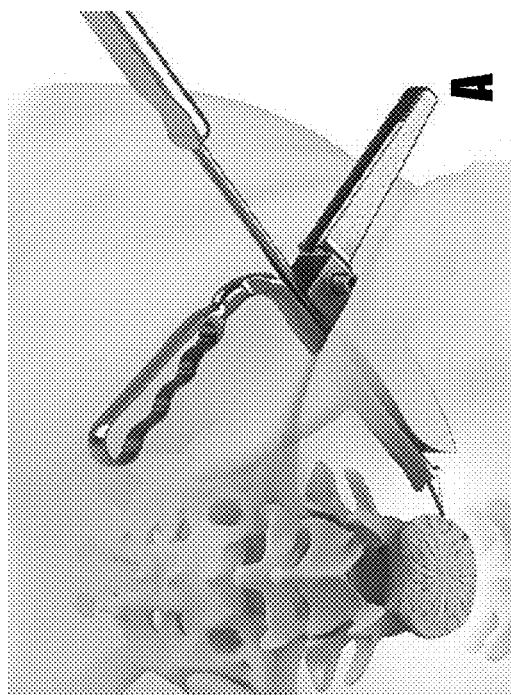
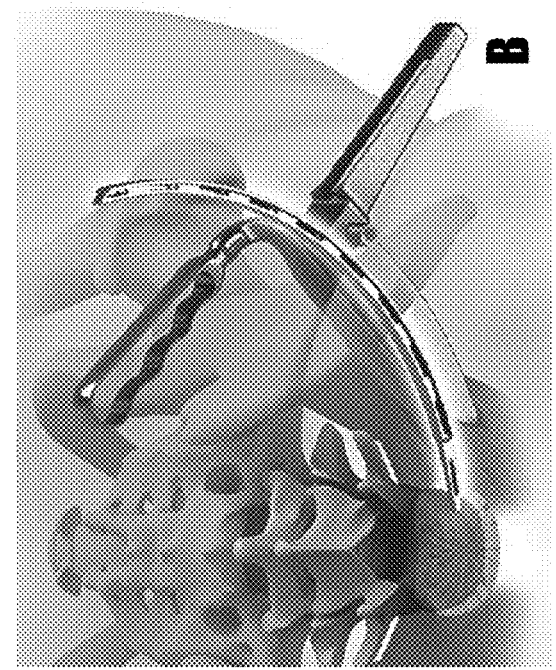
FIG. 21
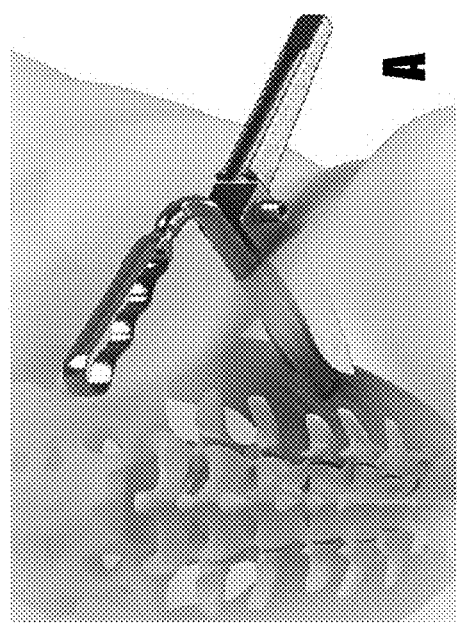
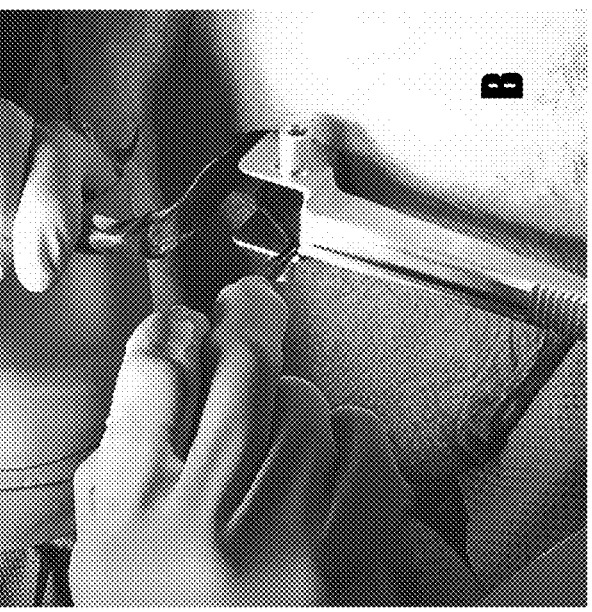
FIG. 20

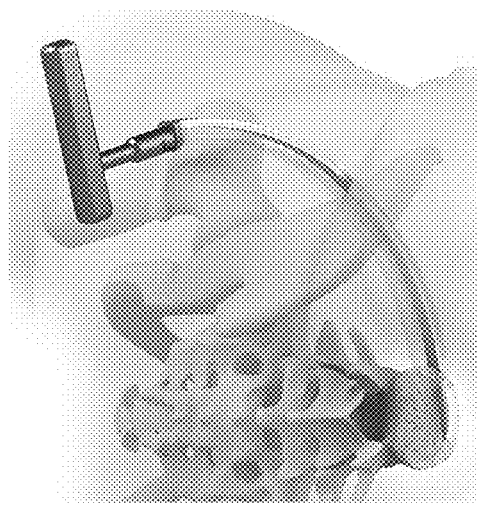
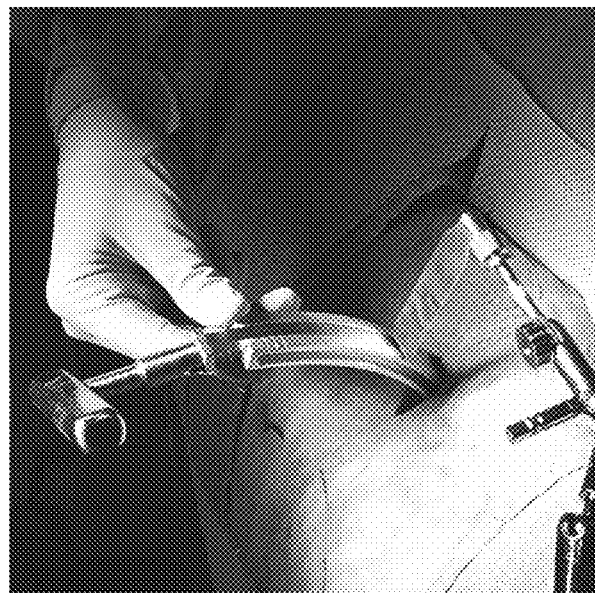
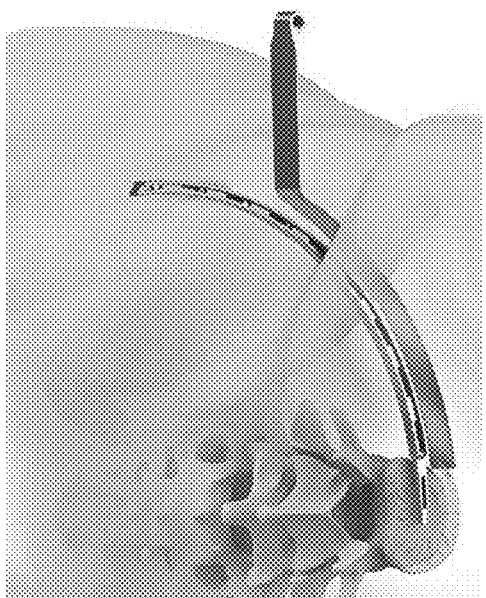
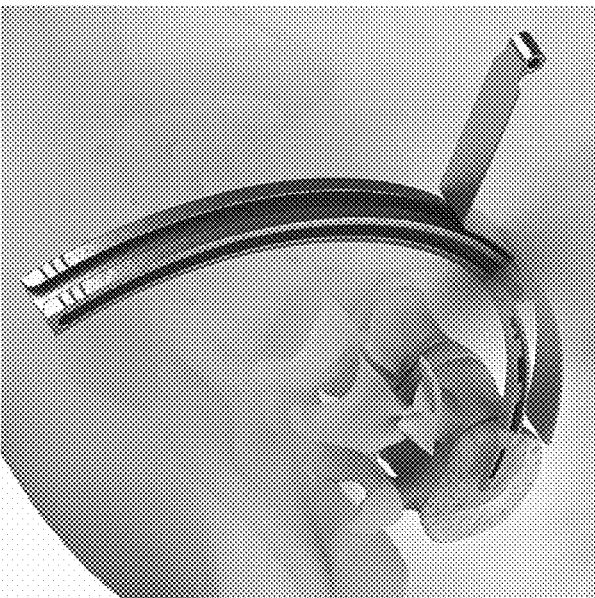
FIG. 21 (CONT.)
FIG. 22

A
B
FIG. 24
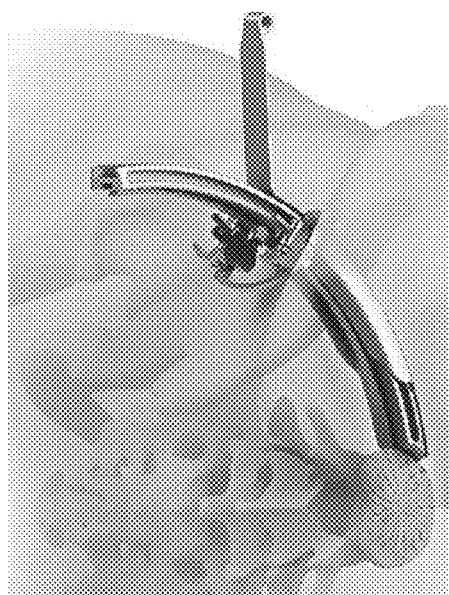
A
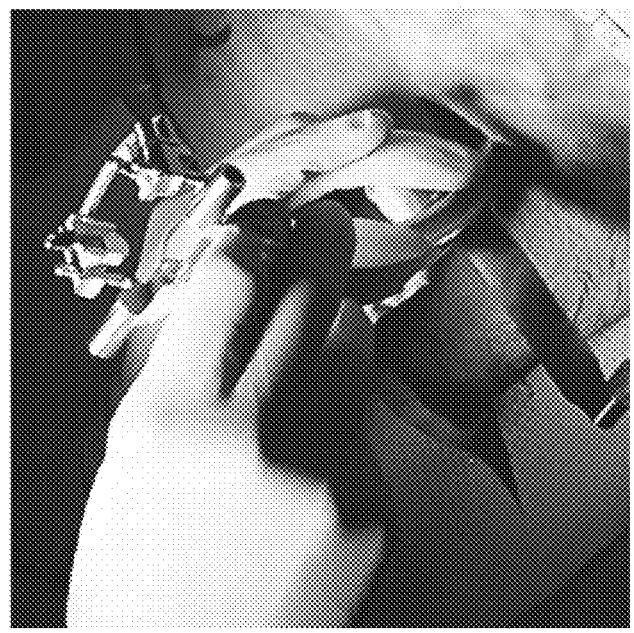
B
FIG. 23

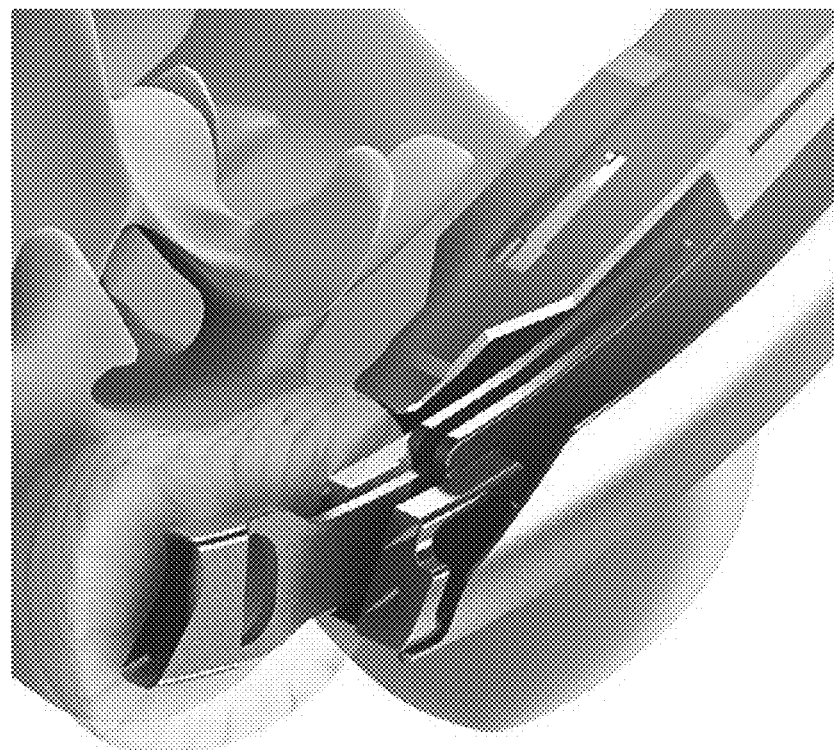
A
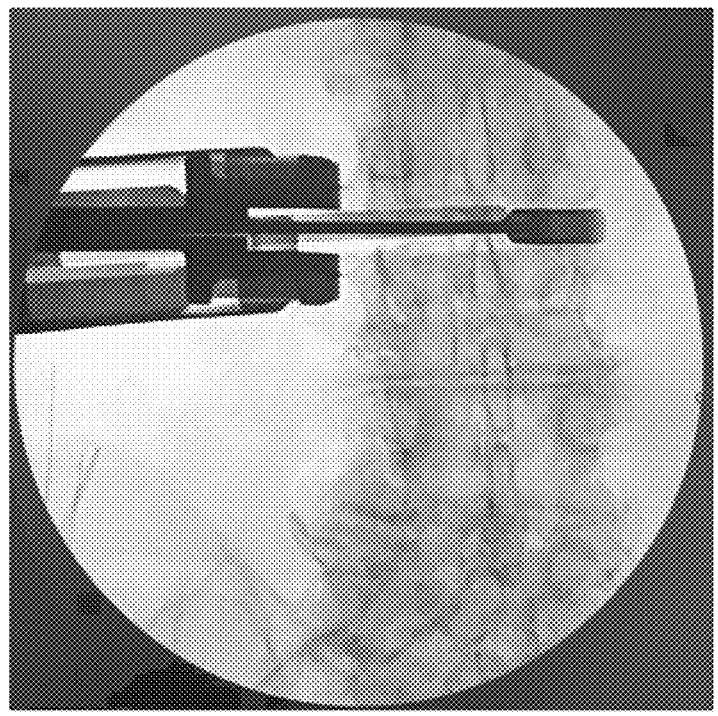
B
FIG. 26

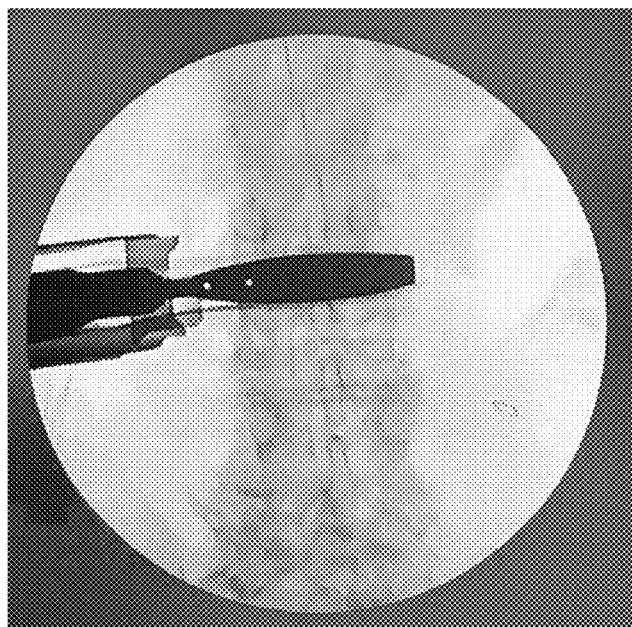
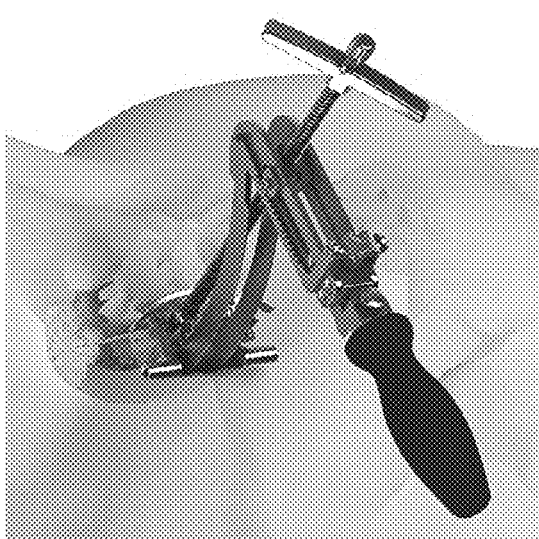
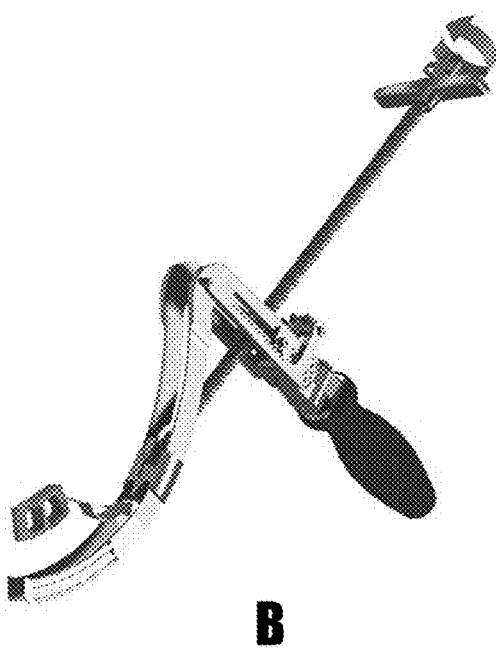
FIG. 27

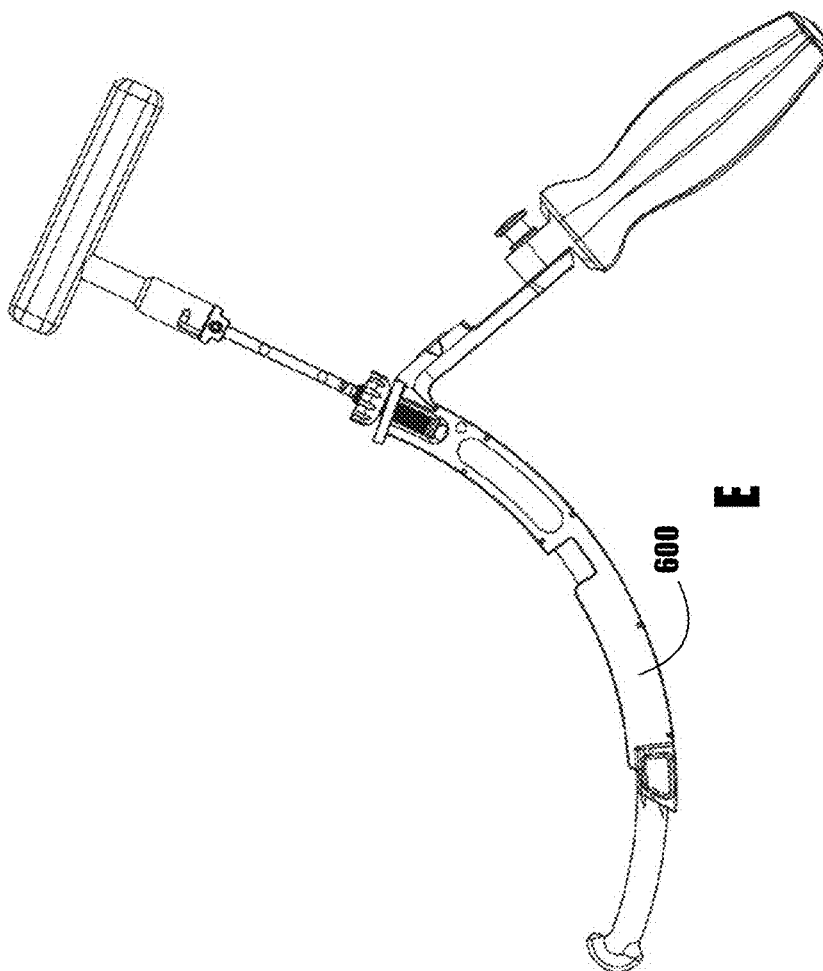
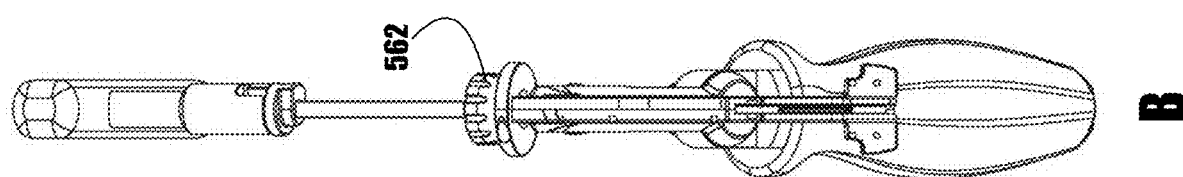
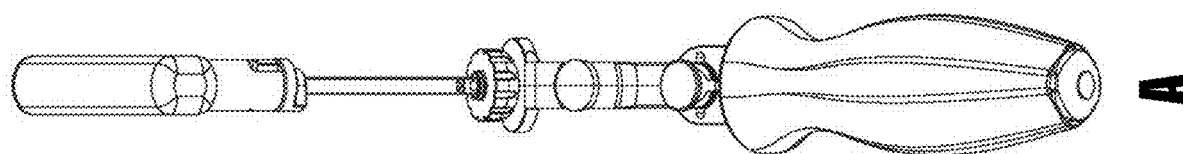
FIG. 30

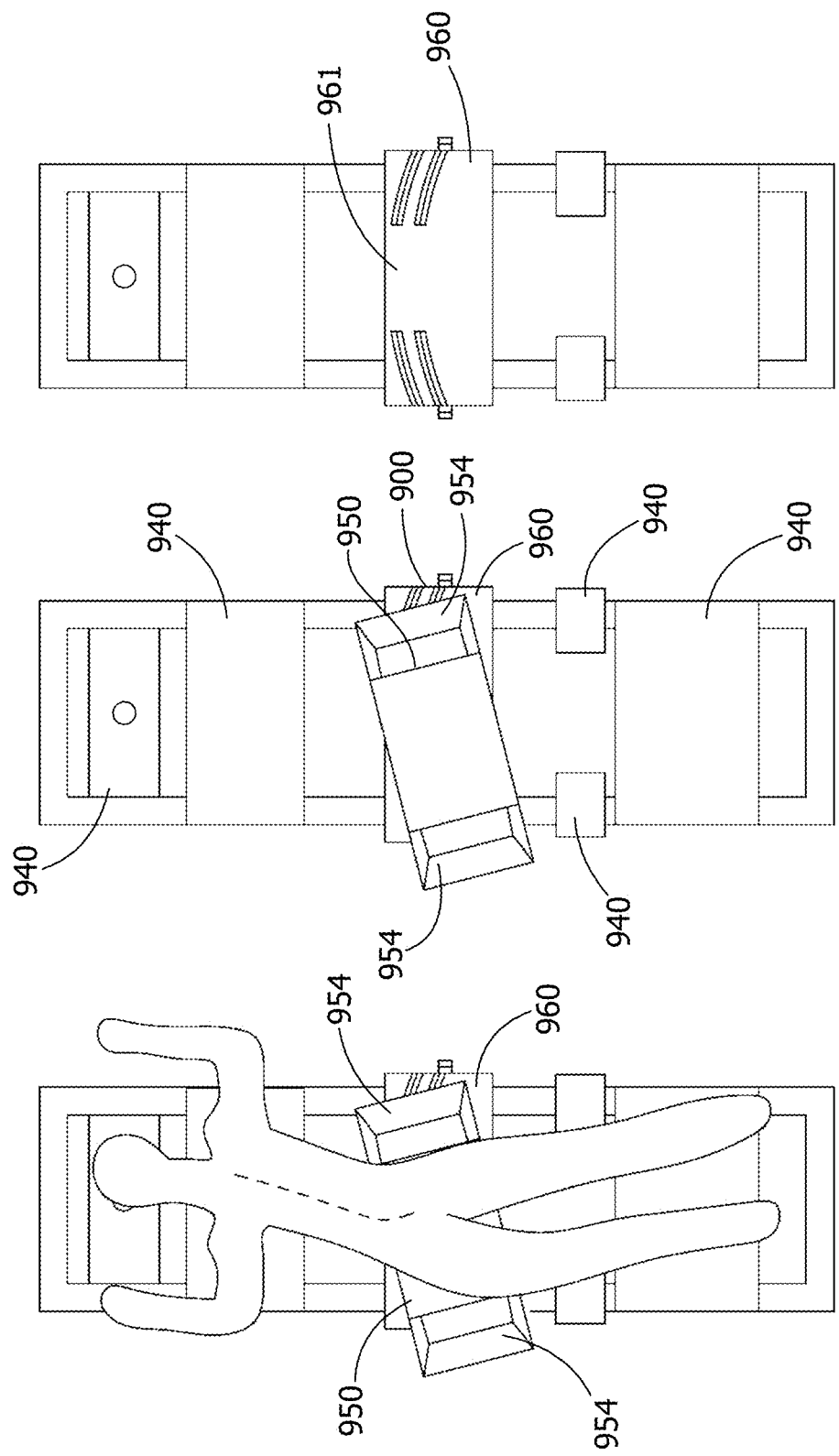

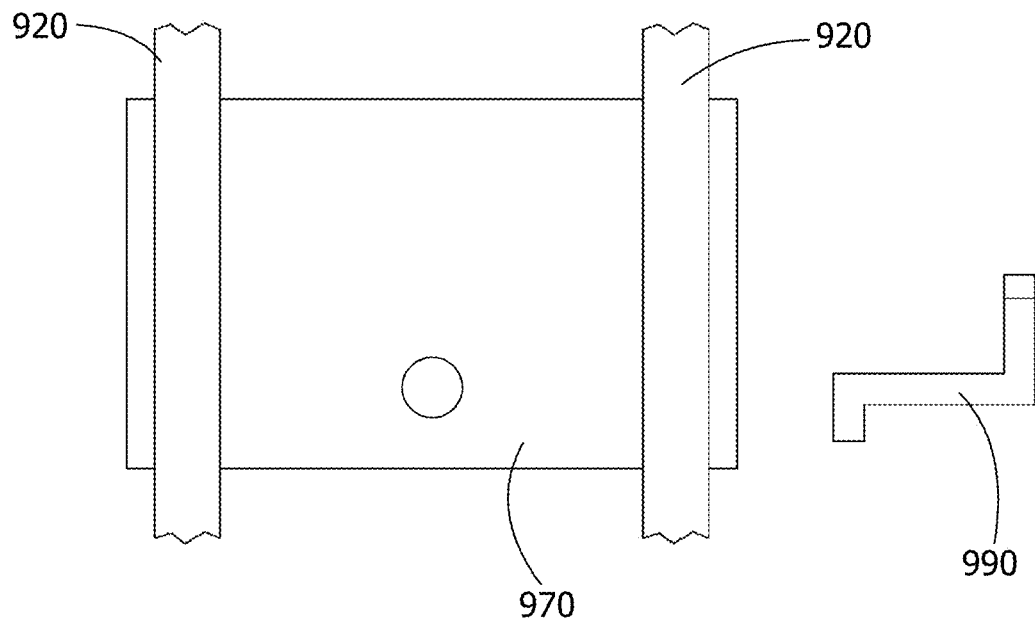
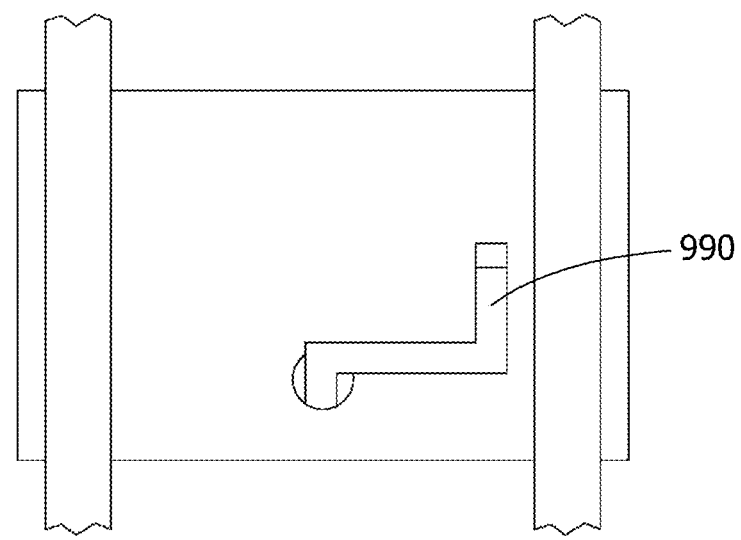
D (CONT)
FIG. 35 (CONT)

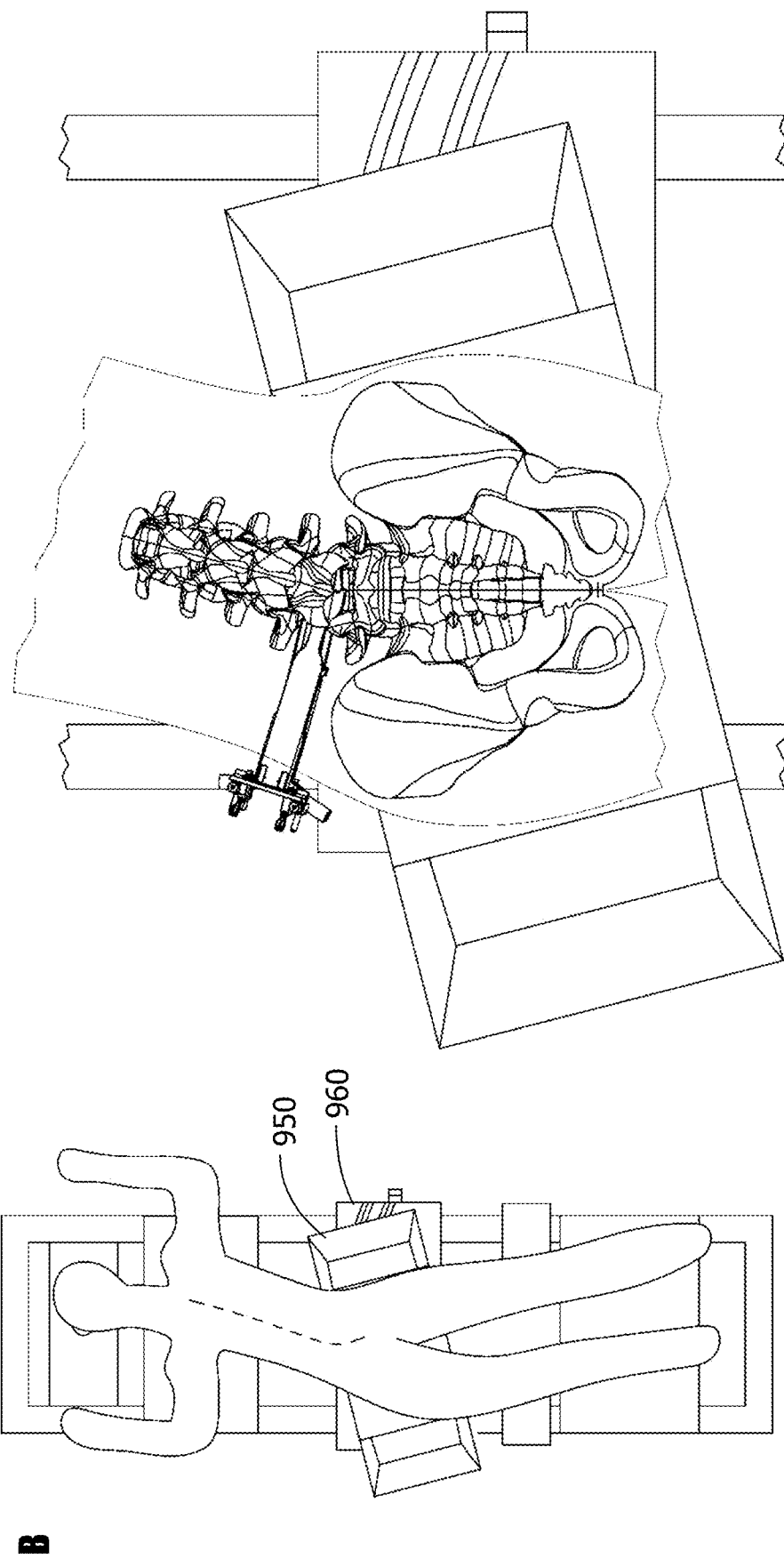

APPARATUS FOR POSITIONING A PATIENT DURING SURGERY TO MAXIMIZE ACCESS TO A SURGICAL SITE OF INTEREST

PRIORITY

This application is a continuation application of U.S. patent application Ser. No. 18/345,719 filed on Jun. 30, 2023, which was a continuation of U.S. patent application Ser. No. 16/875,507 filed on May 15, 2020, which was a divisional application of and claimed priority to U.S. patent application Ser. No. 16/028,817 filed Jul. 6, 2018, which is a divisional application of and claims priority to U.S. patent application Ser. No. 14/791,881, filed Jul. 6, 2015, which is related to Patent Cooperation Treaty Application PCT/US2015/039200 also filed Jul. 6, 2015, each of which applications claims the priority benefit under 35 U.S.C. § 119(e) to U.S. Provisional Application Ser. No. 62/021,202 filed Jul. 6, 2014, and Nos. 62/080,609, 62/080,573, 62/080,578, 62/080,590, 62/080,557, all filed Nov. 17, 2014, and No. 62/156,184, filed May 1, 2015, the entireties of which are incorporated herein by reference.

BACKGROUND

Field

The present application describes various exemplary devices, systems and surgical techniques for achieving access to a site within the body, particularly the spine. More particularly, the present application describes a system and device components for providing a minimally invasive retractor system for directly viewing and accessing a surgical site in the body, particularly the spine. In some exemplary embodiments, the system and device components are useful for accessing the spine for one or more purposes of manipulation, removal, replacement and reinforcement of intervertebral discs, particularly in the lumbar spine. According to such embodiments, the present invention overcomes shortcomings in the art.

Description of the Related Art

A common surgical approach for addressing spinal injuries and pathologies involves placement in the spine of one or more mechanical devices to enable clinical interventions for correcting the spine that include intervertebral stabilization, distraction, decompression, joint fusion and combinations of these. There are a variety of such mechanical devices. For example, implants referred to as interbody devices are inserted between two adjacent vertebrae within the space that is naturally occupied by the disc. Other devices, such as screws, plates, rods, and tethers are also used in various combinations, sometimes together with interbody devices, to achieve desired correction to the spine. Specialized instrumentation is required for implantation of each of these devices, and a wide range of surgical techniques and modes of access to the spine have been developed, presenting a large array of options and complexity for neurosurgeons and orthopedists who specialize in the spine.

Broadly, there are at least three general modes of access to the spine for achieving delivery of spinal correction devices. These general modes include anterior (through the abdominal cavity), posterior (including transforaminal), and lateral (including extreme lateral). For example, in the context of lumbar surgery, the lexicon includes the following terms that describe these various modes of access for achieving fusion between lumbar vertebrae: anterior mode of access is known as "ALIF" (Anterior Lumbar Interbody Fusion); posterior mode of access is known as "PLIF" (Posterior Lumbar Interbody Fusion); an alternate, minimally invasive posterior mode of access is known as "TLIF" (Transforaminal Lumbar Interbody Fusion); and lateral mode of access is known as "DLIF" (Direct Lumbar Interbody Fusion), including a minimally invasive lateral mode known as "XLIF" (eXtreme lateral Lumbar Interbody Fusion). Selection of the mode of access for a particular patient is dictated by a number of factors, including the extent of correction needed, the location within the spine requiring correction, and the preference and skill of the surgeon.

As with most other areas of surgery, is it preferable when operating on the spine to employ the least invasive surgical approach possible for achieving correction to minimize trauma and associated pain and blood loss experienced by the patient, to improve recovery time and outcomes, and to reduce operating room time and costs. Thus, while good results have historically been achieved through full-open access to the spine (typically through one of anterior and posterior routes), there is significant attention to developing minimally invasive surgical approaches. Each of the various open and minimally invasive techniques involve specialized instrumentation for achieving surgical access, and particularly for the minimally invasive approaches, specialized devices have been developed that are adapted for delivery according to the selected technique and the associated instrumentation.

In accordance with the various methods of spinal access, there are several commonly shared requirements and steps. In all cases, it is necessary for the surgeon to determine the proper size of the disc space (or spaces) to be accessed so as to select appropriately sized implant(s); this is typically achieved with preoperative imaging, in particular, MRI and CAT scans. And a fluoroscopy machine (C-arm) is on hand to provide real-time x-ray images, particularly in those procedures where the spine cannot be directly visualized due to impedance of soft tissue or small surgical field. In some instances, neuro-monitoring equipment is used to ensure that the instrumentation and implants are not causing damage to spinal nerves. This equipment typically measures spinal nerves indirectly by monitoring changes in leg muscle reflexes over time.

In all modes of approach, one or more special retractors and tubes are typically used to dissect and displace tissue and expose the vertebrae, and other instruments are used to release the annulus and open the disc space, remove disc material, and prepare the space to receive an implant. Thereafter, one or more interbody implants is inserted in the prepared space, typically together with one of a variety of bone graft and osteogenic materials. In some examples, the implants are secured to one or both vertebral end plates using screws. During the procedures one or multiple levels of fusion may be completed. Beyond these common steps, there is a good degree of variation in technique and instrumentation for each of the modes of spinal access.

Anterior Access

Anterior Lumbar Interbody Fusion involves access to the spine from the front (anterior) of the patient's body, usually through an incision in the lower abdominal area or on the side. ALIF may be executed as a full-open procedure or as a minimally invasive procedure, for example, using laparoscopes, and involves cutting through, and later repairing, the muscles in the lower abdomen, and retracting (temporarily moving or displacing) muscles and blood vessels to gain access to the spine. ALIF advantageously allows for direct access to the disc space at all vertebral levels without need to resect spinal bone and without trauma to posterior muscles and nerves. Delivery of large sized implants is possible via ALIF. Disadvantageously, for all ALIF procedures, the patient must be in a supine position (on her/his back). Because it does not allow for posterior access to install pedicle screws, rods, tethers and other implants that stabilize the spine, the patient must be repositioned from supine to prone after the ALIF procedure is completed in order to gain posterior access to the spine. Repositioning typically extends the time in the operating room and can introduce additional risk. Further, ALIF access typically requires the involvement of other surgeons, such as general surgeons, adding time and cost to the procedure.

Posterior Access

Posterior Lumbar Interbody Fusion allows the vertebrae to be reached through an incision in the patient's back (posterior). PLIF may be executed as a full-open procedure or as a minimally invasive procedure. One of the perceived key advantages to this approach is that the spine is accessed while the patient is in a prone position on the operating table, thus avoiding the need for the patient to be repositioned on the table after an ALIF procedure, and allowing interbody placement to be achieved in parallel with pedicle screw and rod placement (i.e., implantation of the interbody device at the same time as other fixation devices). PLIF typically involves a 3-6 inch incision in the patient's back and retraction of the spinal muscles and nerves to allow access to the target intravertebral space, typically followed by removal of a portion of the vertebra called the lamina (laminectomy) and as needed, some portion of the facet joints. Thereafter, the affected disc material is removed to accommodate implantation of the interbody device and bone graft material. There are advantages to this surgical approach, including avoidance of the need for patient repositioning, and possibly improved rates of fusion due to the ability to achieve greater compression. Some of the disadvantages include risk of retropulse of the implant into the canal which can cause neural compression, and incomplete clearance of the disc space due to access limitations posed by posterior bone.

Transforaminal Lumbar Interbody Fusion is a refinement of the PLIF procedure and has recently gained popularity as a minimally invasive surgical technique for conditions affecting the lumbar spine. The TLIF technique involves approaching the spine in a similar manner as with PLIF but the spinal target site is displaced laterally, away from the posterior centerline of the spine and toward the side of the spinal canal. As compared with PLIF, this approach enables a relatively reduced amount of surgical muscle dissection and nerve manipulation to access the disc space. And as compared with ALIF, this approach does not require the presence of a general surgeon, or the risks involved in access through the peritoneal cavity, or the need for rotation of the patient. A key disadvantage to this mode of access is the requirement for blunt dissection through the psoas muscle and the attendant problem of compression or dissection damage to nerve tissue that runs through the psoas muscle. This is particularly a problem since the field of view available in the TLIF technique is very limited making accurate identification of the nerve tissue a challenge.

Lateral Access

Direct Lumbar Interbody Fusion, and the minimally invasive counterpart, Extreme Lateral Lumbar Interbody Fusion, avoids an incision to the abdomen and avoids cutting and disrupting the muscles of the back. According to this mode of approach, the disk space is accessed from a very small incision on the patient's side (flank). The patient must be in a lateral recumbent or recovery position (on her/his side). As compared with PLIF, this approach reduces the amount of surgical muscle dissection and is intended to minimize the nerve manipulation required to access the intervertebral space. And as compared with ALIF, this approach does not require the presence of a general surgeon, or the risks involved in access through the peritoneal cavity. But DLIF/XLIF specifically presents some of the same challenges as TLIF in terms of trauma to the posas muscle and possible neropraxia due to compression caused by the retraction instruments. And because the procedure does not allow posterior access, any procedures that require direct posterior access must be done serially rather than in parallel with the interbody implantation.

Posterior Lateral Access

Other less invasive lateral-type approaches have been developed or proposed using posterior entry and lateral access to the spine via a curvilinear path. Such systems rely on fixation of the instrumentation/retractor either at its proximal end (i.e., proximate to the surgeon, outside the patient's body) to structures having positions that are fixed relative to the spine (i.e., instruments that are fixed in space either through attachment directly to the spine or to other fixed position structures), or at more than one location at the distal end (such as, for example, dorsal and ventral tangs that pierce into the disc and/or inferior/posterior pins that engage with each of the adjacent vertebra. Experience with such systems that have actually been manufactured has shown that reliance on such fixation does not effectively maintain the position of the curvilinear retractor at the spinal access site (i.e., the instrument's portion that is distal relative to the surgeon), resulting in significant slippage and/or displacement of the retractor from the spine during manipulations and implant placement. Moreover, the visualization that is achieved using substantially tubular curvilinear retractors is quite poor and impractical for the useful conduct of surgical procedures within the disc space.

While the overall curvilinear shape and the use of fixation means are intended to enable posterior lateral access, such systems are essentially rigid assemblies that don't allow the surgeon to manipulate soft tissue in order to optimize positioning and securement, provide only a limited effective view of the surgical field due to the relatively closed nature of the portal, and they don't ameliorate the concussive forces involved in tissue removal and implant delivery. These and other disadvantages with existing posterior-lateral instruments and approaches preclude the successful implementation a surgical approach that is otherwise favorable for overcoming many of the limitations and disadvantages of the TLIF, XLIF, and PLIF procedures and instruments.

There is a need for a surgical approach and associated instrumentation and devices that avoid the existing complications known in the art with the various modes of spinal access. More specifically, there is a need for advances with instrumentation and surgical technique to allow for the more desirable prone patient positioning during spinal access surgery combined with the benefits of lateral access to the target intervertebral space.

SUMMARY

In accordance with the disclosure, a direct visualization retractor system is disclosed which is adapted for surgical access, in particular suitable for stable engagement with the spine, and which in various embodiments is adjustable in an array of modes to accommodate a passage of surgical tools and implants. The system is particularly useful for use on a patient in a prone position while achieving lateral access to the spine, thus overcoming a host of disadvantages in the existing art. The direct visualization retractor system comprises a retractor body component and a retractor hood component, each of which operate independently to achieve soft tissue retraction in a surgical field, and which fixedly engage together to establish a stable and open channel from the exterior of a patient's body to the target tissue, for example the spine.

In some embodiments, the present invention provides a method for performing a procedure on the spine of a patient. The method also provides for coupling the components in situ to form a direct visualization surgical retractor system for access to a surgical site located at the spine of the patient. In accordance with the method, independent insertion and navigation of each of the retractor system components enables maximal dilation and retraction of soft tissue with enhanced tissue sparing.

Each retractor system component is independently placed adjacent to the target tissue, in the case of interbody fusion, the spine, using contoured features on the distal ends of the components. Nesting the hood component within the chute of the retractor component before coupling allows for maximal manipulation of the soft tissue prior to full tissue distraction. Upon engagement of the retractor system components, the various modes of adjustability enable optimized placement of the hood and expansion of the access channel. Engagement of one or more tissue fixation members enables enhanced stabilization of the retractor system.

The method further includes advancing one or more surgical instruments and implants to the target tissue site. Instruments may include, for example, any one or more of shims, osteotomes, tissue distractors, and inserters, and implants may include, for example, any one or more of bone screws, plates, interbody devices, artificial discs, and any other implants suitable for use in the spine.

Embodiments of the present invention are not limited to use in a posterior-lateral approach for spinal surgery and may also be used in many other surgical approaches, including approaches to the spine, such as anterior (ALIF), posterior (PLIF), transverse (TLIF), and extreme lateral (XLIF). Embodiments of the present invention should also not be limited to the spine and may be used in other orientations and other surgical sites within the body.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 19 includes in panels A, B, and C respectively front, back and oblique views of an embodiment of a first dilator, in panels D, E and F, respectively, front, back and oblique views of an embodiment of the second dilator, and in panels G, H and I, respectively, front, back and oblique views of an embodiment of an tang awl;

FIG. 20 includes in panel A a schematic showing the insertion path through human anatomy and orientation relative to the spine of insertion instruments in accordance with the disclosure, and in panel B a photograph showing the insertion instruments of panel A as inserted into a human model;

FIG. 21 includes in panel A an alternate view of the schematic shown in FIG. 20 A further depicting the insertion of an awl, and in panel B another alternate view of the schematic shown in FIG. 20 A further depicting the insertion of a first elongate dilator, and in panel C another alternate view of the schematic shown in FIG. 20 A further depicting the insertion of a first elongate dilator and a ribbon blade, and in panel D another alternate view of the schematic shown in FIG. 20 A further depicting the insertion of a second elongate dilator adjacent to the first elongate dilator and a ribbon blade;

FIG. 22 includes in panel A another alternate view of the schematic shown in FIG. 20 A further depicting the insertion of an tang awl adjacent to the second elongate dilator and a ribbon blade, and in panel B a photograph showing the insertion instruments of panel A as inserted into a human model;

FIG. 23 includes in panel A another alternate view of the schematic shown in FIG. 20 A further depicting the insertion of a modular retractor component adjacent to the second elongate dilator and ribbon blade, and in panel B a photograph showing the insertion instruments of panel A as inserted into a human model;

FIG. 26 includes in panel A a close up of the distal/front end of a punch blade of a cutting assembly depicting insertion of the punch blade through and into a disc toward the contralateral disc annulus, and in panel B a radiographic image from a human model showing an anterior to posterior (AP) view of a human spine showing insertion of the punch blade as depicted in panel A;

FIG. 27 includes in panel A a radiographic image from a human model showing an anterior to posterior (AP) view of a human spine showing positioning of an paddle distractor within the disc space for preparation thereof to receive an implant, and in panel B a schematic showing an embodiment of an tissue preparation device and a disc implant for attachment thereto, and in panel C a schematic showing an oblique proximal/back end view of the tissue preparation device inserted through the modular retractor depicting transit of the implant along the path of the retractor and toward the disc space by actuation of the instrument driver;

Figure 1:
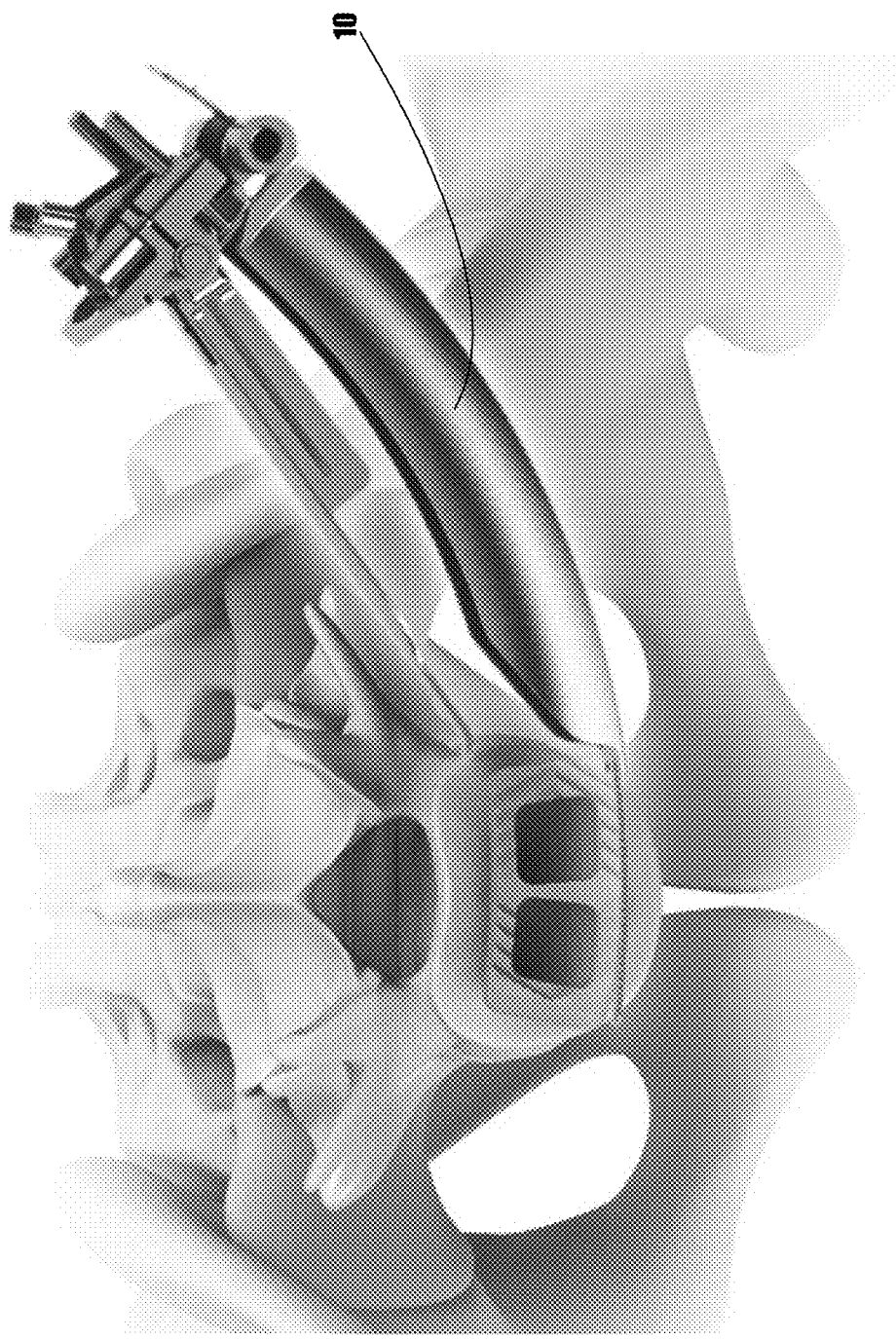
FIG. 1 is a schematic showing an assembled modular retractor in accordance with the disclosure in relation to a spine as seen along the inferior to superior axis.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

The general inventive concepts will now be described with occasional reference to the exemplary embodiments of the invention. The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

This disclosure describes exemplary embodiments in accordance with the general inventive concepts and is not intended to limit the scope of the invention in any way. Indeed, the invention as described in the specification is broader than and unlimited by the exemplary embodiments and examples set forth herein, and the terms used herein have their full ordinary meaning.

The general inventive concepts are described with occasional reference to the exemplary embodiments of the invention. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

With respect to any references herein that may be made relative to a human patient, the terms "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient, the term "medial" indicates a direction toward the midline of the patient, and away from the side, the term "ipsilateral" indicates a direction toward a side that is proximal to the operator or the object being referenced, and the term "contralateral" indicates a direction toward a side that is distal to the operator or the object being referenced. More generally, any and all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach, and according to the exemplary embodiments herein, are based on a representative spinal access retractor system having a radius of curvature as described, being suitable for any number of animal patients, including humans and other species. Of course, the type of surgery, target tissue, and species of patient may be different than is disclosed in the exemplary embodiments described herein, and in some embodiments, all or most components of the system may be rectilinear.

Further, all references herein are made in the context of the representative images shown in the drawings. Fewer or additional generic instruments may be used according to the preference of the operator. Moreover, references herein to specific instruments are not intended to be limiting in terms of the options for use of other instruments where generic options are available, or according to the preference of the operator.

Modular Retractor and Direct Visualization Channel

As described herein above, there is a need for devices and systems that overcome the shortcomings in the art pertaining to minimally invasive surgical access, particularly access for spinal surgery. In view of this need, the embodiments of devices, systems, and surgical methods provided herein address a variety of objects and advantages. The present application describes various exemplary devices, systems and surgical methods for achieving surgical access to a site within the body, particularly the spine. More particularly, the present application describes a system and device components for providing a minimally invasive retractor system for directly viewing and accessing a surgical site in the body, particularly the spine. In some exemplary embodiments, the system and device components are useful for accessing the spine for one or more purposes of neural decompression, manipulation, removal, and replacement and reinforcement of intervertebral discs, particularly in the lumbar spine.

Referring now to the drawings, FIG. 1 is a schematic showing an assembled modular retractor in accordance with the disclosure in relation to a spine as seen along the inferior to superior axis. In certain embodiments, the retractor system is suitable for facilitating interbody fusion between adjacent vertebrae, and in particular, lumbar interbody fusion. Referring to the representative embodiment of the retractor system shown in FIG. 1, the direct visualization retractor system enables creation of an open and essentially unobstructed channel for visualizing and surgically accessing the spine. As more fully described herein below and in the representative drawings, the retractor system includes, in various embodiments, features that enable stable positioning relative to the spine, and tissue-sparing retraction of nerves and muscle. Advantageously, in certain embodiments, a curvilinear shape of the direct visualization retractor system, as depicted in FIG. 1, is particularly well suited for achieving lateral approach to the spine through a posterior access site.

The posterior-lateral procedure begins with placing a patient in a prone position on a surgical table (e.g., Jackson Table) with the axis of the lumbar spine generally parallel with the operating room floor. Posterior-lateral access and prone positioning of the patient offers many advantages over the current alternative approaches to LIF, including, but not limited to: eliminating the need to reposition the patient for posterior stabilization and minimizing risk to vital soft tissues as compared with ALIF; minimizing nerve compression compared to a straight oblique approach; delivering an implant with better anatomic physiology without requiring drastic repositioning; protecting anterior aspect and protecting the bowels from injury; preserving posterior bone; allowing use of a larger implant and avoidance of bone removal as compared with TLIF; and presenting the patient in manner that is more familiar to the typical spine surgeon and more comfortable for the surgical subject as compared with the XLIF and other direct lateral LIF procedures.

Of course, it will be appreciated that other modes of access to the spine can also be achieved, particularly with alternate, non-curvilinear embodiments of the retractor system, as described herein below. Likewise, it will be appreciated that any one or more of a variety of surgical procedures can be performed through the direct visualization retractor system, including but not limited to, removal of annulus material, vertebral distraction, graft and/or interbody implant insertion, and attachment of one or more plates and/or screws. In addition to enabling direct visualization for a lateral approach to the spine, other specific features and advantages of the retractor system and the surgical technique are described further herein.

Figure 2:
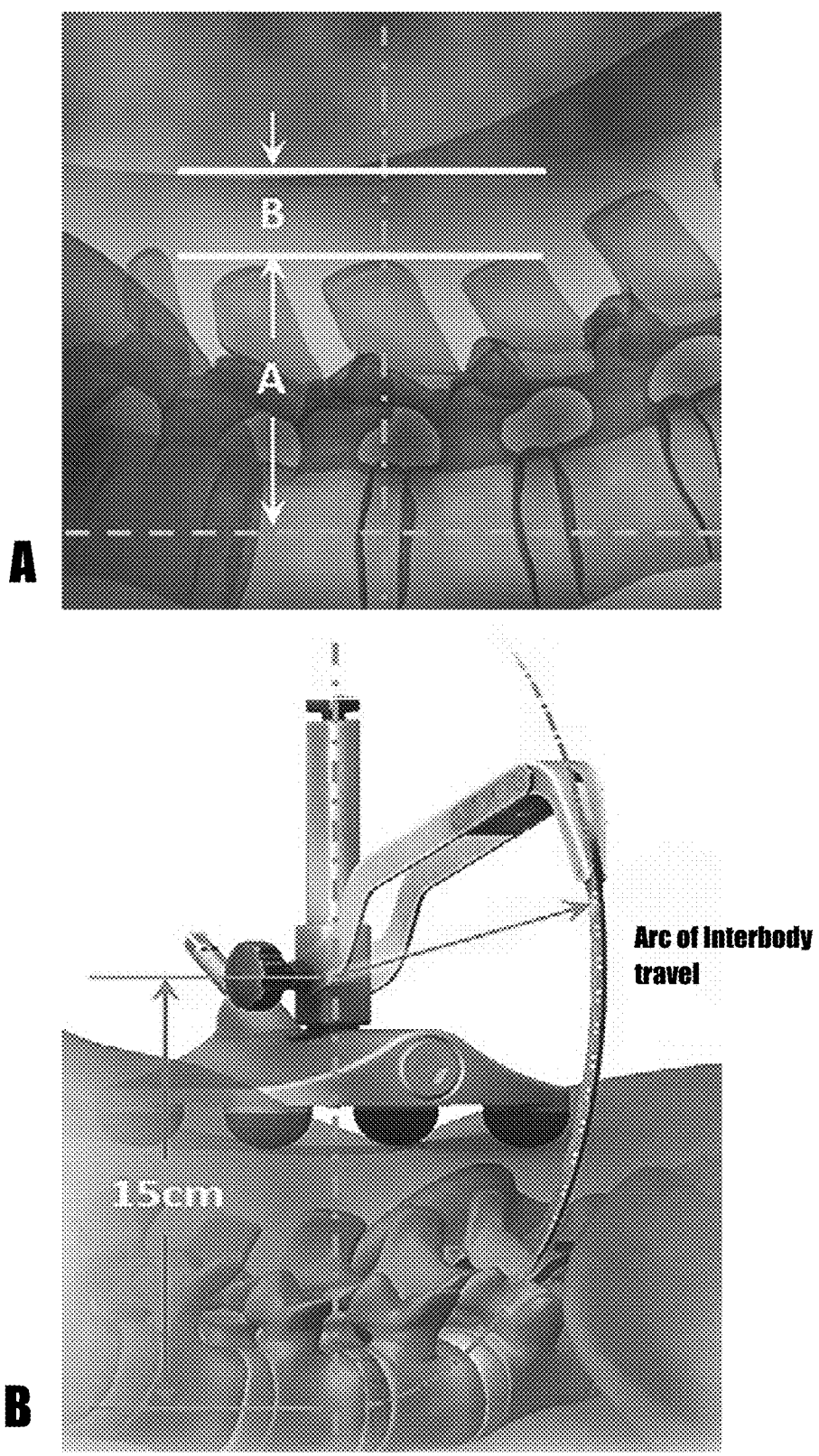
FIG. 2 includes in panel A a schematic showing a lateral view of a portion of a lumbar spine, and in panel B a schematic showing an incision guidance instrument in accordance with the disclosure positioned relative to a portion of a lumbar spine in the context of human anatomy.

In accordance with the surgical techniques described herein, the system provides the option for placement of a retractor system for accessing the spine. In some embodiments of the surgical techniques, an incision guidance instrument is used for selecting a desirable incision site for insertion of the retractor system to achieve placement at the desired location relative to a target spinal intervertebral space. Referring again to the drawings, FIG. 2 shows an exemplary embodiment of an incision guidance instrument in accordance with the disclosure, the instrument positioned relative to a portion of a lumbar spine in the context of human anatomy. FIG. 2 Panel A is a schematic showing a lateral view of a portion of a lumbar spine and panel B a schematic showing key spinal landmarks that are relevant to the positioning of the incision guidance instrument and selection of the incision site.

Figure 3:
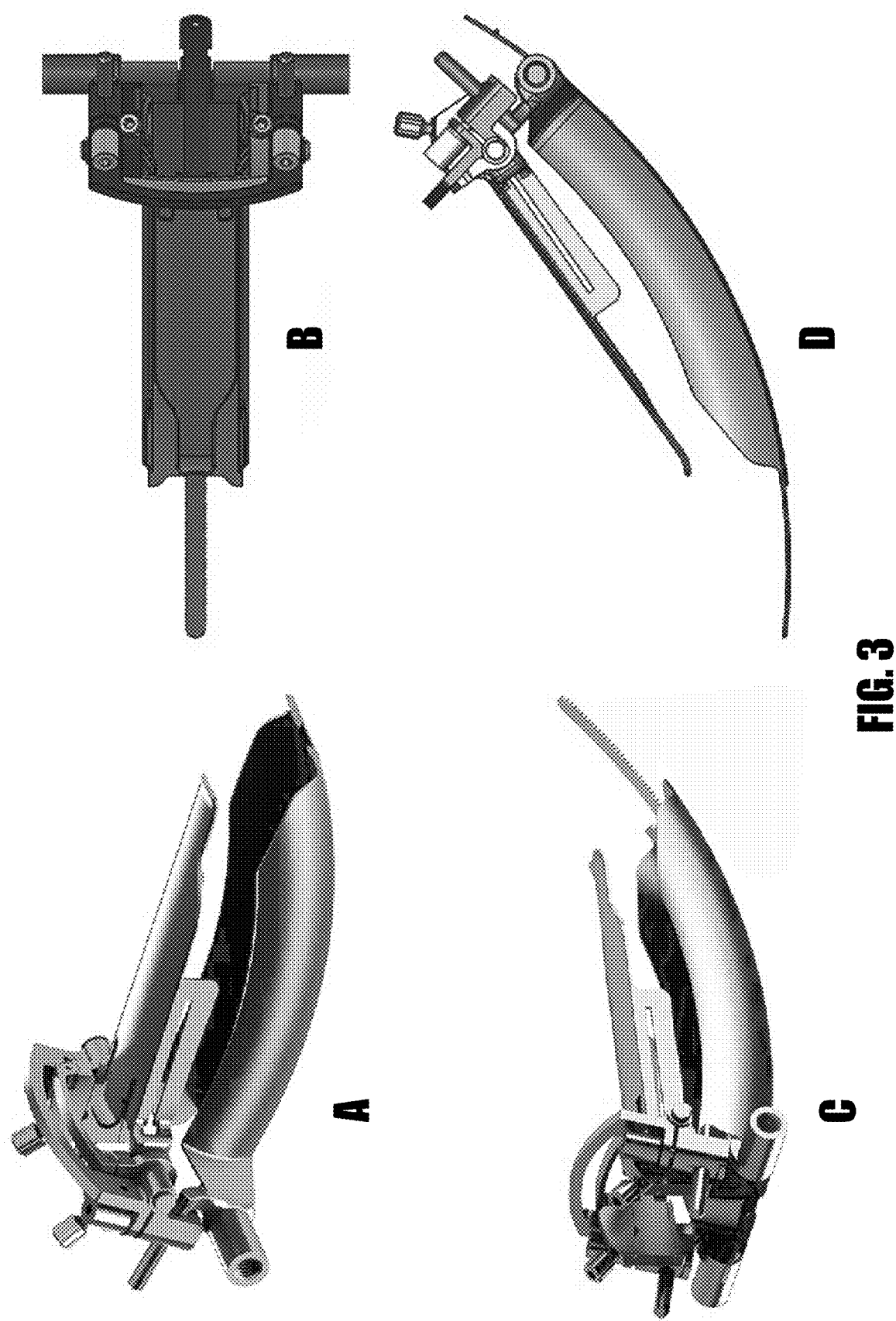
FIG. 3 includes in panels A, B, C and D, respectively, schematics showing alternate oblique, top, oblique and side views of an assembled modular retractor in accordance with the disclosure.
Figure 4:
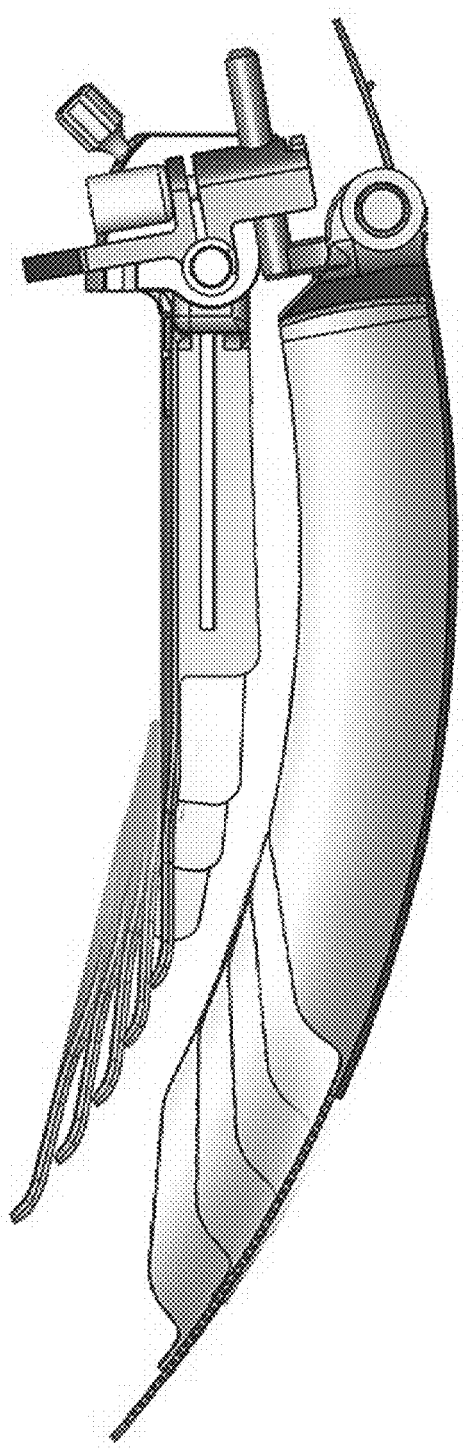
FIG. 4 is a schematic showing a side view of an assembled modular retractor in accordance with the disclosure wherein a series of different lengths of the retractor are shown nested to illustrate incremental modular component sizes.

Referring now to FIG. 3, the direct visualization retractor system is adapted for engagement at its distal end with the spine and comprises retractor body and hood components, each of which is discretely operable to achieve dilation and retraction of soft tissue, and which are adapted for interengagement in a variety of configurations to provide an adjustable and stable retractor system. FIG. 3 includes in panels A, B, C and D, respectively, schematics showing alternate oblique, top, oblique and side views of an assembled modular retractor in an open configuration, in accordance with the disclosure. And FIG. 4 is a schematic showing a side view of an assembled modular retractor in accordance with the disclosure wherein a series of different lengths of the retractor hood and body are shown nested to illustrate exemplary incremental modular component sizes. A representative modular retractor device and its components are shown in various views in FIG. 5-FIG. 11, particulars of which will be described in detail herein below.

While various features and aspects of the modular retractor may vary according to the disclosure, in some embodiments of the instant invention, the retractor components are particularly suited for posterior-lateral access to the spine, wherein one or more components has a generally curved profile, being curved along an elongate axis. In yet other embodiments, the devices and systems are particularly suited for a surgical procedure that is achieved along a generally rectilinear (i.e., uncurving) path, such as via a direct anterior, posterior, or lateral approach wherein suitable embodiments of the device and system components are essentially rectilinear, or have a nominal curvature with a radius of curvature.

Figure 12:
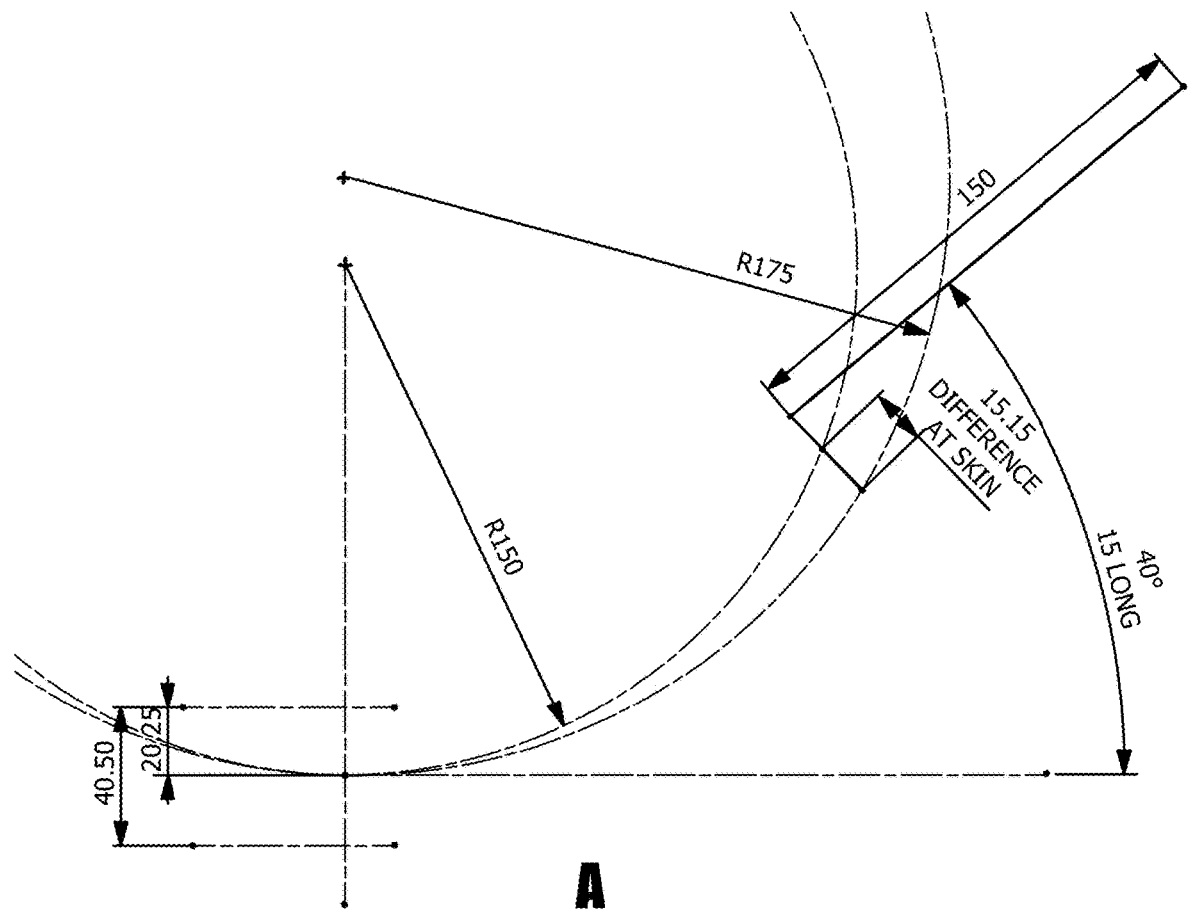
FIG. 12 includes in panel A a schematic showing a side view of an embodiment of a modular retractor in an open position in accordance with the disclosure indicating a radius of curvature and other features, and in panel B a radiographic image with an overlay of representative radii of curvature of modular retractors and related instruments in accordance with the disclosure relative to the disc of a human spine as shown in a superior to inferior view.
Figure 12:
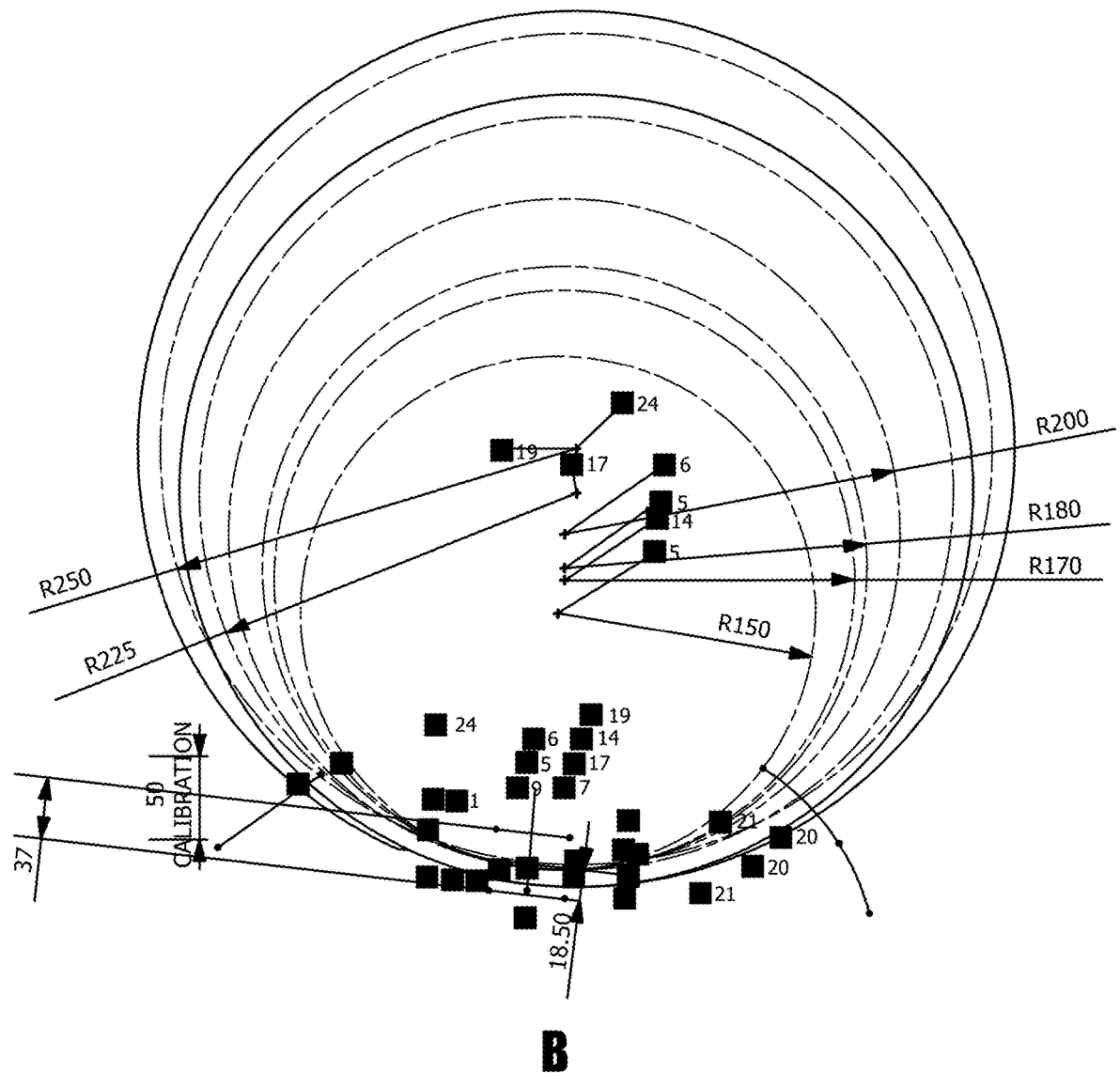

Referring now to FIG. 12, panel A is a schematic showing a side view of an embodiment of a modular retractor in an open position in accordance with the disclosure, the schematic indicating a radius of curvature R175, and also indicating the arc of an alternate optional radius of curvature R150. Panel B is a radiographic image of a human spine as shown in a superior to inferior view (also included in the image is a representative embodiment of an incision guidance instrument) with an overlay of six alternate representative radii of curvature. As shown relative to the disc, which is shown from an inferior to superior perspective, the path of the radius transects the disc approximately at its centerline and the radius is essentially coaxial with the centerline radius of the channel formed by the modular retractor. The depicted retractor includes a curvilinear retractor body, positioned ventrally and an essentially rectilinear hood positioned dorsally.

It will be appreciated by one of skill that the radius of the retractor and other instruments, as described herein below, are influenced by the selected radius of curvature for achieving lateral access to the disc space. Generally, the greater the radius, the flatter the channel and instruments, dictating a more ventral incision site on the patient, and the smaller the radius, the steeper the channel and instruments, dictating a more dorsal incision site on the patient. Thus, the points of access in the spine relative to the anterior to the center line to the posterior edge of the disc space may vary to accommodate the selected radius of curvature or lack thereof and enable delivery of an implant along the retractor to align with the centerline of the disc space.

Without being limiting, the radius of curvature of instruments according to the disclosure may be within a range from about 0 cm to about 60 cm, and more particularly from about 5 cm to about 25 cm, and in some embodiments the radius may be selected from one of 15 cm, 17 cm, 17.5 cm, 18 cm, 22 cm, 22.5 cm, and 25 cm. Of course other radii are possible within the range from 0 cm to more than 60 cm, including 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60, and incremental fractions thereof including 0.1, 0.2, 0.3, 0.4, 0.5, 0.6, 0.7, 0.8, 0.9 cm.

Referring again to the drawings, FIG. 3, the exemplary modular direct visualization retractor system includes elongate retractor body and hood components, each of which is operable independently for soft tissue retraction, and which fixedly couple to form the retractor system and establish a stable and open channel from the exterior of a patient's body to the target tissue. The modular direct visualization retractor system has a cross section that is generally elliptical or polygonal in shape, as shown in representative FIG. 3A.

Figure 38:
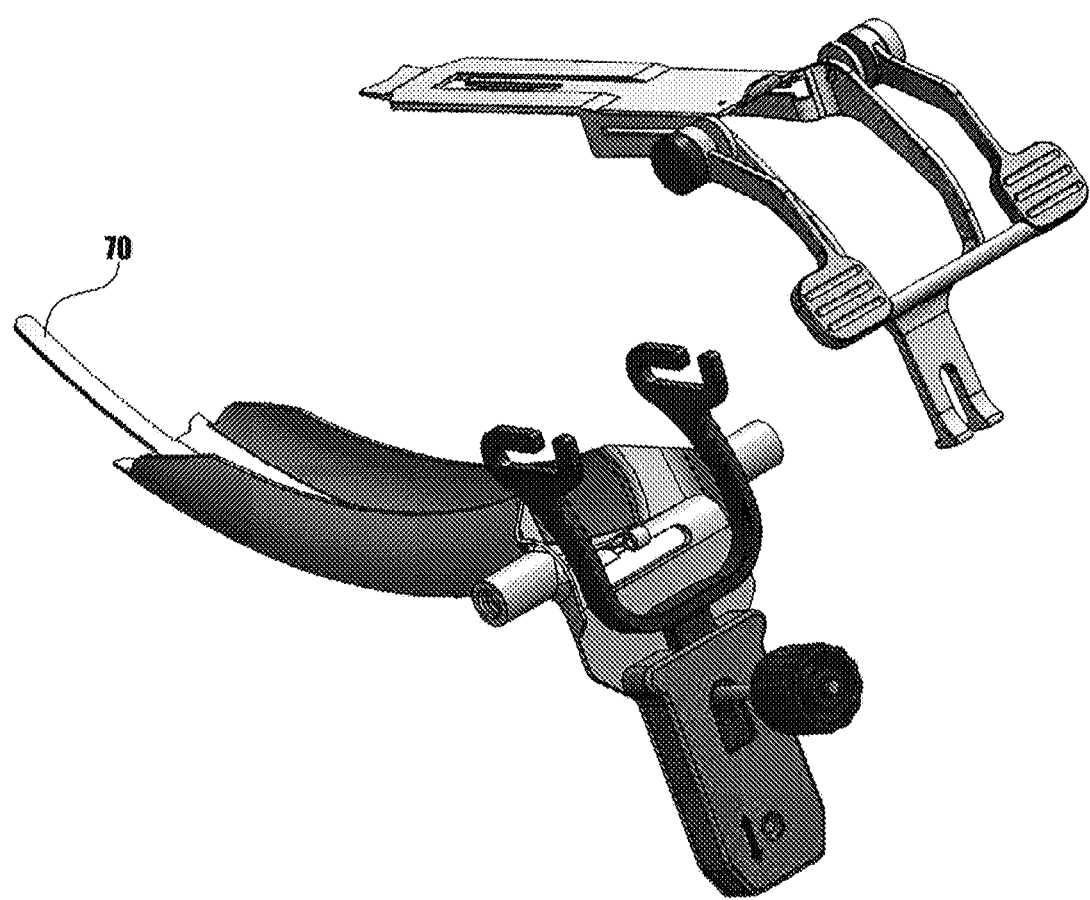
FIG. 38 is an oblique view of an alternate embodiment of an assembled modular retractor in accordance with the disclosure.
Figure 39:
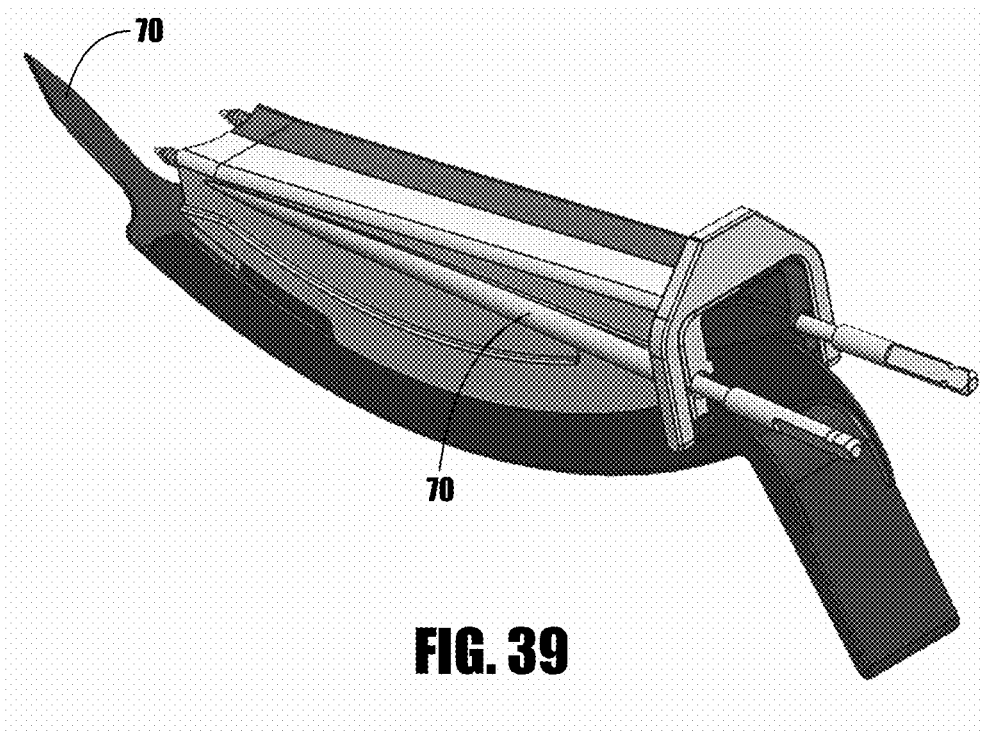
FIG. 39 is an oblique view of an alternate embodiment of an assembled modular retractor in accordance with the disclosure.
Figure 40:
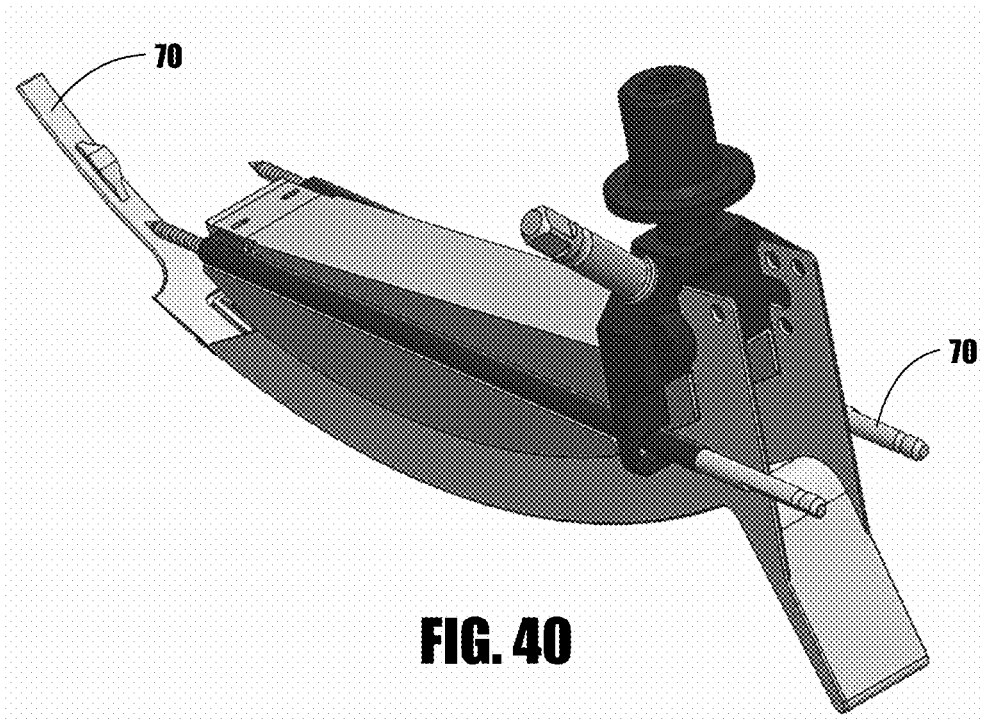
FIG. 40 is an oblique view of an alternate embodiment of an assembled modular retractor in accordance with the disclosure.
Figure 41:
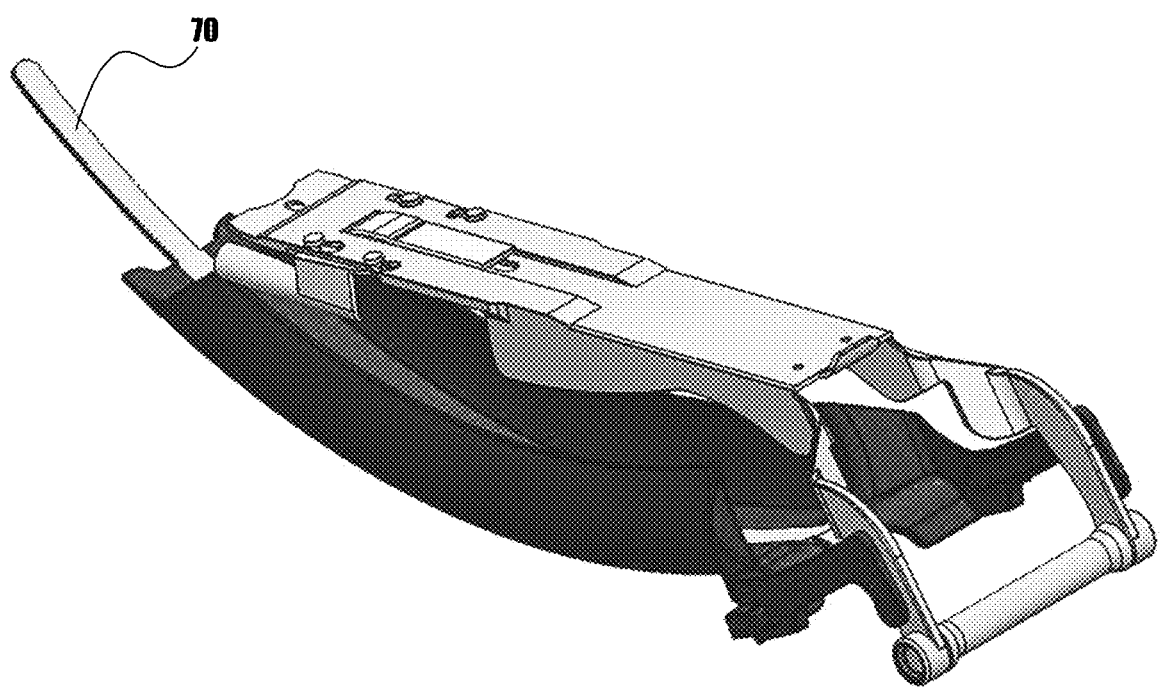
FIG. 41 is an oblique view of an alternate embodiment of an assembled modular retractor in accordance with the disclosure.
Figure 42:
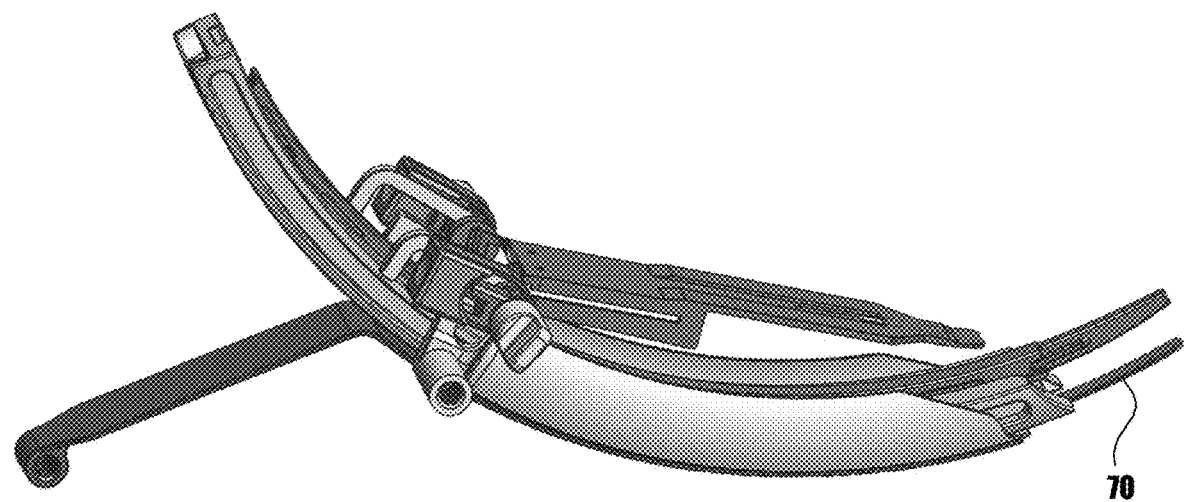
FIG. 42 is an oblique view of an alternate embodiment of an assembled modular retractor in accordance with the disclosure; and, FIG. 43 is an oblique view of an alternate embodiment of an assembled modular retractor in accordance with the disclosure.

Each of the elongate retractor body and hood components has a proximal end that is adapted to extend outside of the patient, and a distal end that is adapted for contact with the target tissue. The elongate retractor body depicted in the drawings is generally chute or trough shaped, the chute extending along a longitudinal axis between the proximal and distal ends, with a retractor floor and two opposing sidewalls that define the chute, and an open top. In some embodiments, as shown in FIG. 38, FIG. 39 and FIG. 40, at the retractor body's proximal end is a retractor body handle that is oriented relative to the chute at a downward angle, and most typically at an angle that is between 5 and 90 degrees. The exemplified handle shown in any one of the drawings is, of course, non-limiting, and the relative length and shape of the handle may vary. Likewise, the angle of orientation may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, or 179 degrees. Further, such handle may be removable, rotatable, pitched to the left or the right relative to the body of the retractor, and combinations of these.

Referring again to representative FIG. 3, the elongate hood is a generally planar narrow elongate body that extends along a longitudinal axis between the proximal and distal ends, and has a soft tissue elevator at its distal end, where in the depicted embodiment, the distal end is dipped to provide a recess between the more proximal portion of the planar body of the hood and an upwardly deflected tip. In some embodiments, as shown in FIG. 3E, at the hood's proximal end is a detachable hood guide that is used as a handle to guide and manipulate the hood within the incision, the guide oriented relative to the body of the hood at an upward angle that is between 5 and 90 degrees. Alternate views of a non-limiting embodiment of a handle are shown in FIG. 3F and FIG. 3G. The exemplified handle shown in any one of the drawings is, of course, non-limiting, and the relative length and shape of the handle may vary. Likewise, the angle of orientation may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, or 179 degrees. Further, such handle may be removable, rotatable, pitched to the left or the right relative to the body of the retractor, and combinations of these.

At their proximal ends, each of the retractor and the hood includes a coupling element for joining them together to form the modular direct visualization retractor system. The coupling elements include one or a plurality of fasteners, for example, pins, on one or the other of the retractor and hood, and one or a plurality of receivers, for example elongate slots, on the other of the retractor and the hood. In operation, the fasteners (e.g., pin(s)) slidably engage in the receivers (e.g., elongate slot receiver(s)) to couple the hood to the retractor to form the surgical access retractor system, and are adapted to enable relative pivoting of the hood and retractor at their proximal ends, and relative sliding of the hood and retractor along the common longitudinal axis of the retractor system.

Figure 7:
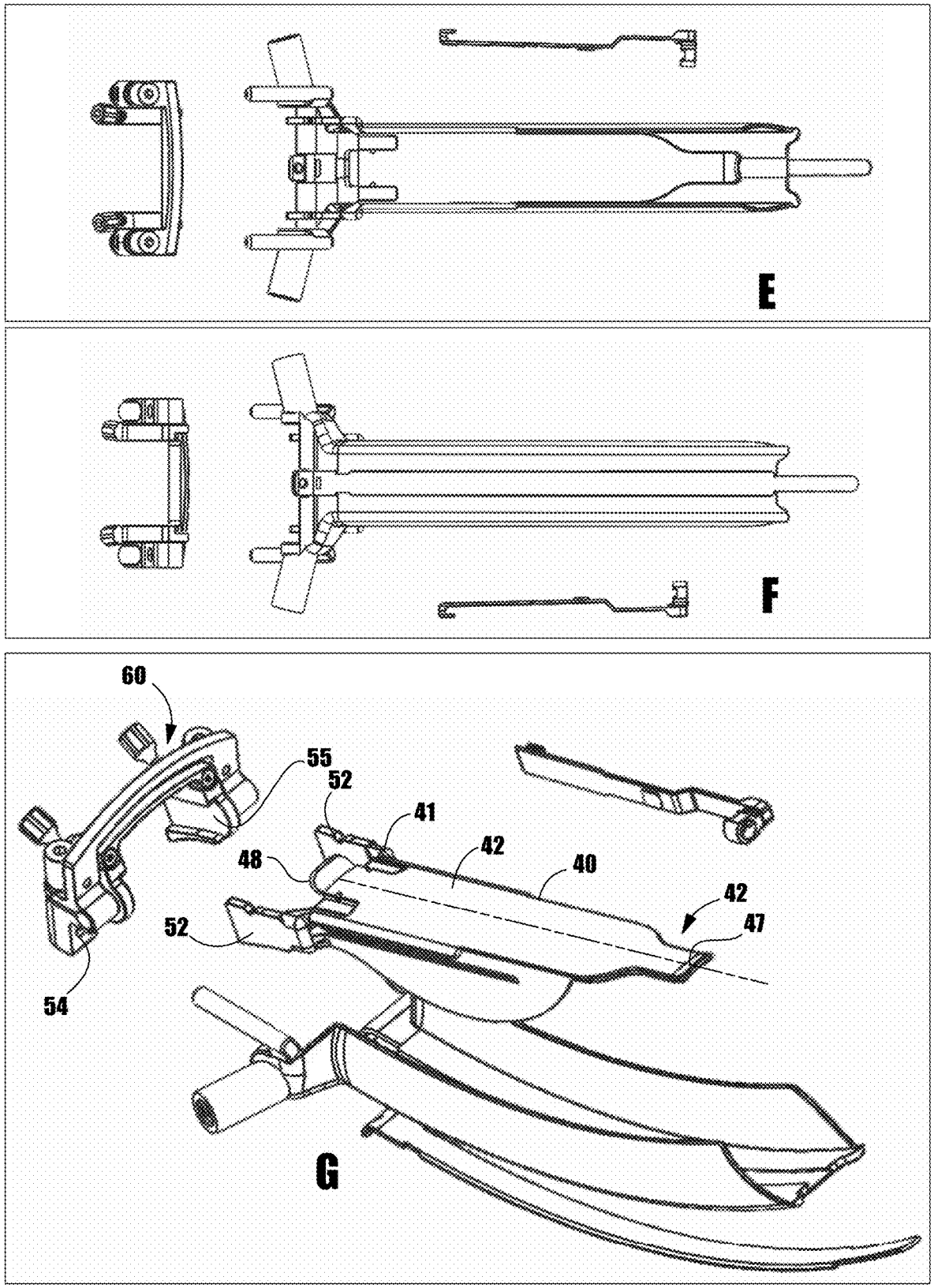
FIG. 7 includes in panels A, B, C, D, E, F and G, respectively, alternate exploded front, back, first and second side, top, bottom, and oblique views of a modular retractor in accordance with the disclosure.
Figure 8:
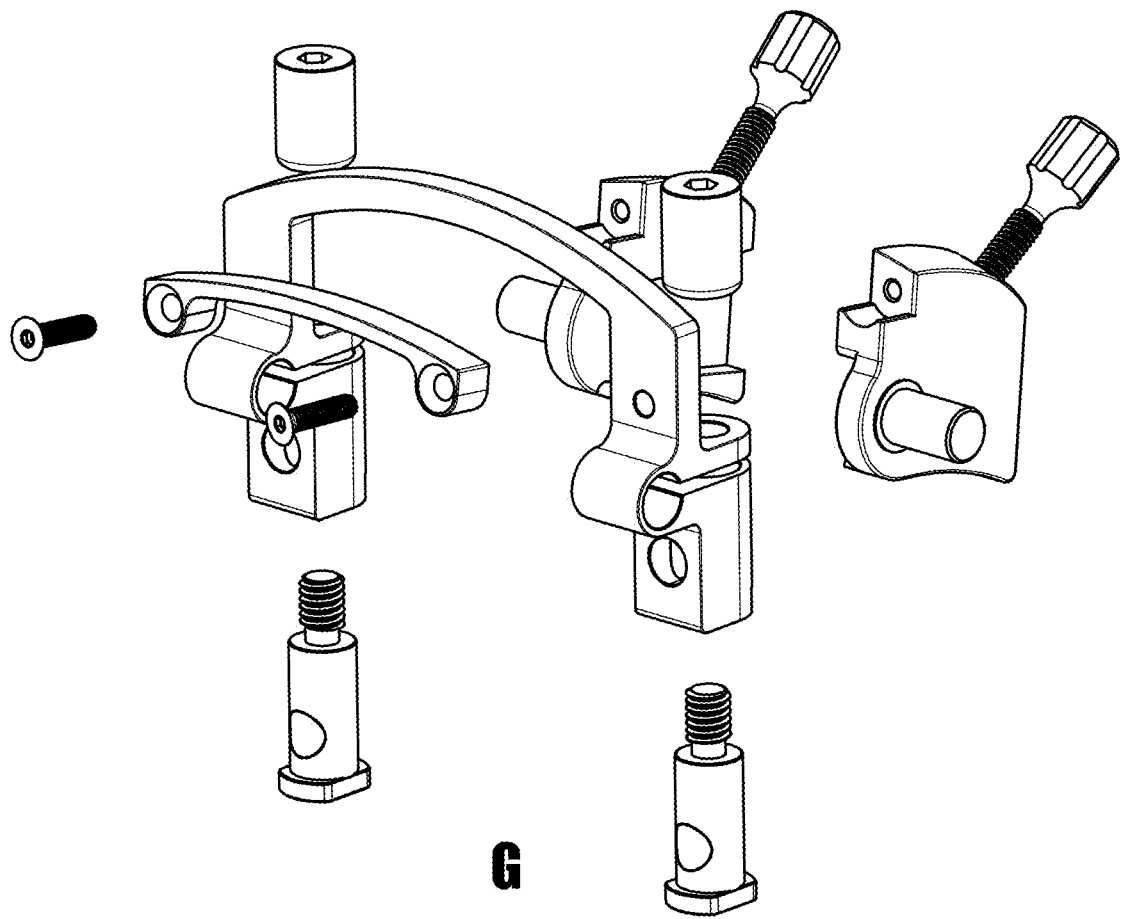
FIG. 8 includes in panels A, B, C, D, E, F and G, respectively, alternate exploded front, back, first and second side, top, bottom, and oblique views of a fastening yoke of a modular retractor in accordance with the disclosure.
Figure 9:
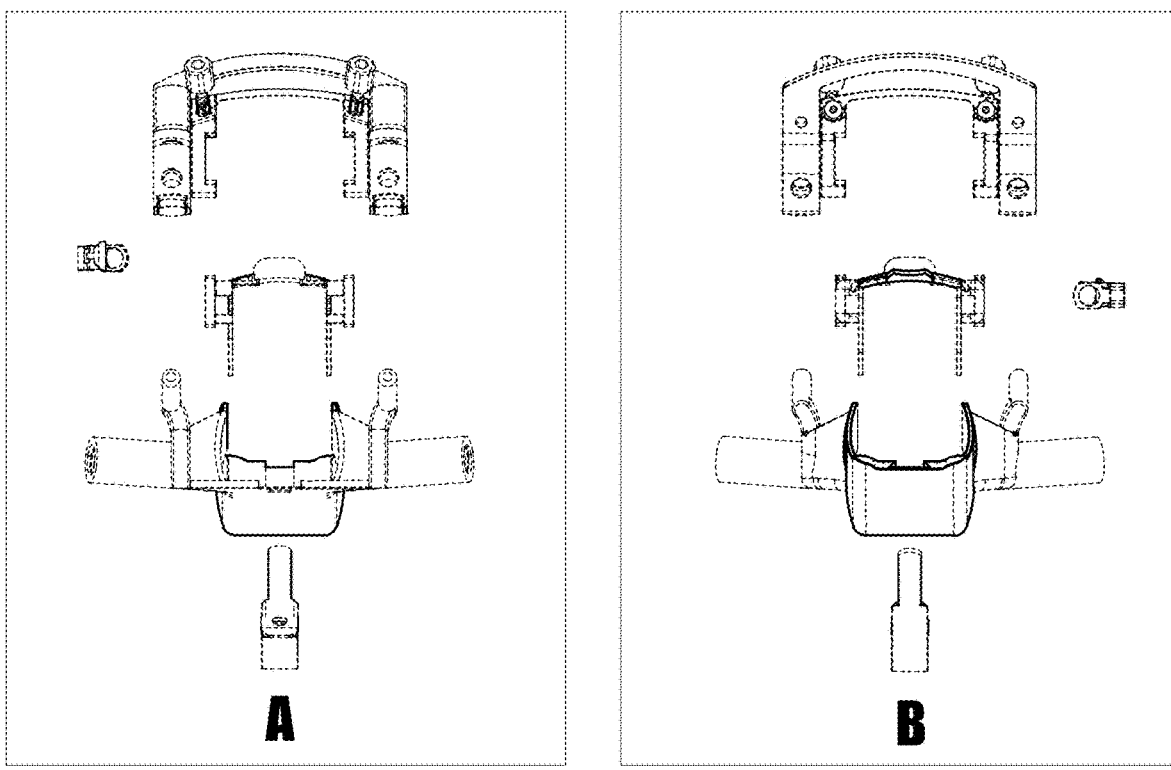
FIG. 9 includes in panels A, B, C, D, E, F and G, respectively, alternate exploded back, front, top, bottom, first and second side, and oblique views of an alternate embodiment of an modular retractor in accordance with the disclosure.
Figure 9:
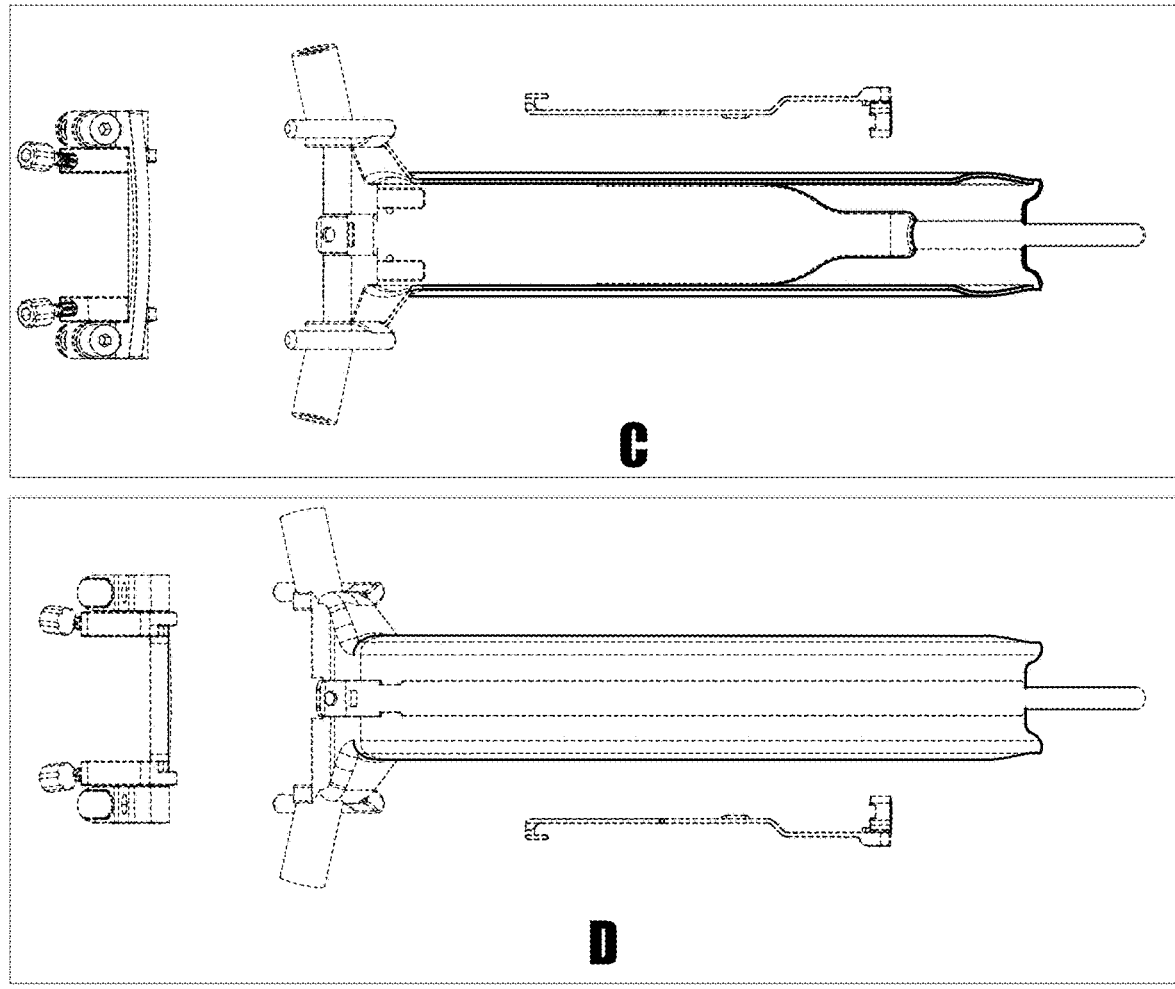
Figure 9:
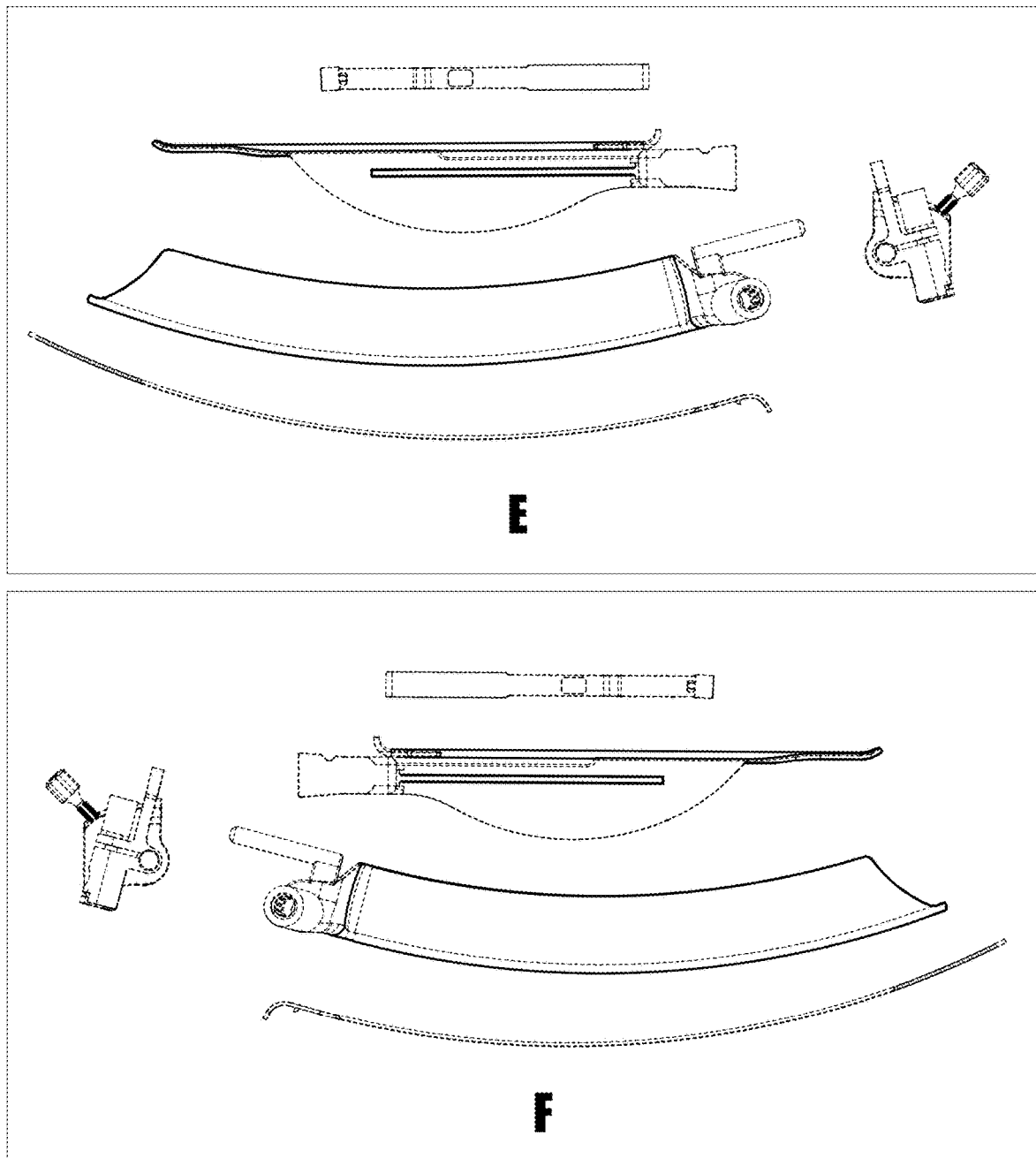
Figure 9:
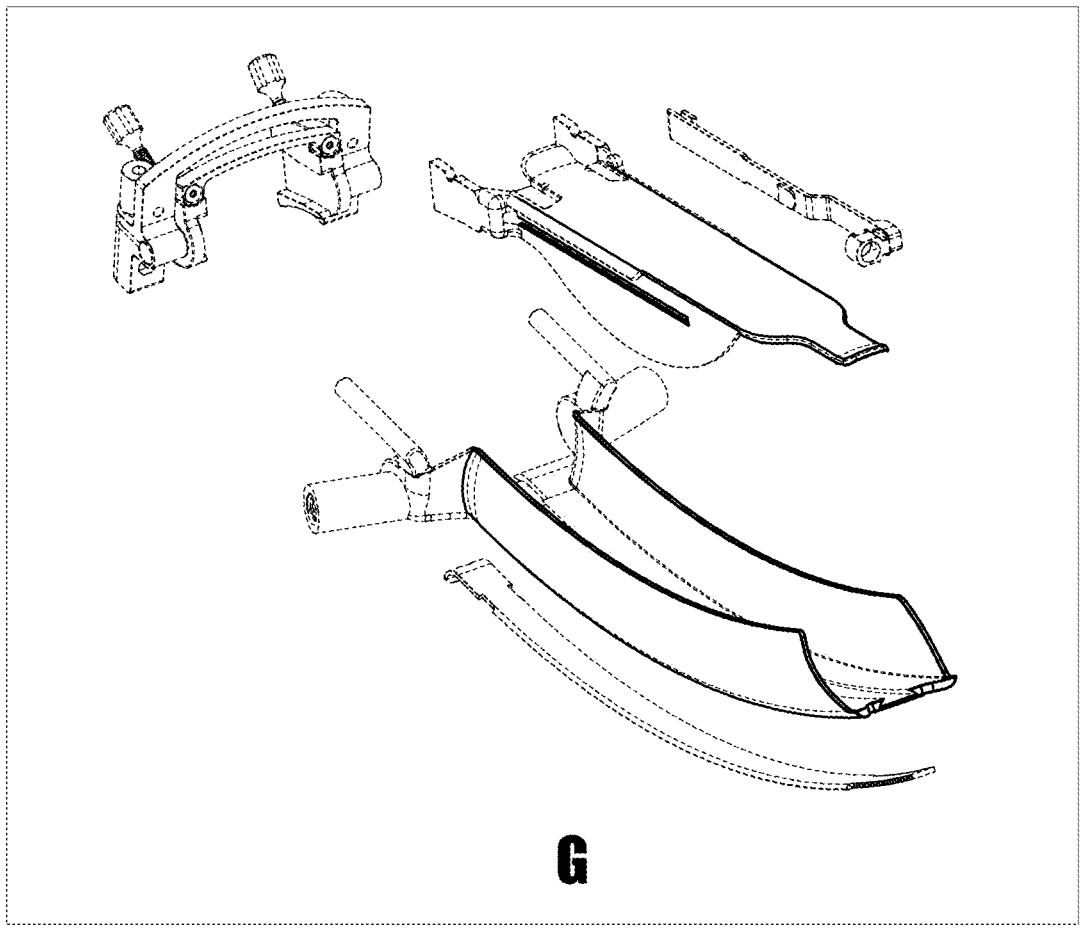
Figure 10:
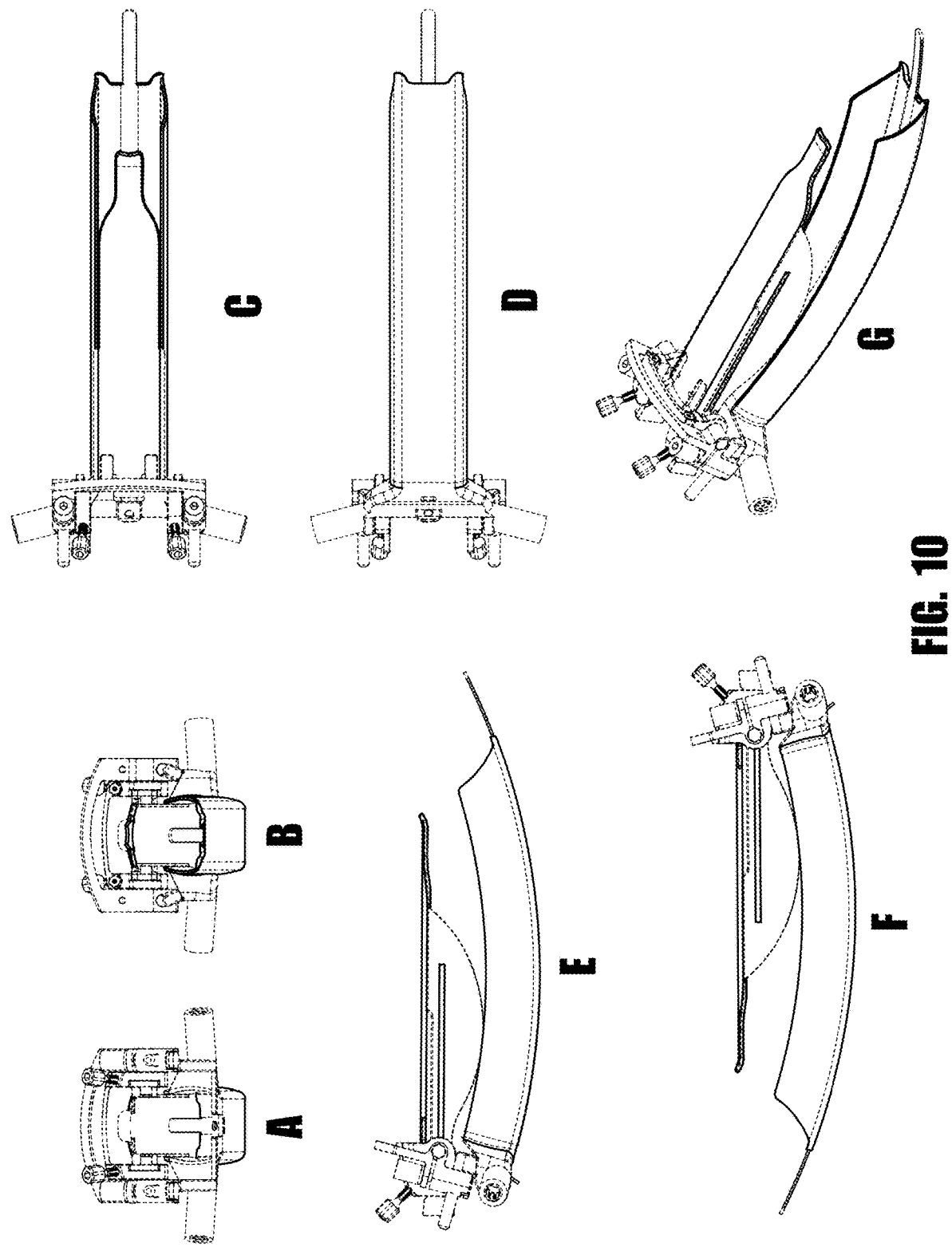
FIG. 10 includes in panels A, B, C, D, E, F and G, respectively, alternate back, front, top, bottom, first and second side, and oblique views of an alternate embodiment of a modular retractor in an open position in accordance with the disclosure.
Figure 11:
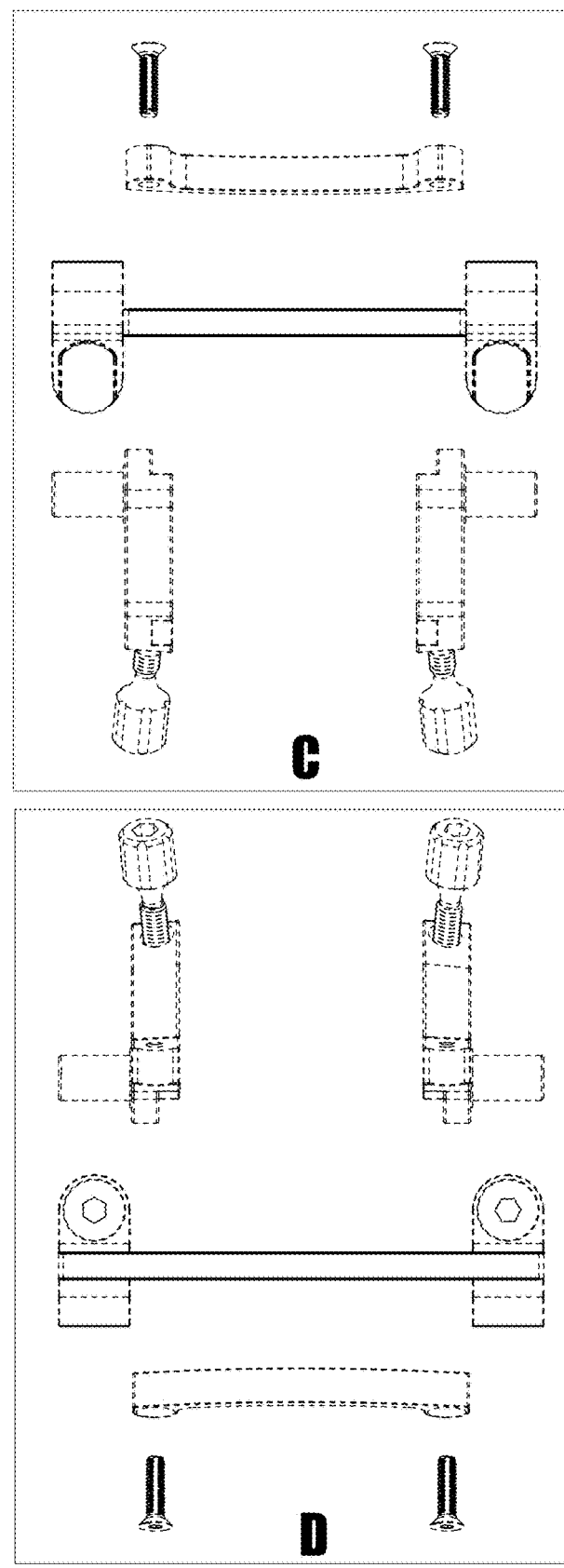
FIG. 11 includes in panels A, B, C, D, E, F and G, respectively, alternate exploded back, front, top, bottom, first and second side, and oblique views of an embodiment of an alternate embodiment of a fastening yoke of a modular retractor in accordance with the disclosure.
Figure 11:
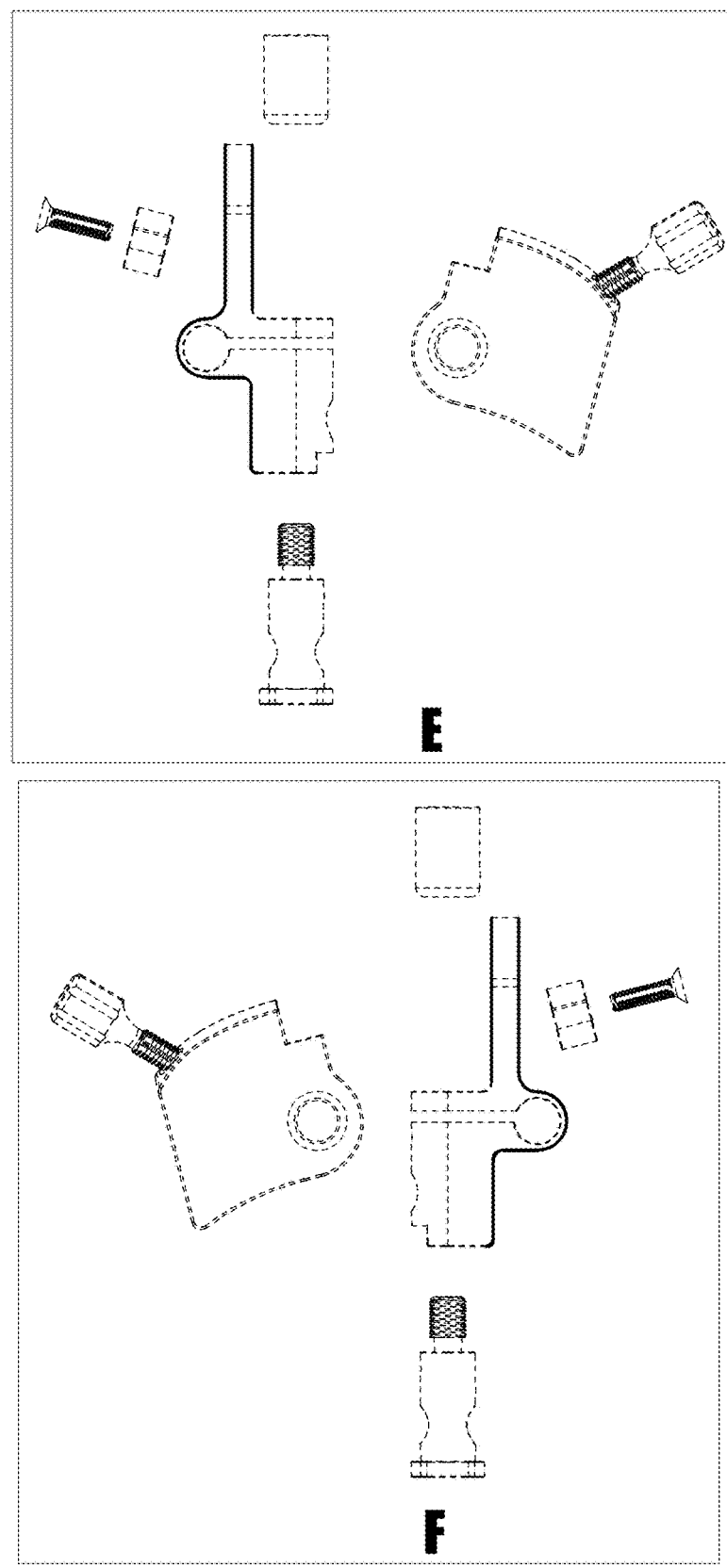
Figure 11:
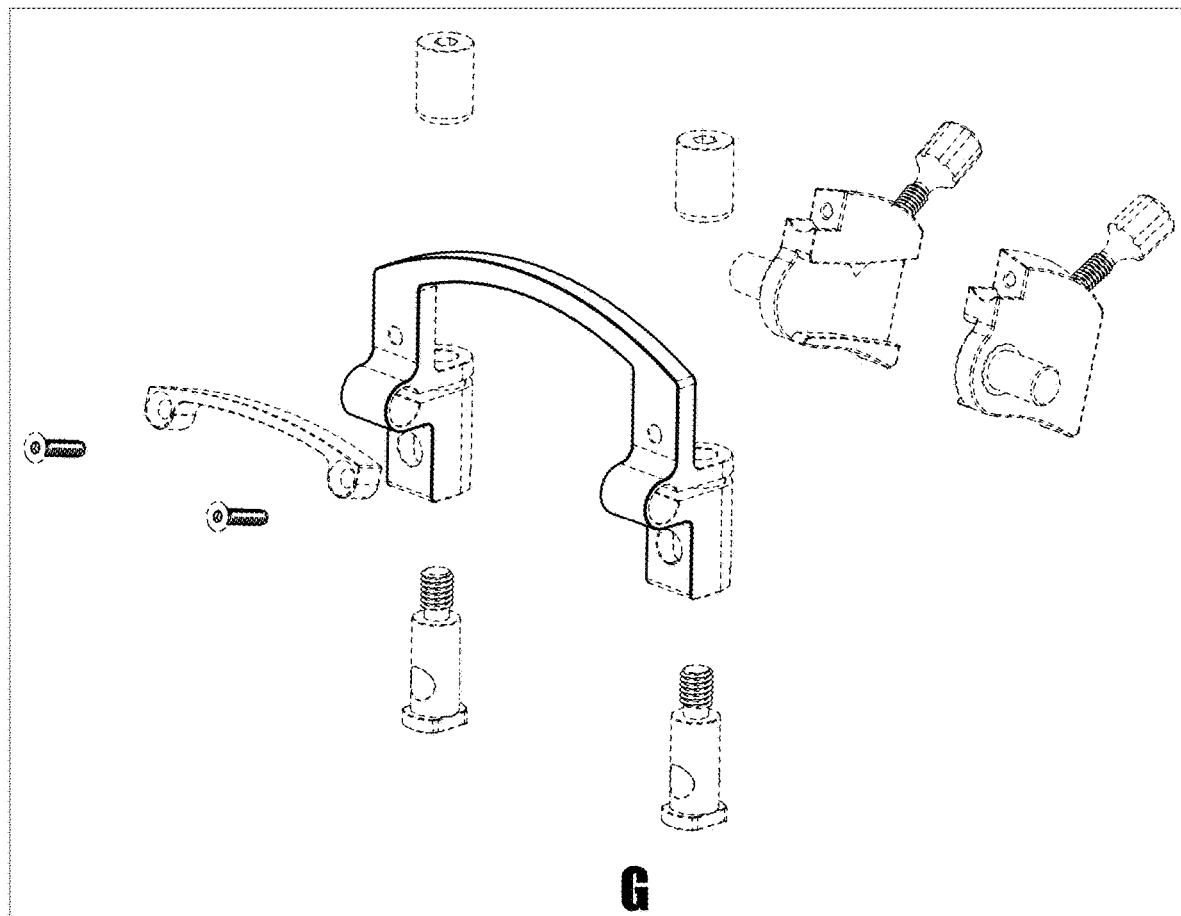

Referring again to the drawings, FIG. 8, for example, shows an embodiment of an coupling system engageable with exemplary coupling elements on the retractor body and hood, shown, for example, in FIG. 7. Referring again to FIG. 7, the depicted embodiment of the retractor includes a pair of opposing proximally extending pins on the left and right sides at the proximal end of the retractor body, and a pair of opposing proximally extending tabs on the proximal end of the hood, each of which pairs of pins and tabs respectively engage with the yoke component coupling system shown in FIG. 8.

In various embodiments, the direct visualization retractor system has external dimensions that are suited for insertion through an incision in a patient's skin and passage to an internal target tissue site, and internal channel dimensions that are suited for the passage there-through of instruments and implants for use on the target tissue. In various embodiments, it may be desirable for each of the retractor body and hood components to have the same length, and in yet other embodiments, it may be desirable for the hood to be longer or shorter than the retractor body. In one example, the hood may be shorter than the retractor body for certain spinal surgery applications, where the posterior bony structures of the spine would interfere with the distal end of the hood. In yet other examples, one or more of the radius of the system components and the particular patient anatomy may necessitate selection of a hood that is longer than the retractor body in order to ensure good engagement at the proximal end and suitable contact with the target tissue at the distal and of the hood.

Referring again to FIG. 4, examples of varied length hood and retractor body components are shown nested in a schematic that illustrates some options for relative hood and retractor body length. It will be appreciated by one of ordinary skill that the absolute dimensions of the retractor components may be varied to accommodate the dimensions of the body parts and tissue being targeted, and that any specific dimensions shown or described herein are not limiting.

The retractor and the hood are specifically adapted to be independently guided and inserted, in series, into an incision in the patient's skin to allow for manipulation and retraction of soft tissue, and can be coupled in situ to form the direct visualization retractor system. In use, the retractor is useful for supplementing tissue dilation and distraction, and for establishing the channel through which the target tissue will be surgically accessed. Each of the retractor and hood components has a width dimension that is generally perpendicular to and runs substantially along the collinear longitudinal axes. In some embodiments, the width of the hood is less than the width of the retractor, such that the hood can be retractor support at least partially recessed within the chute of the retractor before coupling to form the retractor system.

In various embodiments, the distal end of one or both the retractor body and retractor hood is contoured and the contour describes a concave arc that transects the retractor's longitudinal axis and has a radius of curvature from about 0.5 cm to 10 cm. In some embodiments, the contour is bounded by bosses. Referring again to the drawings, FIG. 7F, for example, shows the distal end of the retractor body having a curve that is bounded by bosses. These features enhance the engagement of the retractor with the spine and stabilize it during use. FIG. 7F likewise shows a modest radius on the distal tip of the hood retractor. In addition, the hood retractor, as shown, has a tissue elevator at the distal end that is recessed (curved or dipped) relative to an external surface of the hood, and has a width dimension that is less than a width dimension of the proximal end of the hood. Thus, in various embodiments, a contour at a retractor distal end may have a radius in cm and increments in between including 0.5, 1, 2, 3, 4, 5, 6, 7, 8, 9, 10 cm.

Figure 5:
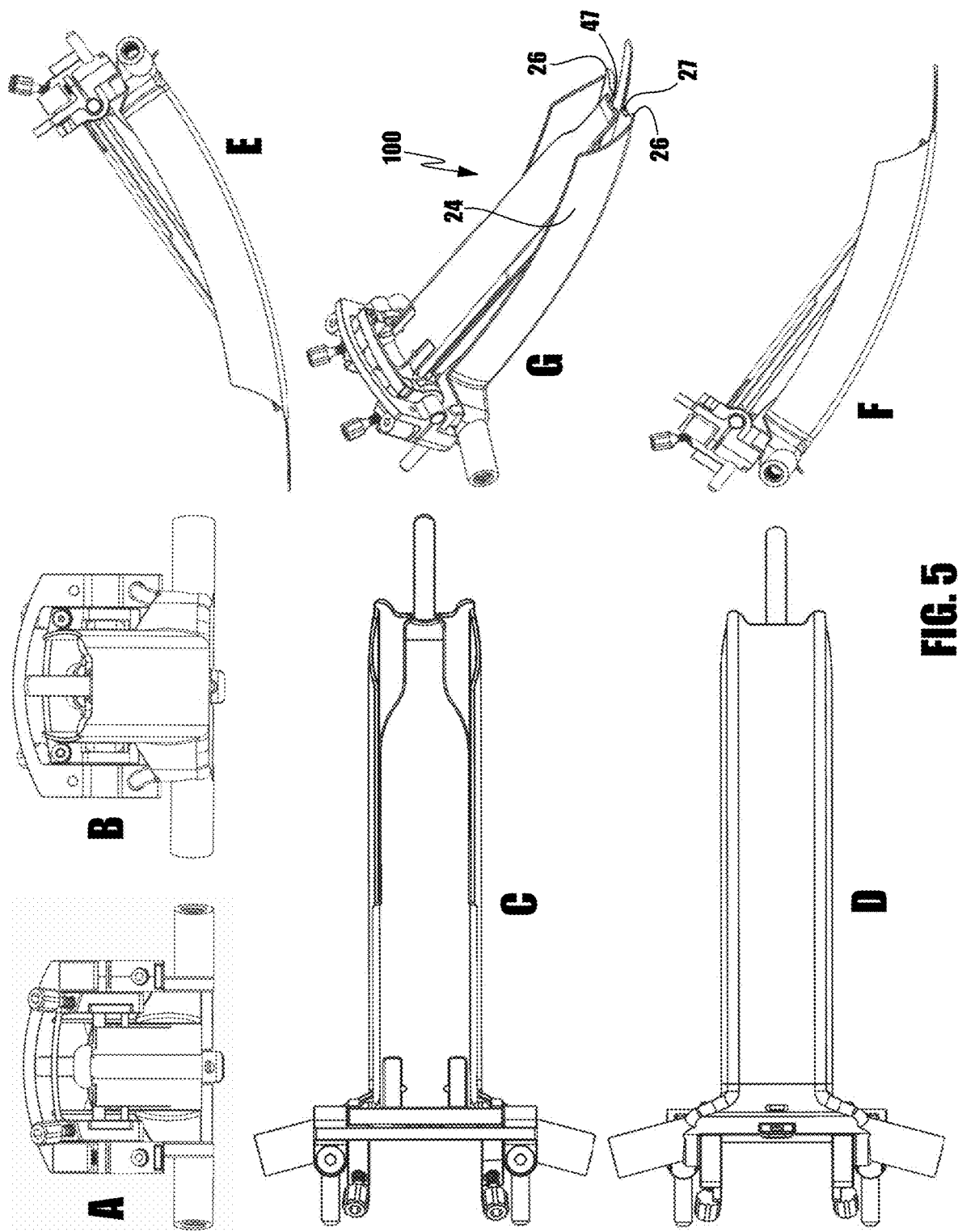
FIG. 5 includes in panels A, B, C, D, E, F and G, respectively, alternate back, front, top, bottom, first and second side, and oblique views of an assembled modular retractor in a closed position in accordance with the disclosure.
Figure 6:
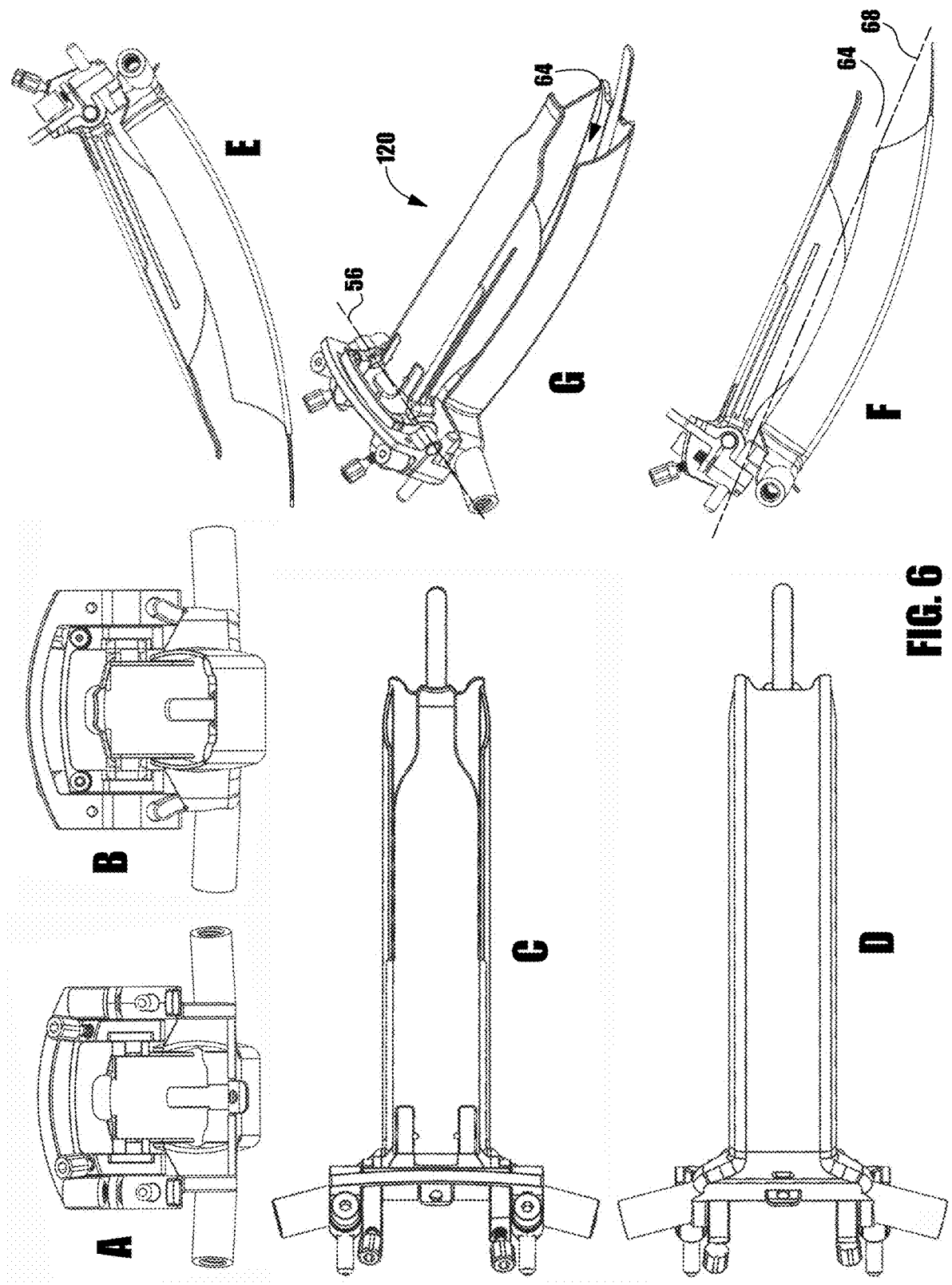
FIG. 6 includes in panels A, B, C, D, E, F and G, respectively, alternate back, front, top, bottom, first and second side, and oblique views of an assembled modular retractor in an open position in accordance with the disclosure.

The modular direct visualization retractor system is adjustable in a variety of modes to allow an unobstructed view of and access to the surgical site for manipulation of tissue and to accommodate passage of surgical instruments and implants. For example, in one mode of adjustment, the distance between the distal ends of the retractor and hood can be adjusted by rotation at the coupling, whereby the distal and proximal ends of the retractor system can be adjusted to have variably sized distal openings while the distance between them at the proximal end remains essentially fixed. Referring again to the drawings, FIG. 5 shows a representative embodiment wherein the assembled retractor system is in a closed configuration, with the distal end of the hood resting within and in contact with the retractor body. FIG. 6 shows the same representative embodiment wherein the assembled retractor is in an open configuration. In another mode of adjustment, the retractor and hood can be slidably translated along the collinear longitudinal axes so that the relative positions of the distal and proximal ends of the retractor and hood can be varied. And in yet another mode of adjustment, the relative vertical distance between the hood and the retractor can be adjusted.

Figure 37:
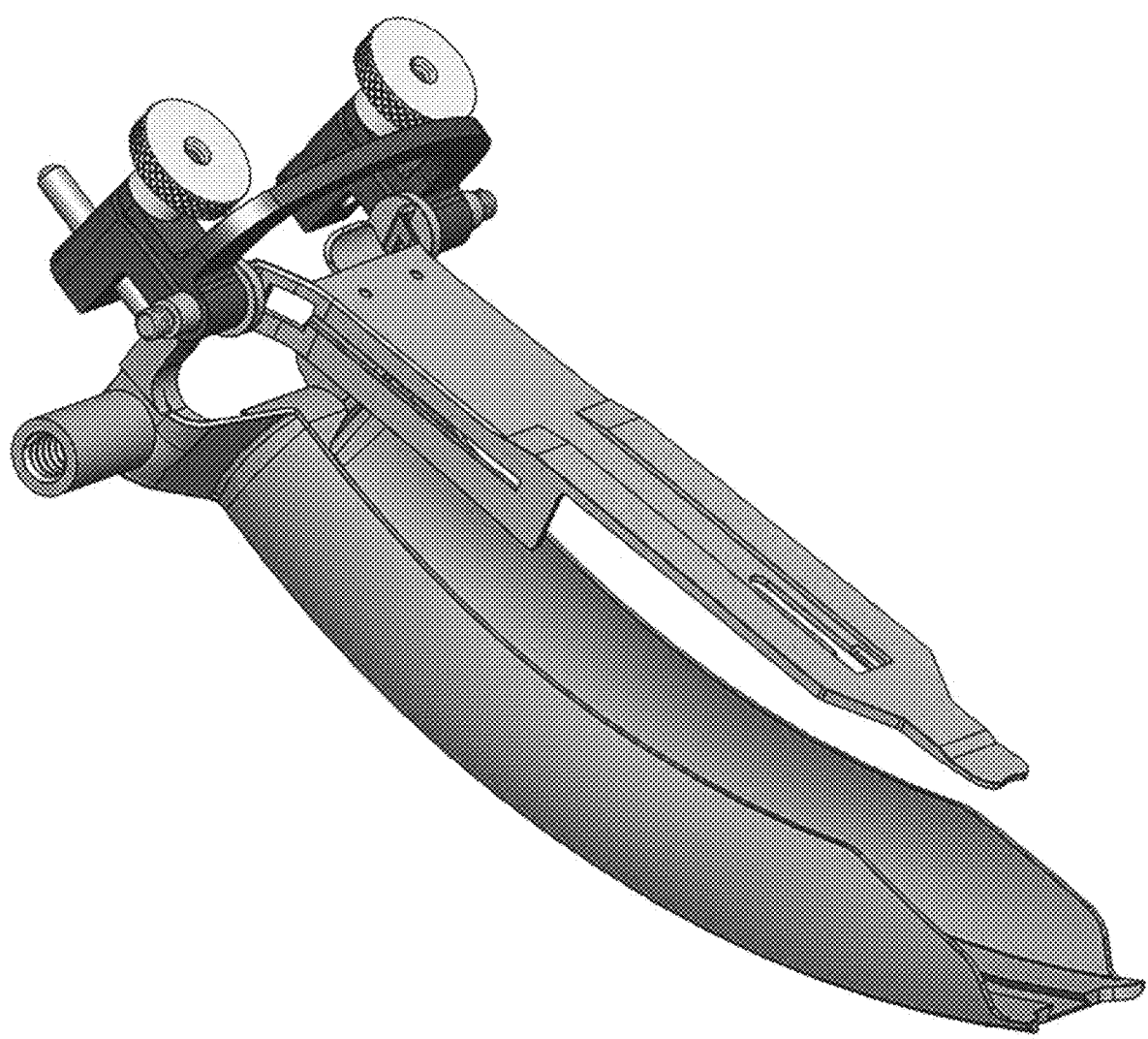
FIG. 37 is an oblique view of an alternate embodiment of an assembled modular retractor in accordance with the disclosure.
Figure 43:
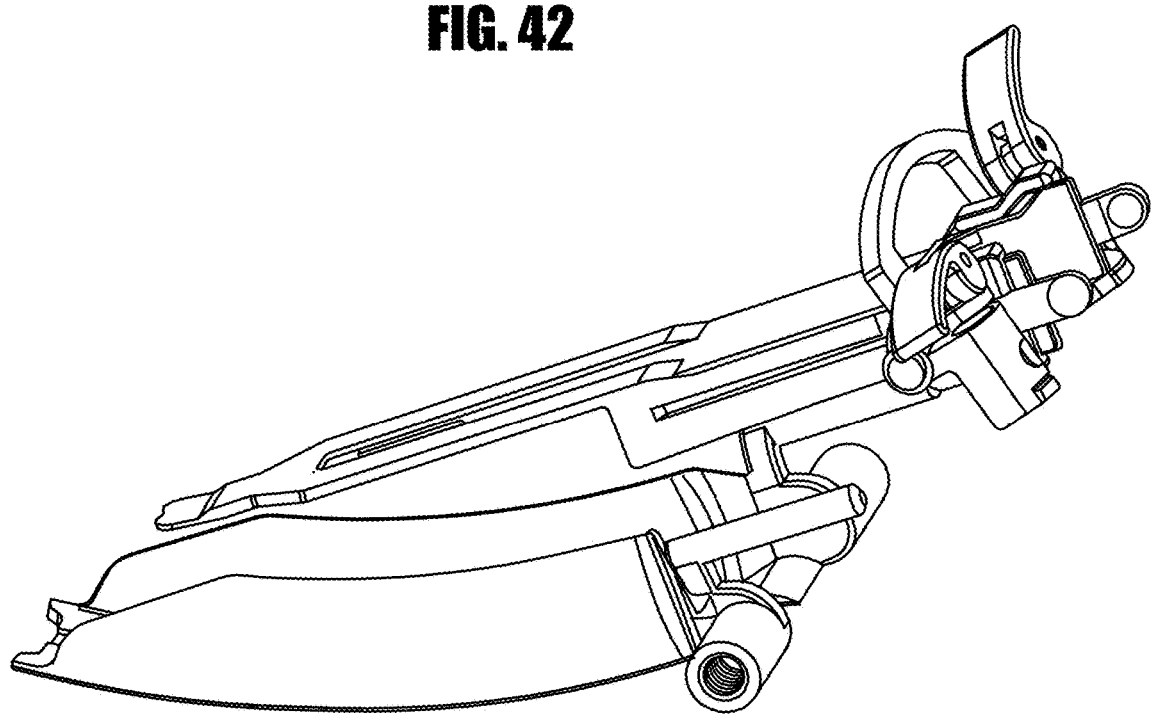

Examples of retractor devices having two modes of adjustment are shown FIG. 4, for example, and also in different embodiments shown in FIG. 37 and FIG. 43, wherein the hood may be rotated pivotally to raise and lower its distal end and it may be displaced laterally along its axis that is collinear with the retractor body.

Referring again to the drawings, FIG. 38 depicts a representative example of a retractor device wherein three modes of adjustability are enabled. Referring to the drawing, the hood can be raised or lowered from the retractor body by vertical adjustment of a lockable channel expander comprising a primary yoke on the retractor body handle that comprises opposing clips for slidable engagement with the hood, and wherein the hood may be rotated pivotally to raise and lower its distal end by actuation of the tabbed yoke on the hood. In addition, as shown in representative FIG. 38, the hood and retractor body may be displaced laterally along their collinear axes by translation of the hood within the G shaped clips at the top end of the yoke on the retractor body handle. In yet other embodiments, the retractor device may be adjustable only in one mode, for example, pivotal rotation at a proximal axis to adjust the distance between the distal ends of the hood and retractor body.

In the various disclosed embodiments, the modes of adjustability of the retractor components enable customized adjustment of the retractor system to accommodate one or more of positioning relative to the target tissue site, manipulation of tissue to minimize tissue creep within the channel, relief of compression of soft tissue, and adaptation of the channel for passage of varying sized instruments and implants.

In some embodiments, at least one of the retractor and hood also includes at least one tissue fixation member. A tissue fixation member is useful for firmly securing one or more of the retractor, the hood and the retractor system to tissue. A tissue fixation member includes a retractor system securement element that is securable to the surgical access retractor system, and a tissue securement element that is securable to the target tissue site. In various embodiments, the tissue securement element is selected from a screw, a pin, a wire, an awl, and a tang, and other implements that can be removably affixed to tissue, particularly bone.

In some representative embodiments, the retractor includes as a tissue fixation member an elongate tang that is oriented along the longitudinal axis and is adjacent to the retractor floor and extends beyond the distal end. Referring now to exemplary FIG. 6G and FIG. 7G, the tang is slidable within a receiving slot in the floor of the retractor body and extends therefrom for insertion into the target tissue. In use, the tang may be assembled with the retractor body on its insertion adjacent to the target tissue, or may be slid into place after the retractor body is positioned on the tissue, the end of the tang being extended at a preferred distance from the retractor body distal end.

Figure 13:
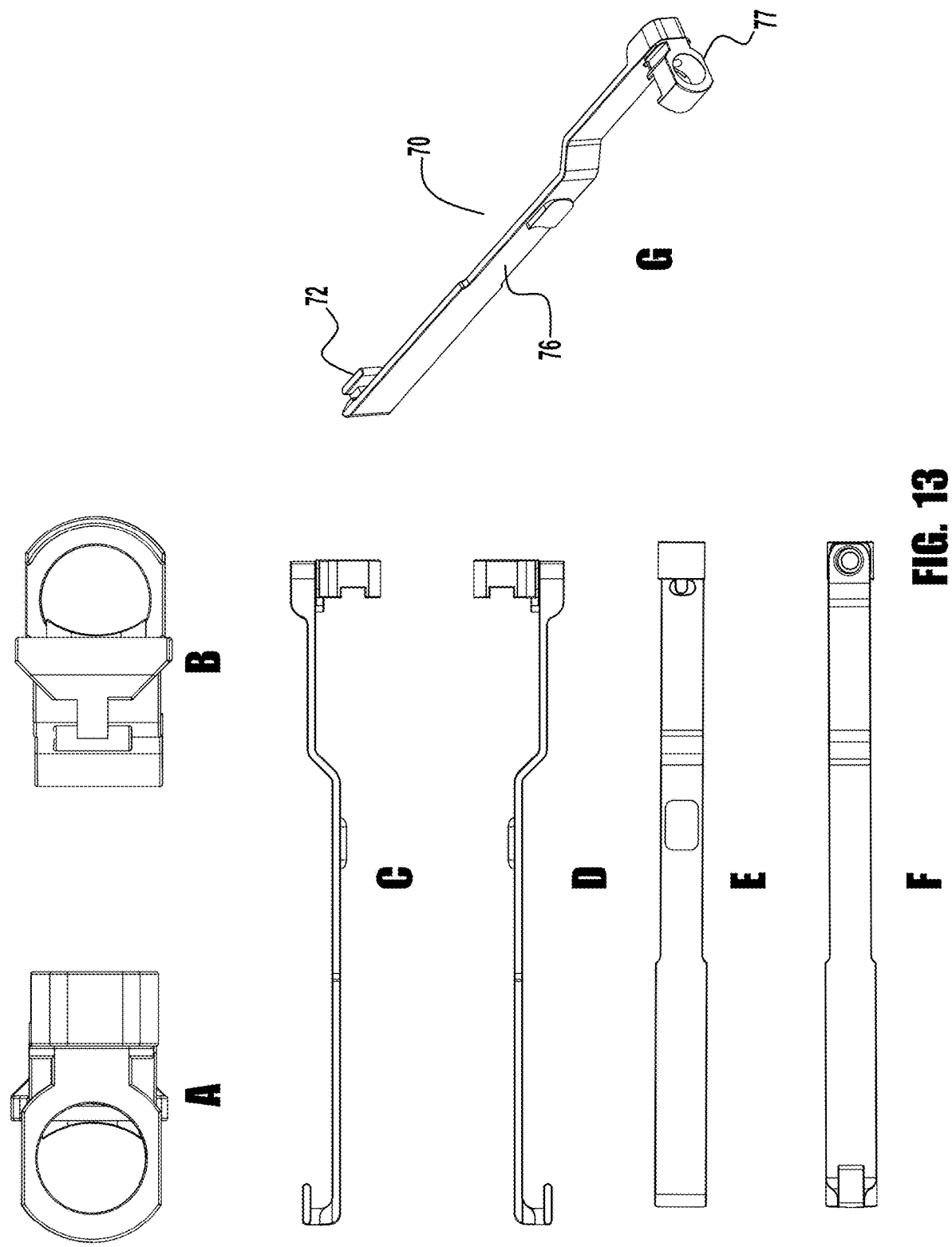
FIG. 13 includes in panels A, B, C, D, E, F and G, respectively, alternate back, front, top, bottom, first and second side, and oblique views of an embodiment of a fixation tissue securement guide for engagement with a modular retractor in accordance with the disclosure.

In other embodiments, the securement element is a screw, the device further comprising a screw placement guide securable to either the hood or the body, and a driver engageable with the guide. Referring again to the drawings, FIG. 13 shows an exemplary embodiment of a tissue fixation member comprising a retractor securement element in the form of a screw placement guide comprising an elongated arm that is securable to a receiving channel on an extended sidewall of the depicted hood, the elongated arm comprising at a proximal end a tab that engages with the hood receiving channel, and at its distal end a locking ring for securing a driver for delivering the pin or screw to the tissue and for engaging a pin or screw (not shown) passed there though and affixed to the target tissue. FIG. 7 shows the exemplary tissue fixation member in the context of an exploded depiction of an embodiment of the retractor device. Of course, it will be appreciated by one of ordinary skill in the art that the exemplary tissue fixation member may be varied in its attachment to one or the other of the retractor hood and retractor body, and may likewise have a different engagement with the pin or screw.

Figure 14:
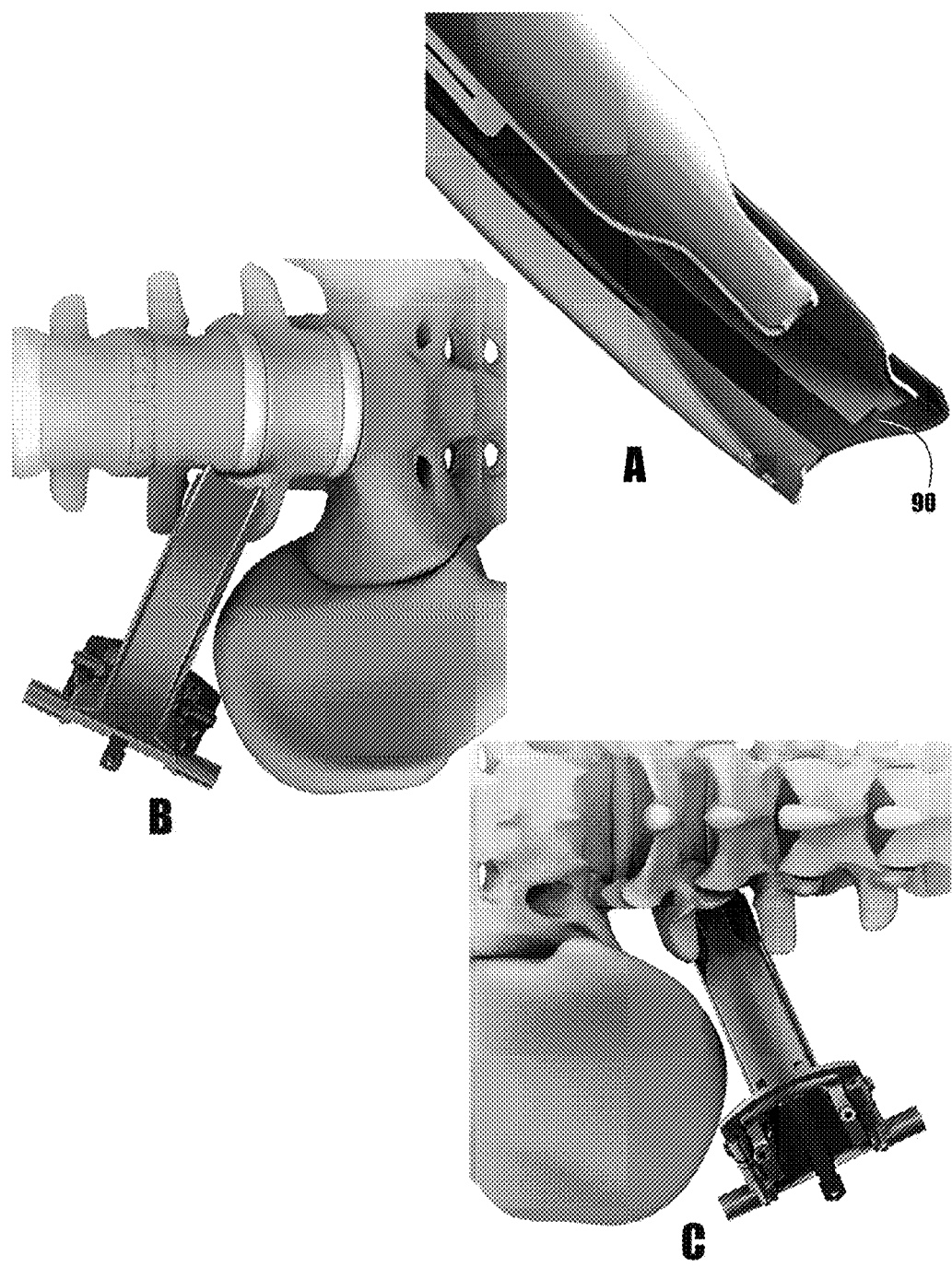
FIG. 14 includes in panel A a schematic of a distal/front end of a modular retractor in a partially closed position in accordance with the disclosure including a slidable retractor blade for optimizing positioning; and in panel B a modular retractor of panel A depicted in the context of a portion of a human spine and adjacent to the L4/L5 disc interface from an anterior perspective; and in panel C same modular retractor depicted in the context of a portion of a human spine and adjacent to the L4/L5 disc interface from an posterior perspective, and in panels D, E, F, G, H, I and J, respectively, alternate left and right back, left and right front, left and right top, left and right bottom, left and right left side, left and right side, and left and right oblique views of an embodiment of a slidable retractor blade for a modular retractor in accordance with the disclosure.
Figure 14:
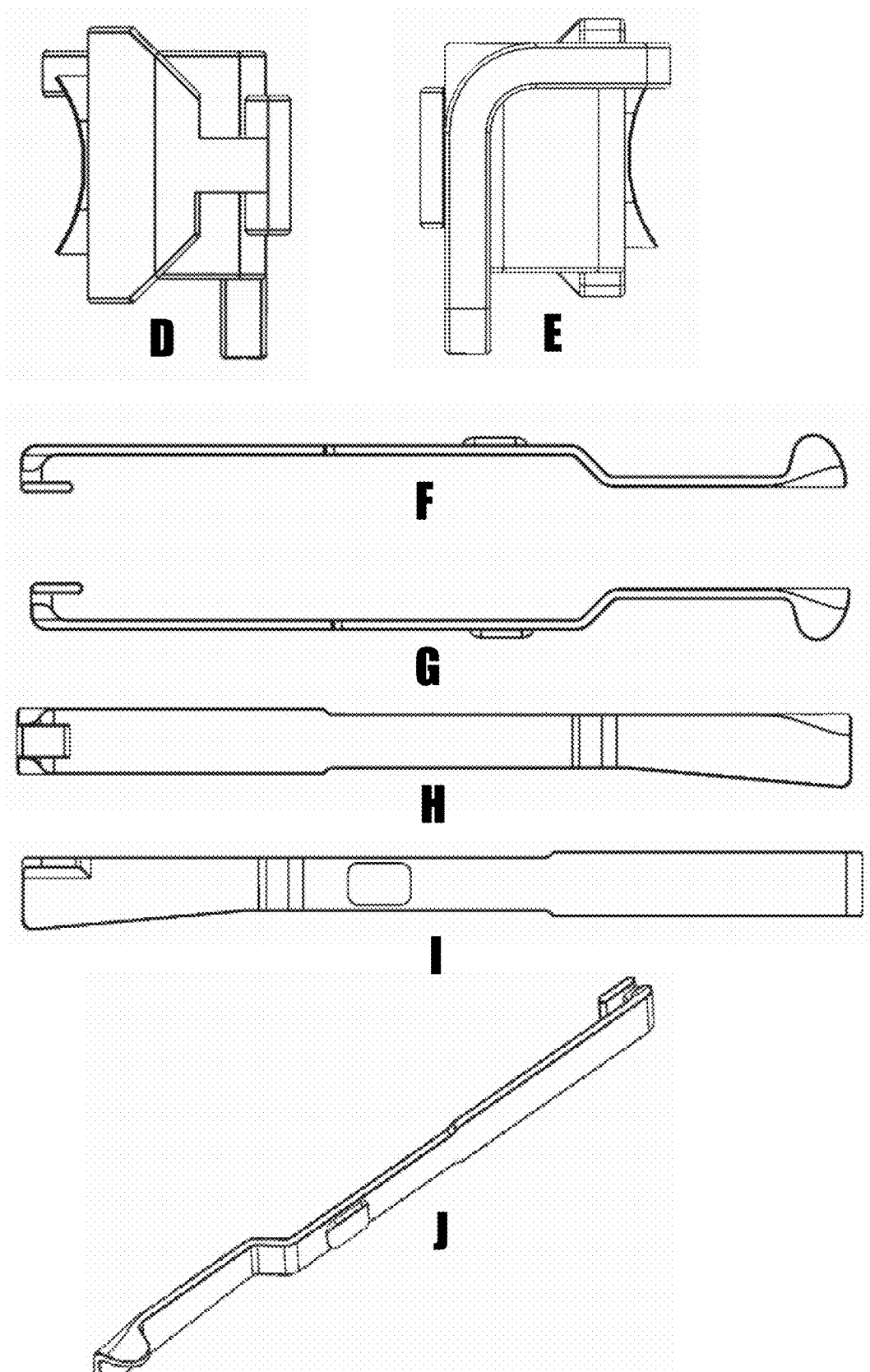

In some embodiments, the retractor device includes an adapter for enhancing contact with the target tissue. For example, a shim or other adapter may be used to accommodate gaps between the distal end of the retractor body where anatomical structures such as bone spurs impede optimal contact of the end of the retractor with the tissue or the anatomy otherwise interferes such as the hip bones interference with access to the L4/L5 disc. Referring again to the drawings, FIG. 14 includes, in panel A, a schematic of a distal/front end of a modular retractor in a partially closed position in accordance with the disclosure including a slidable retractor blade for optimizing positioning. FIG. 14 panel B shows a modular retractor of panel A depicted in the context of a portion of a human spine and adjacent to the L4/L5 disc interface from an anterior perspective, and panel C shows the same modular retractor depicted in the context of a portion of a human spine and adjacent to the L4/L5 disc interface from an posterior perspective. More detailed views of the retractor are shown in the additional panels of FIG. 14.

Of course, a wide range of possible combinations of retractor components is available in accordance with the disclosure, and may be selected from the specific embodiments of arrays as disclosed herein and from embodiments that are within the scope of the disclosure though not specifically described in the specification and drawings.

Thus, in various embodiments according to the disclosure, there is provided a medical device for performing surgery at a surgical field within a body, the medical device comprising a modular surgical retractor comprising, a retractor body and a retractor hood, the retractor body and retractor hood each comprising a proximal end that is adapted to extend outside of the surgical field and a distal end that is adapted to extend into the surgical field, the body and hood engageable to form a through channel disposed between open proximal and distal ends bounded by the body and retractor hoods, the through channel having a central channel axis and the retractor body comprising a floor extending along a retractor body longitudinal axis, and the retractor hood comprising a body extending along a retractor hood longitudinal axis, the retractor hood having a soft tissue elevator at the distal end, and a releasable handle at the proximal end.

According to some such embodiments, each of the retractor body and retractor hood are independently operable to manipulate soft tissue and adapted to be adjustably and releasably coupled at their proximal ends with general alignment of their respective longitudinal axes, the retractor body and the retractor hood each comprising at its proximal end a coupling element for adjustably and releasably coupling the body and hood, one of the coupling elements comprising one or a plurality of fasteners, and the other of the coupling elements comprising one or a plurality of receivers. When uncoupled, the retractor hood can be aligned with the retractor body and at least partially compressed against the retractor body, and when coupled, the retractor body and retractor hood are displaced from one another vertically and constrained to one or more of three degrees of freedom, being movable pivotally around a pivot axis at the proximal end that is essentially perpendicular to the channel longitudinal axis, displaceable vertically from between a compressed orientation up to a pre-selected displacement distance, or slidable horizontally along the channel longitudinal axis, or combinations of these.

In various embodiments, the retractor body is either rectilinear or curvilinear along its longitudinal axis.

In various embodiments, the retractor body is substantially curvilinear along its longitudinal axis and has a radius of curvature from about 5 to 50 cm. In various embodiments, the distal end of one or both the retractor body and retractor hood is contoured and wherein the contour describes a concave arc that transects the retractor's longitudinal axis and has a radius of curvature from about 0.5 cm to 10 cm, and wherein the contour is bounded by bosses.

In various embodiments, each of the retractor body has a length dimension that is greater than, equal to, or smaller than the length dimension of the retractor hood.

In various embodiments, the retractor hood is rectilinear along its longitudinal axis, and is either rectilinear or bowed around its longitudinal axis along at least a portion of its length.

In various embodiments, the soft tissue elevator at the distal end of the retractor hood is either or both recessed relative to an external surface of the hood, and has a width dimension that is less than a width dimension of the proximal end of the hood.

In various embodiments, the retractor body comprises two opposing sidewalls bounding the floor along at least part of the length of the floor, the floor and sidewalls extending along the longitudinal axis and defining a chute with an open top, wherein the retractor body sidewalls are selected from essentially planar and bowed. In some such embodiments, the retractor body sidewalls extend along the longitudinal axis from the proximal end of the retractor body and terminate proximal to the distal end of the retractor body. In some such embodiments, the sidewalls extend less than half a length dimension of the retractor body.

In various embodiments each of the retractor body and the retractor hood has a width dimension that is generally perpendicular to and runs substantially along its longitudinal axis; and wherein the width of at least the distal portion of the retractor hood is less than the width of the retractor body such that the retractor hood can be at least partially recessed within the chute of the retractor body. In some such embodiments, the width of the retractor hood from its proximal to its distal end is less than a narrowest width of the retractor body such that the retractor hood can be fully recessed within the chute of the retractor body and compressed against the retractor body floor.

In various embodiments, the retractor hood comprises hood sidewalls extending along the longitudinal axis at least part of a length of the hood, and wherein the retractor hood has an external height dimension that is bounded by an exterior surface of the retractor hood and a hood sidewall edge. In some such embodiments, the hood sidewalls extend along the longitudinal axis from the proximal end of the retractor hood and terminate proximal to the distal end of the retractor hood. In some such embodiments, the hood sidewalls extend less than half the length dimension of the hood.

In various embodiments, the one or more coupling element fasteners is a pin oriented along the pivot axis at the proximal end of the retractor hood and the one or more coupling element receivers is an slot oriented in parallel with the common longitudinal axis, the pin(s) slidably engageable in the slot(s) to couple the hood and the retractor. In some such embodiments, the coupling element fasteners comprise a pair of pins on the retractor hood and wherein the coupling element receivers comprise a pair of slots on the retractor body, each slot comprising a slot opening and a slot seat.

In some embodiments, each of the hood and the body comprise coupling element fasteners and each engages with a yoke component comprising receivers for each of the hood and body fasteners, such that each of the body, yoke and hood components may be assembled sequentially, or the body and yoke may be preassembled and receive the hood, or the hood and yoke may be preassembled for attachment to the body. In some such embodiments, the yoke comprises receiver channels for pin fasteners on the retractor body and receiver slots for tab fasteners on the hood body, and wherein the receiver channels slots are lockable and releasable, and wherein the yoke comprises a secondary yoke, and wherein when coupled, the proximal ends of the retractor body and retractor hood are displaced from one another vertically, and wherein the receiver channels and pin fastener are engageable to allow for slidable horizontally adjustment of the hood position relative to the body along the channel longitudinal axis, and wherein the secondary yoke allows for adjustment of the retractor hood around a pivot axis at the proximal end that is essentially perpendicular to the channel longitudinal axis to enable vertical displacement of the distal end of the hood from the distal end of the body.

In various embodiments, at least one of the retractor and the hood comprises at least one tissue fixation member, comprising a retractor securement element and a tissue securement element, the retractor securement element securable to one or both of the retractor body and retractor hood, and the tissue securement element securable to a target tissue in the surgical field and selected from a screw, a pin, a wire, an awl, and a tang.

In some embodiments, the securement element is a tang having a proximal and a distal end and is slidable within a channel in the floor of the retractor body, the tang comprising one or both a grasping tab at its proximal end and a serrated blade that is either curved or pointed at its distal end, the length of the tang being selected from a plurality of tang lengths.

In other such embodiments, the securement element is a screw, the device further comprising a screw placement guide securable to either the hood or the body, and a driver engageable with the guide.

In some embodiments, the medical device comprises a lockable channel expander for adjusting the proximal end vertical displacement of the retractor hood from the open top of the retractor body when the retractor hood and retractor body are coupled.

In various embodiments of the medical device one or both the retractor body and retractor hood comprises at its proximal end a handle feature selected from a fixed and a releasable handle, and wherein the handle is oriented relative to the retractor at an angle that is between 5 and 90 degrees, and wherein the retractor body comprises at its proximal end one or more of a light source attachment, a scope attachment, and at least one support bracket adapter for attachment to a support bracket fixture that is remote from the surgical field.

In some embodiments, the medical device comprises a distal retractor shim, the shim comprising an elongate shim extender, a proximal grip and a distal shim element having a retractor hood contact surface and a retractor body contact surface, the distance between which surfaces establishes a shim height.

In some specific embodiments according to the disclosure, there is provided a medical device for performing minimally invasive surgery in a surgical field, comprising a modular surgical portal comprising, a retractor body and a retractor hood, each of the body and hood having a proximal end that is adapted to extend outside of a surgical field and a distal end that is adapted to extend into the surgical field, and each of the body and hood being independently operable to manipulate soft tissue and adapted to be adjustably and releasably coupled at their proximal ends in a generally parallel orientation along respective longitudinal axes to form an elongate through channel disposed between open proximal and distal ends of the portal, the through channel having a central portal channel axis. According to some such embodiments, the elongate retractor comprises a floor and two opposing sidewalls that extend along a longitudinal axis and define a chute with an open top, and the retractor hood comprises, a body extending along a longitudinal axis, and a soft tissue elevator at the distal end, and a guide handle at the proximal end.

According to some such embodiments, each of the retractor and hood comprising a width dimension that is generally perpendicular to its longitudinal axis, the width of the hood being less than the width of the retractor such that the hood can be at least partially recessed within the chute of the retractor when they are aligned along the channel longitudinal axis. According to some such embodiments, at least the retractor body is curvilinear and has a radius of curvature of about 5 cm to about 25 cm.

According to some such embodiments, each of the retractor and hood comprises at its proximal end a coupling element, one of the coupling elements on the retractor and hood comprising one or a plurality of fasteners, and the other of the coupling elements on the retractor and the hood comprising one or a plurality of receivers, the portal comprising a channel expander for adjusting displacement of the hood from the open top of the retractor when the retractor and hood are coupled to form the portal.

According to some such embodiments, when coupled, one or both the retractor and hood can be articulated pivotally at the proximal end of the portal around a pivot axis that is essentially perpendicular to the common longitudinal axis. According to some such embodiments, one or both the retractor and hood can be slidably displaced along a path that is essentially parallel with the common longitudinal axis, and the through channel can be expanded or contracted by actuating the channel expander to achieve displacement of the hood from the retractor.

According to some such embodiments, at least one of the retractor and the hood comprises at least one tissue fixation member, comprising a portal securement element and a tissue securement element, the portal securement element securable to the surgical access portal, and the tissue securement element securable to the target tissue site and selected from a screw, a pin, a wire, an awl, and a tang.

Incision Guidance

Figure 15:
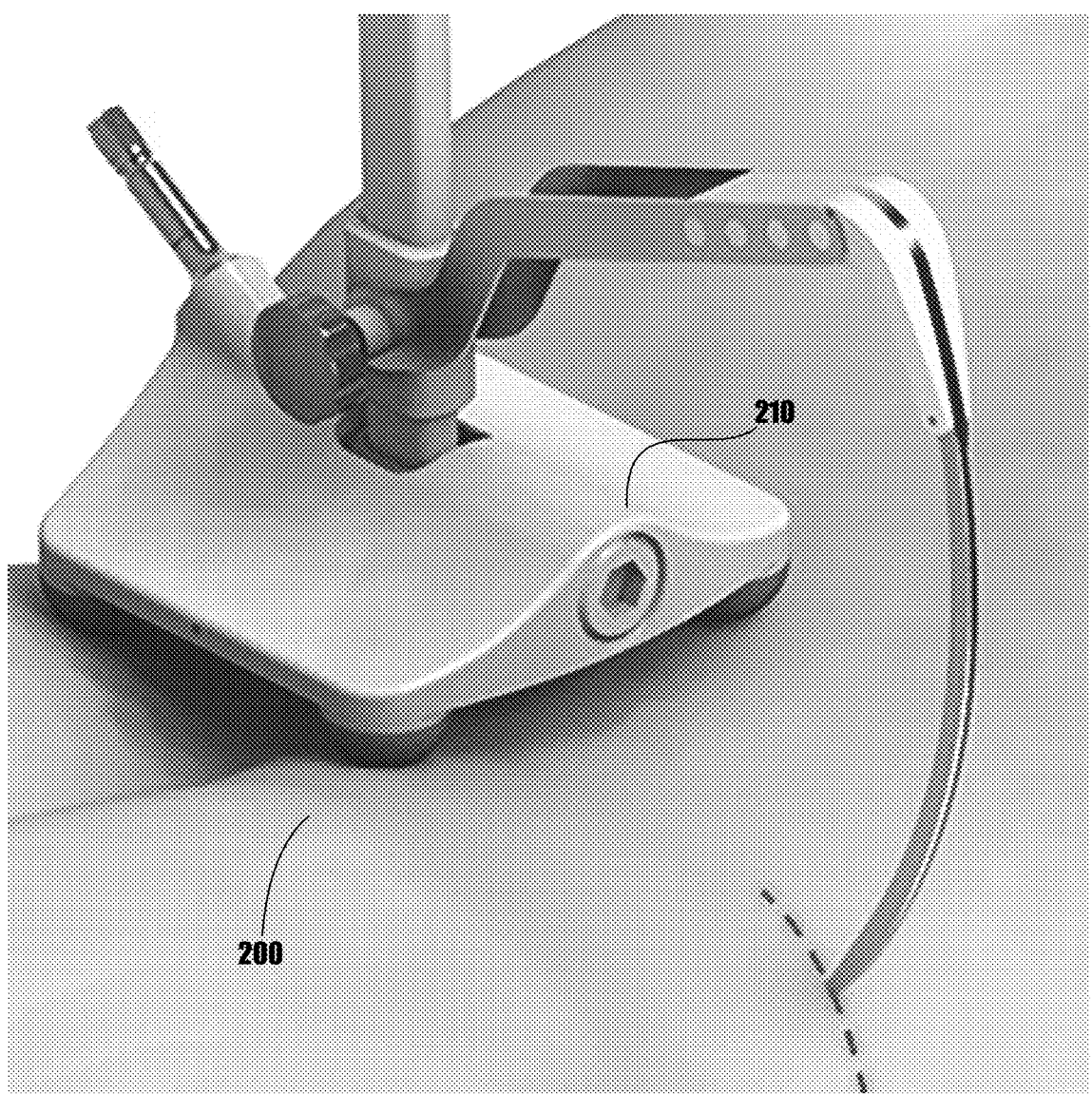
FIG. 15 is a schematic showing an incision guidance instrument in accordance with the disclosure positioned relative to a portion of human anatomy.
Figure 16:
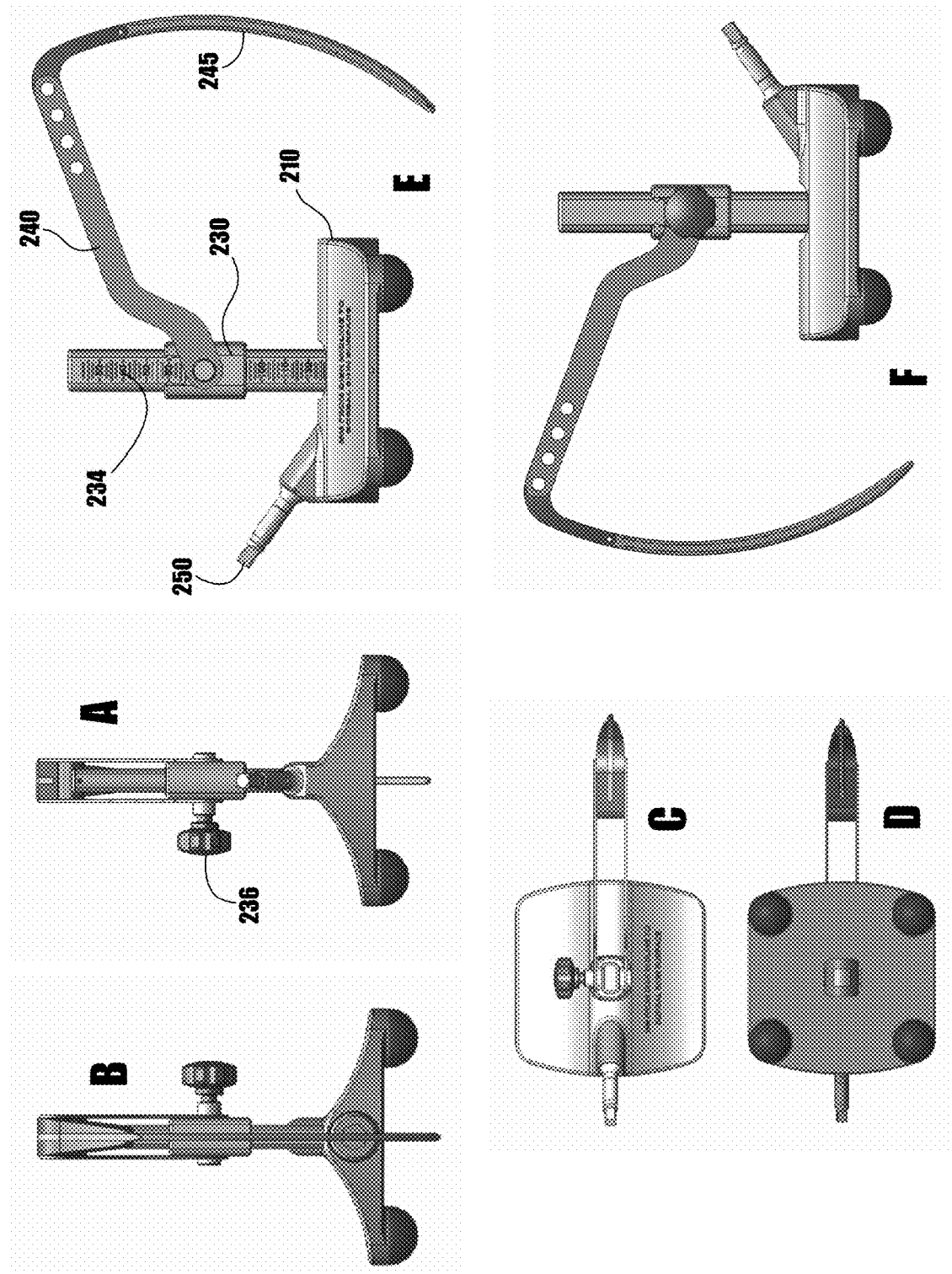
FIG. 16 includes in panels A, B, C, D, E, F and G, respectively, alternate back, front, top, bottom, first and second side, and oblique views of an incision guidance instrument in accordance with the disclosure.

Referring again to the drawings, FIG. 15 is a schematic showing an incision guidance instrument in accordance with the disclosure positioned relative to a portion of human anatomy. The instrument is useful, in particular, for aiding in the selection of incision site on a patient, particularly on a patient in a prone position for whom a lateral mode of access to a spinal vertebra or vertebral space is desired. The guidance instrument includes a support base formed of essentially radio translucent material. In the depicted embodiment, the base is generally square or rectangular to aid in the orientation of positioning and is embedded with crosshair-oriented position indicators. When the base is placed in the intended orientation relative to the target tissue, such as the spine, the position indicators extend in superior to inferior and transecting lateral dimensions and are formed of radio opaque material. The instrument also includes a vertically adjustable depth indicator that extends from an upper surface of the support base and is desirably formed of essentially radio-translucent material.

In various embodiments, the depth indicator includes a vertically translatable extender with graduated markings in conventional units of measure, or alternatively markings indicating a predetermined position relative to a position of the patient's anatomy. The extender may include an extender lock. The guidance instrument also includes a vertically adjustable and substantially linear pivot arm that extends on an axis that is parallel to the lateral dimension of the position indicators and is adjustable and lockable vertically. In the depicted embodiment, the pivot arm is attached at a first end to the vertical extender and pivots from a position that is parallel with the extender to a position that is perpendicular to the extender and parallel to the plane of the base. In various embodiments, the pivot arm has an arcuate pointer extending from a free end of the pivot arm. The arcuate pointer is formed of radio opaque material, allowing its detection by radiography, such as for example, X-Ray fluoroscopy. The arcuate pointer is attached to the pivot arm, and may be adjustably attached to enable adjustable extension therefrom. The guidance instrument may also comprise a support bracket adapter for attachment to a support bracket fixture that is remote from the surgical field.

In some embodiments, the guidance instrument may include a through hole in the base which would allow passage of a substantially cylindrical instrument therethrough. For example, in some embodiments, the guidance instrument has a removable vertical extender that can be replaced with a needle, probe or Jamshidi type device that can affix either directly or through the skin to a spinal structure, such as a spinous process on a vertebra. In some embodiments, the inserted instrument can be fixed to the base and the pivot arm attached thereto. In other embodiments, the instrument can be removed after it is used, for example, to directly determine the depth of soft tissue from the surface of the skin to the bony structure. According to such embodiments, the removed instrument is replaced with the vertical extender. FIG. shows alternate back, front, top, bottom, first and second side, and oblique views of an incision guidance instrument in accordance with the disclosure.

One of ordinary skill will appreciate that the overall shape of the base may be varied so long as the relevant orientation of the indicators is evident, and that the indicators may be affixed and removable from the base rather than being embedded therein. It will also be appreciated that the guidance instrument may be used for other surgical contexts beyond the spine, taking advantage of the device's features to identify a desired position within a patient relying on the geometric relationship of the indicators and the arcuate pointer to select an incision site.

Figure 17:
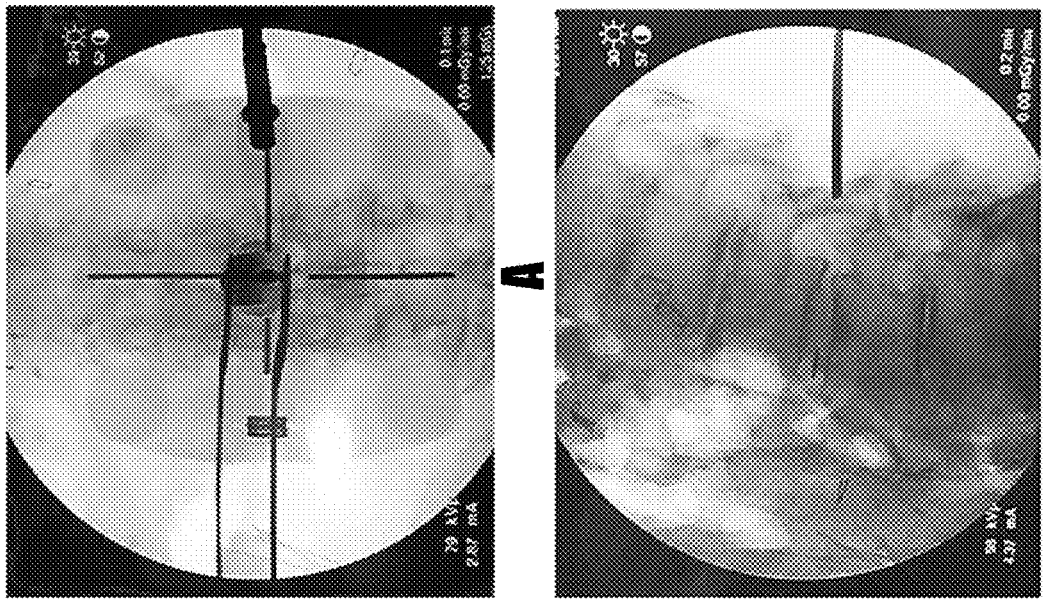
FIG. 17 shows in panel A a radiographic image from a human model showing an anterior to posterior (AP) view of a human spine over which is positioned on the patient an incision guidance instrument, and in panel B a radiographic image from a human model showing a lateral view of a human spine over which is positioned on the patient an incision guidance instrument, the schematic showing the orientation of the arm of the guidance instrument relative to an intervertebral disc space and the overlying skin surface for determining incision location.
Figure 16:
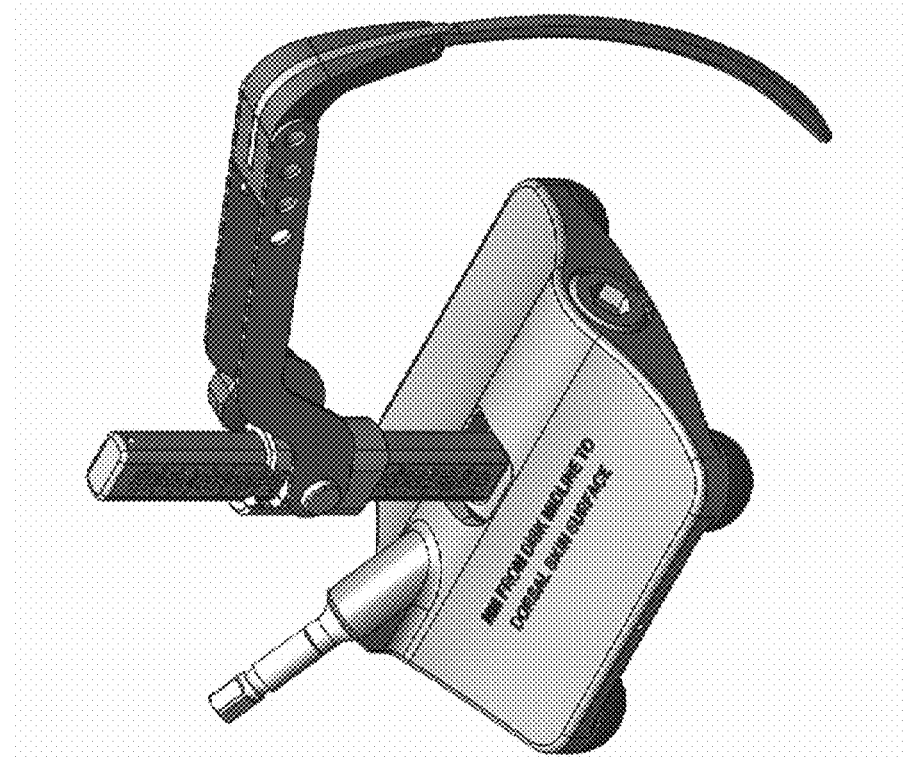

In use, the guidance instrument is positioned on the surgical subject and under fluoroscopy to confirm collinear alignment of one or more indicators with target tissue. For example, AP fluoroscopy is used to confirm collinear alignment of one or more indicators with the spine along the sagittal plane, and lateral alignment with the target disc space along the transverse plane. FIG. 17 shows in panel A a radiographic image from a human model showing an anterior to posterior (AP) view of a human spine over which is positioned on the patient an incision guidance instrument.

In various embodiments, the height of the vertically adjustable extender is selected to enable travel of the incision guidance instrument pivot arm along the desired radius of curvature whereby the arcuate pointer would enter the disc space adjacent to a vertebra of interest at a position that is dorsal to the midline of the disc along the frontal plane, at approximately 30% of the overall disc height (in the AP dimension) from the posterior disc margin, wherein the disc height is measured radiographically, for example using CT radiography, as the distance between the anatomical posterior and anterior disc margins.

It will be appreciated that the locus of entry into the disc space in the AP dimension is selected based upon the particular anatomical features of a human spine and the dimensions of the retractor components. Thus, it will be further appreciated that in other embodiments, the entry point for achieving centering relative to target tissue, including the spine, may be varied so as to achieve desired positioning, and the disclosed entry point of entry at a position that is dorsal to the midline of the disc along the frontal plane, at approximately 30% of the overall disc height (in the AP dimension) from the posterior disc margin is non limiting.

Thus, in other embodiments wherein access to the spine is desired, the entry position may be more dorsal or more ventral, and may be anywhere within the range from 1% to 99% of the overall disc height from the posterior disc margin, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99%.

More particularly, the height of the attachment point of the pivot arm to the vertically adjustable extender is determined based on one or more anatomical measurements obtained radiographically or manually relative to a vertebra of interest, including one more of a spinous process, anterior and posterior vertebral margins, and associated disc margins. According to some such embodiments, the measurements are selected from distance from a skin surface above the spinous process to the spinous process, distance from the top of the spinous process to the anterior margin of the disc, and distance from the top of the spinous process to the posterior margin of the disc.

Once the height of the pivot arm is set, lateral fluoroscopy is used to confirm the contact point of the arcuate pointer at the center of the disc space in the SI dimension, and is point of contact on an external surface of the subject's skin is selected as the incision site. FIG. 17 shows in panel B a radiographic image from a human model showing a lateral view of a human spine over which is positioned on the patient an incision guidance instrument, the image showing the orientation of the actuate pointer of the arm of the guidance instrument relative to an intervertebral disc space and the overlying skin surface for determining incision location In various embodiments of the guidance instrument the arcuate pointer has a radius of curvature from about 5 to 50 cm, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50, and incremental fractions thereof including 0.1, 0.2, 0.3, 0.4, 0.5, 0.6, 0.7, 0.8, 0.9 cm.

Thus, in various embodiments according to the disclosure, there is provided a guidance instrument for selecting an incision site for access to the spine of a surgical subject, comprising a support base formed of essentially radio translucent material and comprising crosshair-oriented position indicators that extend in superior to inferior and transecting lateral dimensions and are formed of radio opaque material and a vertically adjustable depth indicator that extends from an upper surface of the support base and is formed of essentially radio-translucent material.

In various embodiments, the depth indicator comprises a vertically translatable extender with graduated markings in conventional units of measure, an extender lock, a vertically adjustable and substantially linear pivot arm that extends on an axis that is parallel to the lateral dimension of the position indicators and is adjustable and lockable vertically and which is attached at a first end to the extender and pivots from a position that is parallel with the extender to a position that is perpendicular to the extender. In various embodiments, the pivot arm comprises an arcuate pointer extending from a free end of the pivot arm and formed of radio opaque material, the arcuate pointer adjustably attached to the pivot arm to enable adjustable extension therefrom, and, a support bracket adapter for attachment to a support bracket fixture that is remote from the surgical field.

In use, the guidance instrument is positioned on the surgical subject and under AP fluoroscopy to confirm collinear alignment with the spine along the sagittal plane and lateral alignment with the target disc space along the transverse plane, and the vertical height of the pivot arm is selected to approximate centerline of the disc space and visualize with lateral fluoroscopy to confirm whereby the contact point of the arcuate pointer on an external surface of the subject's skin is selected as the incision site.

In various embodiments of the guidance instrument the arcuate pointer has a radius of curvature from about 5 to 50 cm, and the height of the vertically adjustable extender is determined based on one or more anatomical measurements obtained radiographically or manually relative to a vertebra of interest, including one more of a spinous process, anterior and posterior vertebral margins, and associated disc margins. According to some such embodiments, the measurements selected from distance from a skin surface above the spinous process to the spinous process, distance from the top of the spinous process to the anterior margin of the disc, and distance from the top of the spinous process to the posterior margin of the disc. In various embodiments, the height of the vertically adjustable extender is selected to enable travel of the incision guidance instrument pivot arm along the desired radius of curvature whereby the arcuate pointer would enter the disc space adjacent to a vertebra of interest at a position that is dorsal to the midline of the disc along the frontal plane, at approximately 30% of the overall disc height from the posterior disc margin.

Surgical Access System

Figure 18:
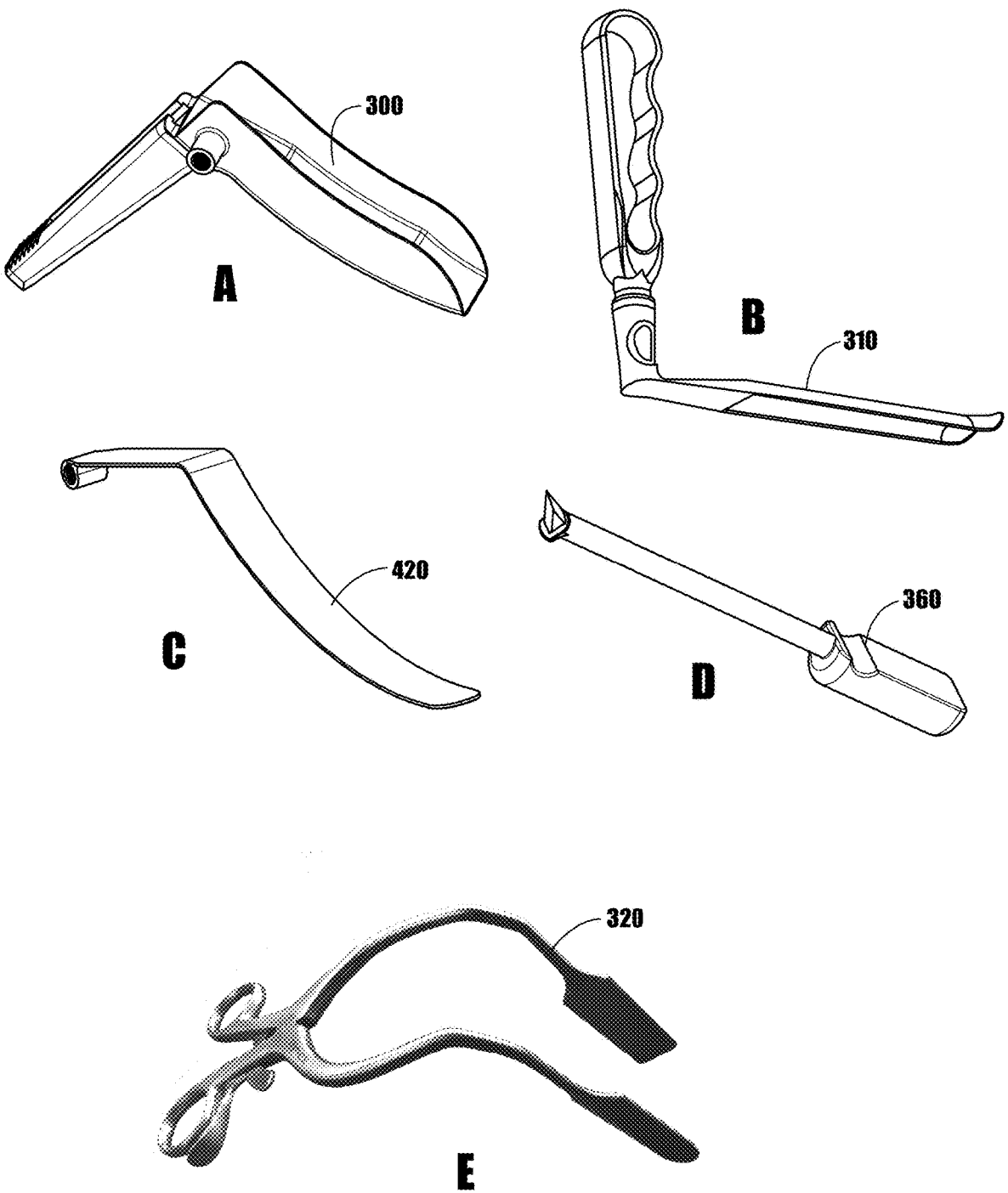
FIG. 18 includes oblique views of each of the insertion instruments, including in panel A speculum shoehorn, in panel B a handheld retractor, in panel C a ribbon blade, in panel D an awl, panel E a bilateral retractor, in panel F a hood handle, in panel G a shim, and in paned H a driver.
Figure 18:
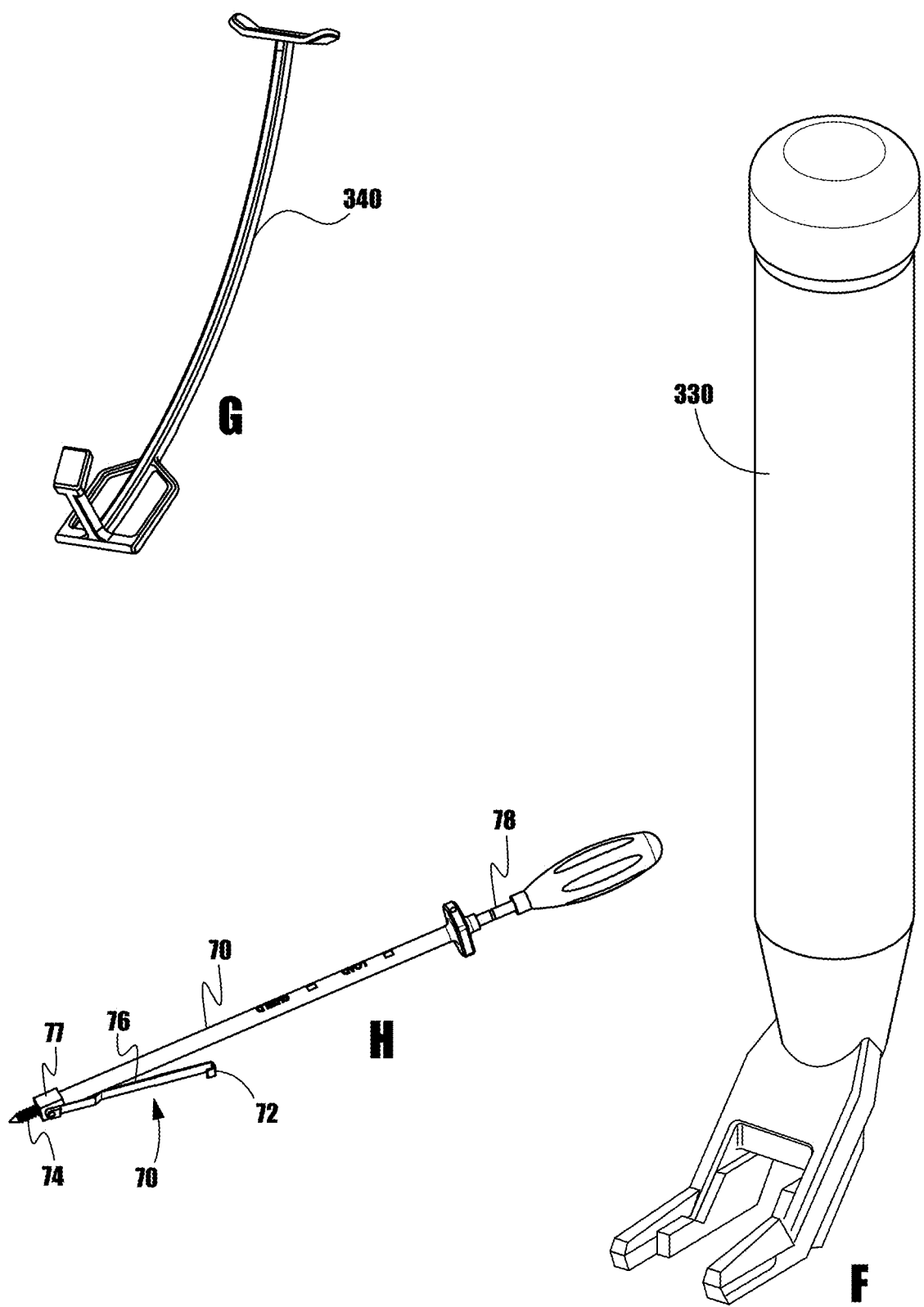
Figures 24, 25:
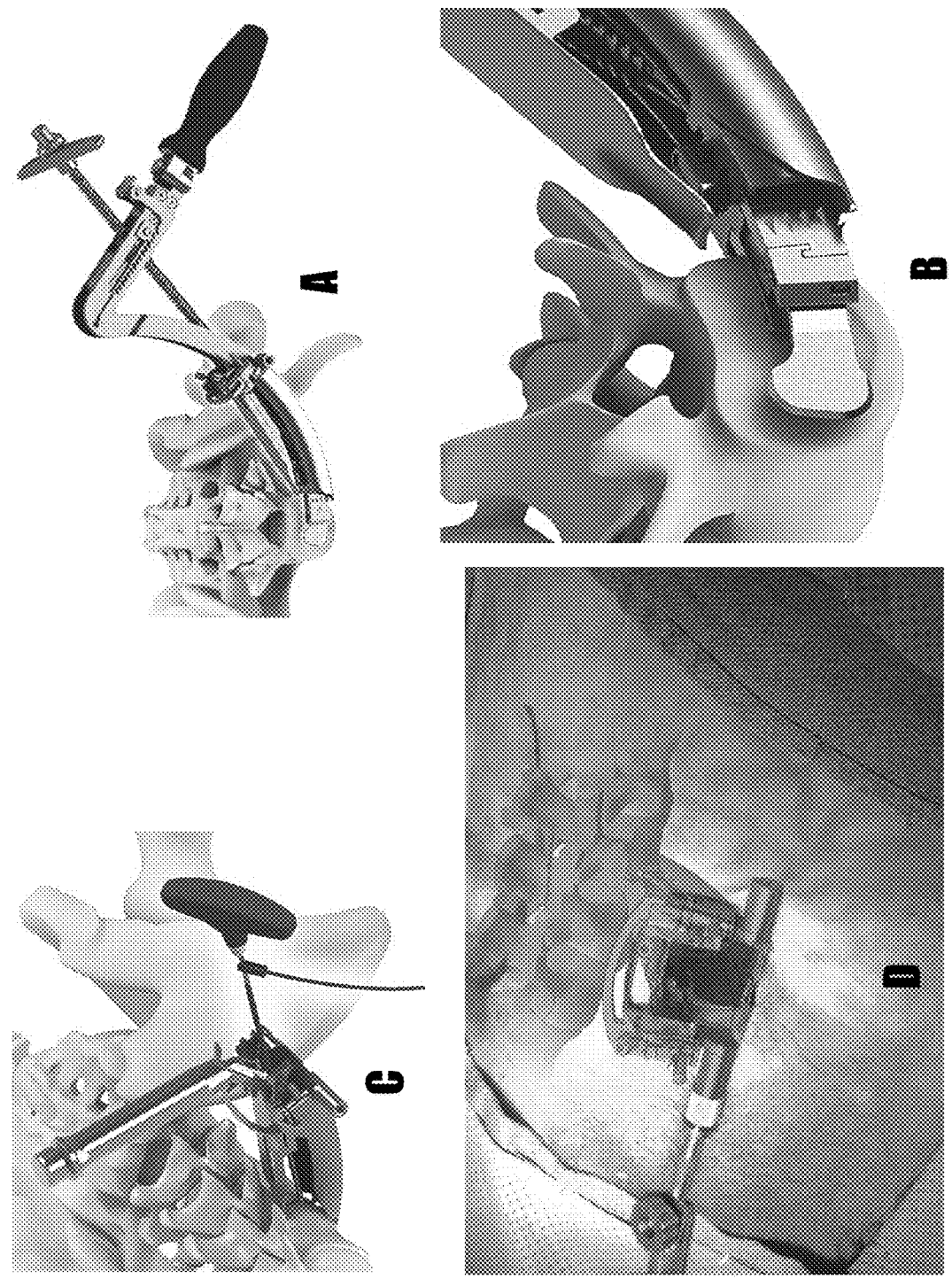
FIG. 24 includes in panel A another alternate view of the schematic shown in FIG. 20 A further depicting the insertion of a second modular retractor component adjacent to the first modular retractor component using a handle, and in panel B a photograph showing the insertion instruments of panel A as inserted into a human model, and in panel C a schematic showing the instruments of panel B with a neuro-monitoring probe inserted therein, and in panel D a schematic showing the assembled and positioned adjacent to the spine and affixed with a table arm.
FIG. 25 includes in panel A a schematic showing an embodiment of a tissue cutting assembly inserted through a modular retractor and positioned adjacent to a spine, and in panel B a close up of the distal/front end of a blade of a cutting assembly depicting insertion through and into a disc.
Figure 29:
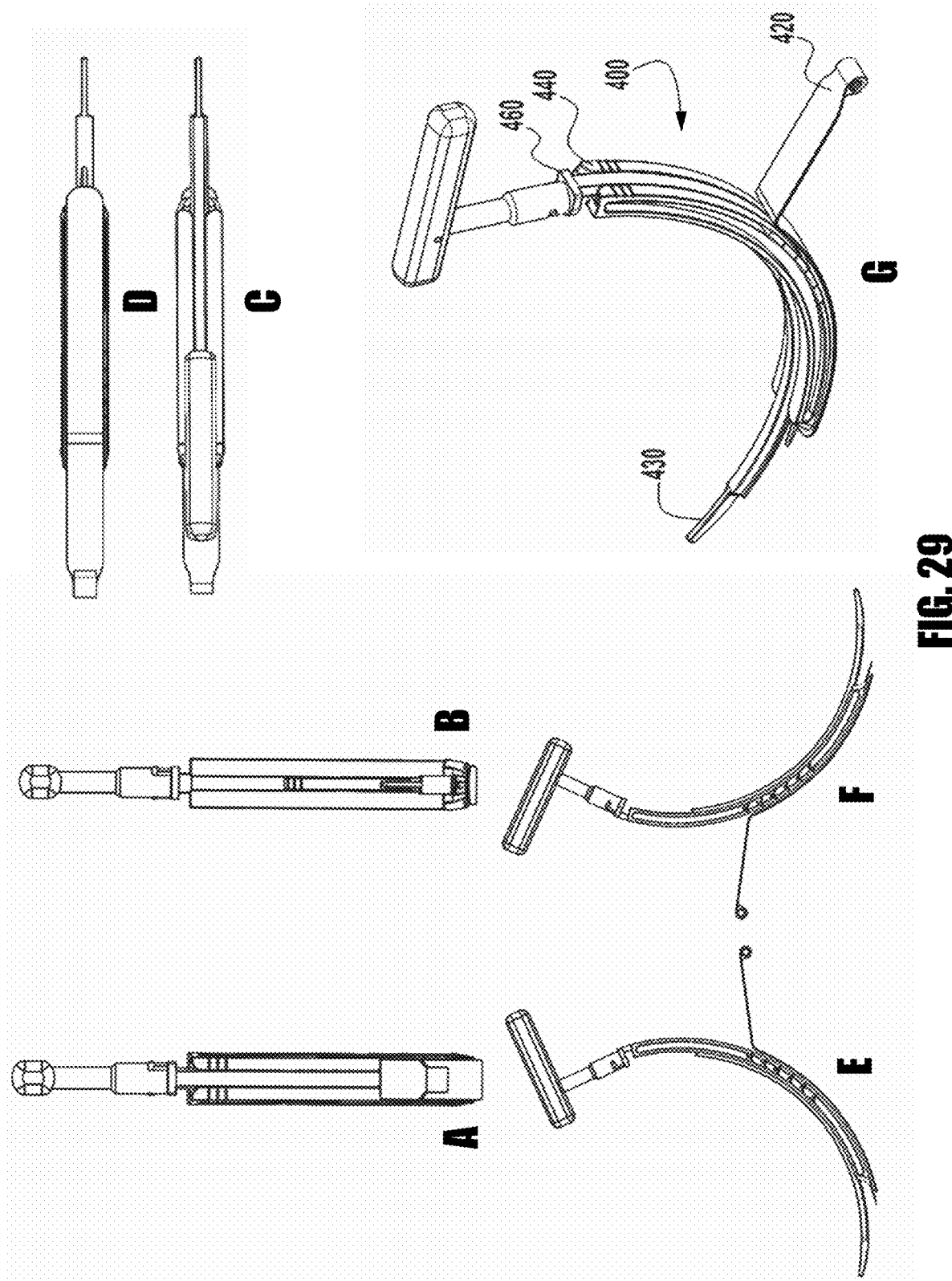
FIG. 29 includes in panels A, B, C, D, E, F and G, respectively, alternate back, front, first and second side, bottom, top, and oblique views of a nested and partially exploded assembly of dilation instruments for assembly of a modular retractor in accordance with the disclosure.

In various embodiments according to the disclosure, use of the retractor device and other system tissue preparation instruments involves the use of other instruments, including tissue retraction and tissue dilation instruments. Thus, among the suite of available instruments some or all of which may be selected for use by a user, and are provided in this disclosure. Referring now to FIG. 18, tissue retraction instruments are shown that include an expandable bilateral speculum, a handheld hood retractor, a handheld speculum shoehorn, a tang awl, and a ribbon blade. Referring now to FIG. 19, tissue dilation instruments are shown that include interfitting first and second dilator components and awl. FIG. 29 shows alternate views of the dilator, tang awl and ribbon blade instruments.

In use, the tissue dilation instruments are used to achieve successively greater dilation of soft tissue as may be deemed appropriate by the surgeon. Further, the instruments inter-engage with the retractor components along the trajectory of the selected radius of curvature to achieve ideal positioning of the instruments at the target tissue. Thus, in use, the first dilator is suitable to establish engagement at the target tissue at the entry position of 30% of the disc height from the posterior disc margin. Thereafter, each of the instruments is used successively to engage and provide a path for achieving lateral access to the spine.

Placement of the ribbon blade ventral to the first dilator establishes a smooth path for the passage of the second dilator which inter-engages with the first dilator and aids in further spreading the soft tissue at the target site. Insertion of the tang awl through the receiving channel in the second dilator enables controlled guidance of the piercing tip of the awl into the ventral aspect of the annulus at the target disc, dorsal to the anterior disc margin, and in various embodiments the tang awl insertion position may be from between 1% and 20% or more of the total disc height from the anterior disc margin, including 1, 2, 3, 4, 5, 6, 7, 8, 9, 10, 11, 12, 13, 14, 15, 16, 17, 18, 19, and 20%. Advantageously, the tang awl establishes the initial entry point for a tang, which may be used as tissue securement component. Subsequent insertion of the retractor body adjacent and ventral to the second dilator/tissue dilation assembly positions the distal end of the retractor body relative to the disc space, and the path of the tang awl ensures precise positioning of the tang within the annulus. Upon withdrawal of the dilation assembly from the incision, SI and AP radiography can be used to confirm the proper orientation of the retractor body relative to the disc space and SI radiography can be used to confirm that the tang is substantially parallel to the anterior annulus.

As described herein above in connection with embodiments of the retractor, the retractor components and related instruments may be curvilinear or rectilinear, and those that are curvilinear have a radius of curvature that ranges from 5 to 60 cm or more. It will be appreciated by one of skill that the radius of the retractor and other instruments is influenced by the selected radius of curvature for achieving lateral access to the disc space. Generally, the greater the radius, the flatter the channel and instruments, dictating a more ventral incision site on the patient, and the smaller the radius, the steeper the channel and instruments, dictating a more dorsal incision site on the patient.

Without being limiting, the radius of curvature of instruments according to the disclosure, particularly the ribbon blade, the first and second dilators and interfitting tang awl, the hand held speculum, and other instruments not specifically disclosed herein that may be adapted from conventional rectilinear profile for use with the inventive retractor, may be within a range from about 0 cm to about 60 cm or more, and more particularly from about 5 cm to about 25 cm, and in some embodiments the radius may be selected from one of 15 cm, 17 cm, 17.5 cm, 18 cm, 22 cm, 22.5 cm, and 25 cm. Of course other radii are possible within the range from 0 cm to more than 60 cm, including 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60, and incremental fractions thereof including 0.1, 0.2, 0.3, 0.4, 0.5, 0.6, 0.7, 0.8, 0.9 cm.

Selection of and some optional representative uses for the instruments are further described herein in connection with the description of surgical techniques. One of ordinary skill will appreciate that other conventional and functional surgical instruments may be used in connection with the devices and systems and techniques disclosed herein, and the identified instruments are not exclusive and are not limited or limiting.

Thus, in various embodiments according to the disclosure, there is provided a surgical system for preparing soft tissue for a surgical procedure within a patient. The surgical system comprises a tissue dissection system comprising one or more of a handheld speculum shoehorn, a handheld retractor, an expandable bilateral speculum, a tang awl, a tissue dilation system comprising interfitting retractor and dilator components. According to some such embodiments, the dilator components are selected from two or more of, at least one retractor body and at least one retractor hood, a ribbon blade, a first dilator that is receivable within a second dilator, a second dilator that interfits with the first dilator and is receivable within the retractor body, an awl receivable within the second dilator, each of the interfitting retractor and dilator components having a proximal end that is adapted to extend outside of the patient and a distal end that is adapted for contact with the target tissue.

According to some specific embodiments, the medical system comprises a retractor body and a retractor hood; a ribbon blade having at its proximal end at least one support bracket adapter for attachment to a support bracket fixture that is remote from the surgical field; a second dilator adapted to be slidably received adjacent to the retractor body without interference, and comprising a first channel for slidably receiving a first dilator with an clearance fit and a second channel for slidably receiving an awl with an clearance fit, a first dilator; and an awl. According to some such embodiments, each of the first and second dilators comprise grip features for attaching an external instrument to guide, orient or drive insertion into tissue, the awl comprises a distal blade and a releasable hand actuator for driving the distal blade into tissue. According to some such embodiments, the medical system also comprises a handheld speculum shoehorn, a handheld retractor, an expandable bilateral speculum, each of the instruments adapted for independent manual control for manipulation and dissection of soft tissue.

EXAMPLE 1

Representative Surgical Technique

With reference now to the drawings, in particular FIG. 20-FIG. 24C, a representative embodiment of a surgical technique includes the following steps, the order of which is not intended to be limiting:

Position the Patient

Position patient prone (and generally parallel to the floor) on suitable surgical table.

Establish Incision Site

Obtain CT scan to measure ventral to dorsal height of target vertebral space.

Radiographically or directly measure with a needle or wire the posterior soft tissue depth to spinous process over target disc space. (If procedure is open, this step is not required.)

Calculate total ventral to dorsal height, and adjust incision guidance instrument guide height to enable direction of incision guidance instrument pointer to a position that is approximately 30% of the overall disc height from the posterior disc margin, based on the calculated disc height. (This is the target entry point into the disc space, dorsal to the midline of the disc along the frontal plane.) Rest exemplary represented instrument for measurement ("incision guidance instrument") on patient (either on soft tissue for a closed procedure, or on spinous process if procedure is open) and use position indicators to roughly align with the spinal axis. Visualize with AP fluoroscopy to confirm collinear alignment with the spine along the sagittal plane and lateral alignment with the target disc space along the transverse plane. Engage incision guidance instrument pivot arm to approximate centerline of the disc space and visualize with lateral fluoroscopy to confirm. As needed, adjust fluoroscope position to achieve complete alignment of the image path and the incision guidance instrument, as confirmed in the fluoroscopy image. Mark skin to indicate cranial to caudal spinal midline, position of incision guidance instrument on the patient, and incision site to enable access at the target disc entry point.

Incision and Soft Tissue Dissection

Incise skin in a dorsal to ventral orientation, an exemplary incision width being approximately 4 cm. Using a Bovie, dissect through the subcutaneous tissue and muscles, and puncture through the Transversalis fascia into the retro peritoneum with a Kelly clamp. Manually enlarge the fascia incision and dissect the retro peritoneum towards psoas muscle, palpating the transverse process to confirm the posterior margin of disc space. Optionally, insert and engage retraction instrument(s), such as a bilateral speculum, in a cranial to caudal orientation to further expand the surgical field and expose the spine and associated soft tissue. Manually confirm nerve position relative to the psoas muscle to establish dissection point, and provisionally dissect.

Insert retraction instrument(s) in a ventral to dorsal orientation, inserting a handheld hood retractor with its base oriented to the ventral aspect of the incision and insert handheld speculum shoehorn oriented to the dorsal aspect of the incision to visualize the lateral psoas (FIG. 20). Remove cranial to caudal retractor(s) bilateral retractors, if used. While maintaining posterior soft tissue distraction with the handheld speculum shoehorn, introduce an awl and pass through the provisionally dissected psoas muscle to pierce the ipsilateral annulus (FIG. 21A). Optionally, under lateral visualization, confirm awl insertion at the 30% target entry point relative to the posterior disc margin. Insert a first dilator to complete dissection of the psoas and penetrate the pierced annulus, optionally under lateral visualization (FIG. 21B). Insert ribbon blade toward the ventral aspect of the incision and below the first dilator. Position the distal end of the ribbon blade proximate to the anterior margin of the disc space and centered on the disc between the vertebrae to initially retract the soft tissue ventrally (FIG. 21C). Optionally, affix the ribbon blade to the table arm to retain tissue retraction (FIG. 22B).

Optionally, place a measuring instrument (e.g., rule or tape measure) on patient to measure the distances from the spinal midline mark to the center of the first dilator and the ribbon blade. Select retractor body size (for example, small, medium or large). Insert a second dilator between the first dilator and the ribbon blade, slidably engaging it with the first dilator (FIG. 21D).

Insert a tang awl into engagement with the second dilator and pass toward the disc space to pierce the ipsilateral annulus, dorsal to the anterior disc margin, with the awl blade piercing the annulus at a point that is approximately 30% of the disc height from the posterior disc margin (FIG. 22A and FIG. 22B).

Position and advance the retractor body between the second dilator and the ribbon blade. Under fluoroscopy, confirm insertion of the removable tang through the annulus at a point that is approximately 30% of the disc height from the posterior disc margin, thereby establishing a path whereby the centerline of the disc (50% from each of the posterior and anterior disc margins) is aligned with the centerline of the channel formed by the retractors (FIG. 23A). Remove the first and second dilators (FIG. 23B). Insert the hood retractor into the retractor body and advance towards the disc space and into contact with the disc just ventral to the transverse process (FIG. 24A). Manipulate the proximal end of the hood retractor to engage the psoas muscle, retracting it in a dorsal direction by raising the hood to increase separation between the hood retractor and retractor body (FIG. 24B). Engage the mating features of the hood and retractor body components at their proximal ends. Adjust the lateral position of the hood retractor by moving it proximally or distally to retain elevation of the psoas and avoid compression with the transverse process. Lock the retractors in the selected position. Remove the ribbon blade, and optionally affix the retractor body to the table arm (FIG. 24D). Optionally, engage a tissue fixation element, for example a screw or pin, to enhance engagement with one or both vertebrae.

At any time during the dissection of the psoas or placement of the retractor components, a stimulator may be placed in the wound and tissue stimulated to monitor for nerves (FIG. 24C). Likewise, at any time the anterior to posterior position of the hood retractor may be adjusted to relive any degree of compression on the spinal nerves.

EXAMPLE 2

Representative Surgical Technique

According to the foregoing disclosure, in various embodiments, there is provided a method for performing a surgical procedure on the spine of a patient, the method comprising: opening the surgical field through an incision that is substantially posterior, dissecting soft tissue to initially contact and visualize a target vertebra, placing a first retractor within the surgical field to retract soft tissue, the retractor having a distal end positioned substantially adjacent to the anterior aspect of the spine at the intervertebral space between the target vertebra and an adjacent vertebra. According to such embodiments, the method also comprising sliding into the surgical field adjacent to the first retractor a second retractor, the second retractor having a distal end that is adapted for manipulating soft tissue, manually directing the second retractor towards the spine and vertically displacing the second retractor posteriorly and away from the first retractor so as to lift the soft tissue posteriorly/dorsally to enhance visualization of the spine, assembling the first and second retractors into engagement by coupling complimentary coupling elements at proximal ends of the retractors, adjusting the coupled retractors in one or more of three degrees of adjustment and reversibly locking the coupled retractors to establish a channel to the spine.

According to some such embodiments, when coupled retractors are displaced from one another vertically in a first plane along a channel longitudinal axis and constrained to one or more of three degrees of freedom, being movable pivotally around a pivot axis at the proximal end that is essentially perpendicular to the channel longitudinal axis, displaceable vertically to a pre-selected displacement distance, or slidable horizontally along the common longitudinal axis, or combinations of these. According to various embodiments, the patient is in a prone position, and at least one of the retractors is curvilinear.

Instrument for Tissue Preparation

This disclosure provides a suite of tissue manipulation instruments that enable access to and manipulation of tissue with minimal invasion of tissue, and in certain embodiments, these instruments reduce or eliminate the percussive techniques that are common in most spinal surgeries. Of course, it will be understood that the instruments may be adapted for use in surgeries other than on the spine of an animal, and while representative embodiments are shown as curvilinear, other rectilinear embodiments are encompassed within the scope of the invention and may be useful for spinal and other applications.

Figure 30:
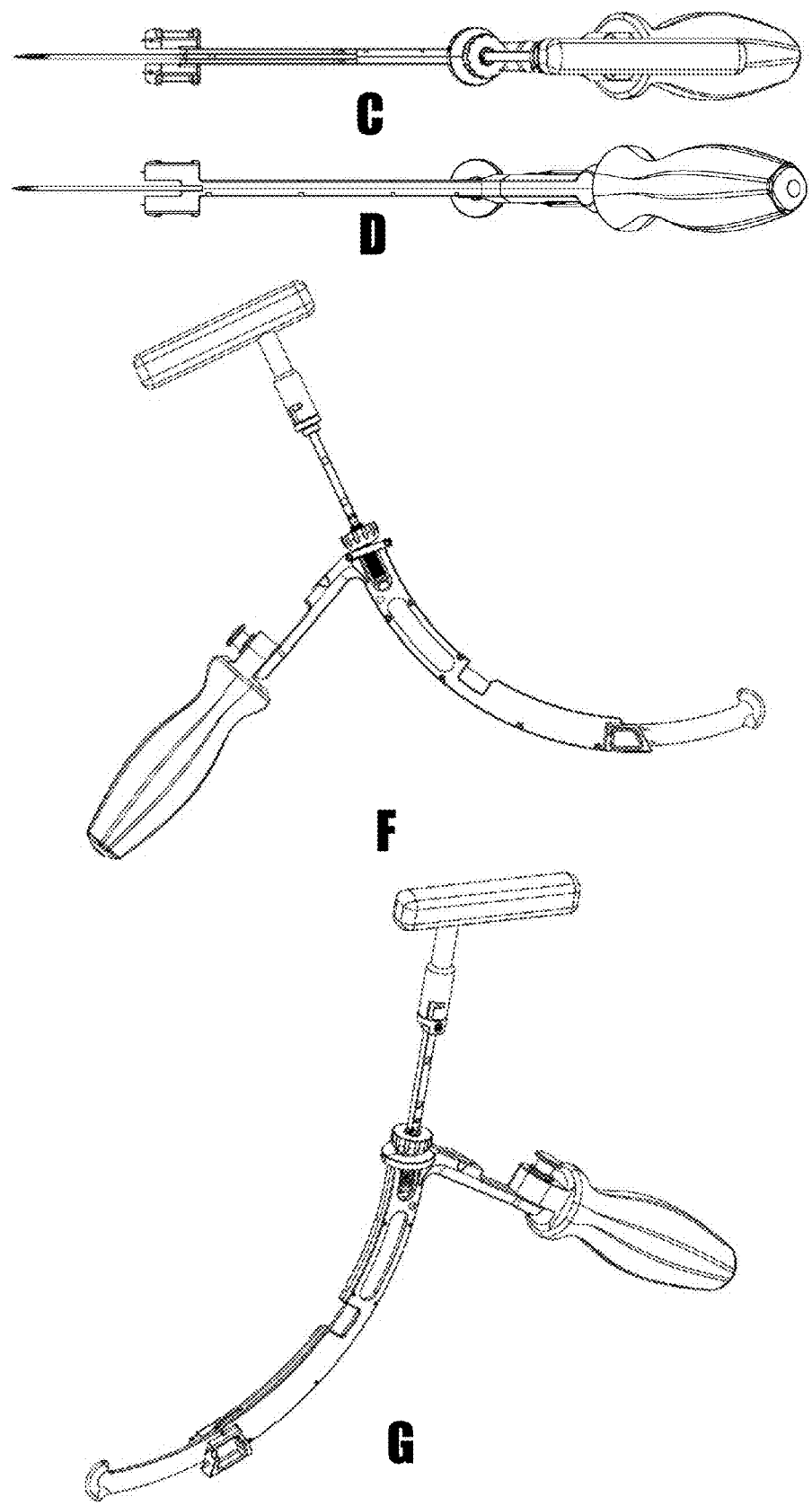
FIG. 30 includes in panels A, B, C, D, E, F and G, respectively, alternate back, front, first and second side, top, bottom, and oblique views of a first embodiment of a cutting assembly having an impact drive plate in accordance with the disclosure.
Figure 31:
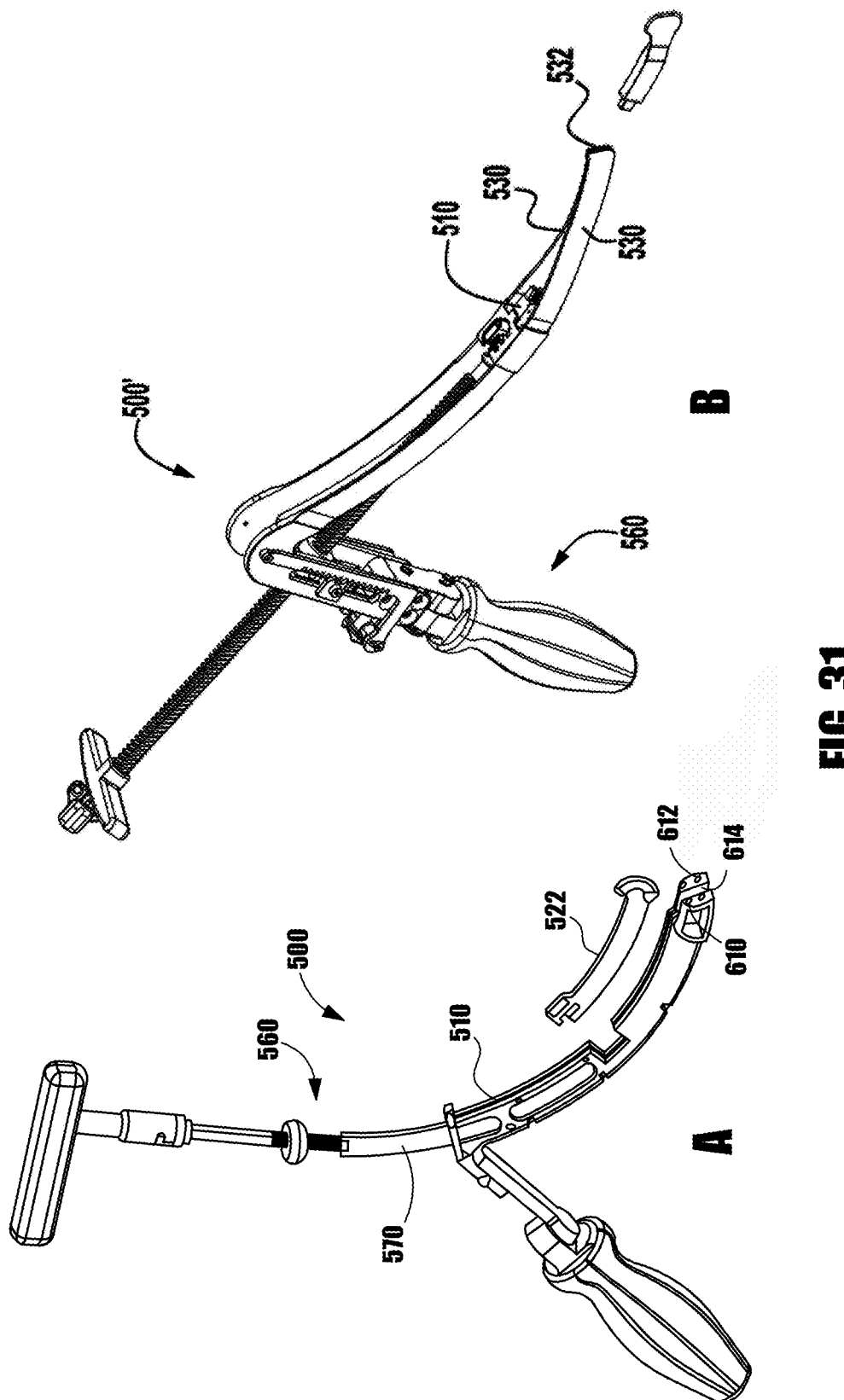
FIG. 31 includes in panel A an exploded view of the embodiment of the cutting assembly shown in FIG. 30 showing the attachment of the removable blade to the instrument, and in Panel B an exploded view of an alternate embodiment of a cutting assembly having an rotational drive in accordance with the disclosure showing the attachment of the removable blade to the instrument.

Referring again to the drawings, FIG. 30 shows alternate views of a tissue preparation instrument that comprises a strike plate for introducing a tissue manipulator component, the represented component being a blade. FIG. 31B shows an alternate embodiment of instrument with a tissue manipulator cutting blade attachment and a second tissue manipulator in the form of parallel elongate blades for distraction of the disc space, wherein the drive for insertion is a rotating screw. As shown, the instrument includes a tissue penetrating blade that is used for cutting through soft tissue, particularly the annulus of a spinal disc. The blade may be attached by a variety of means, and in some embodiments may be permanently affixed to the device, which is thus dedicated to cutting. In alternate embodiments, the cutting blade is removable and interchangeable with other blades, box cutters, and scrapers, each of which interchangeable bladed tissue manipulators may be varied in shape, length, and height. Thus, the disclosure is not limited to the cutting blades described herein and shown in the drawings.

Figure 32:
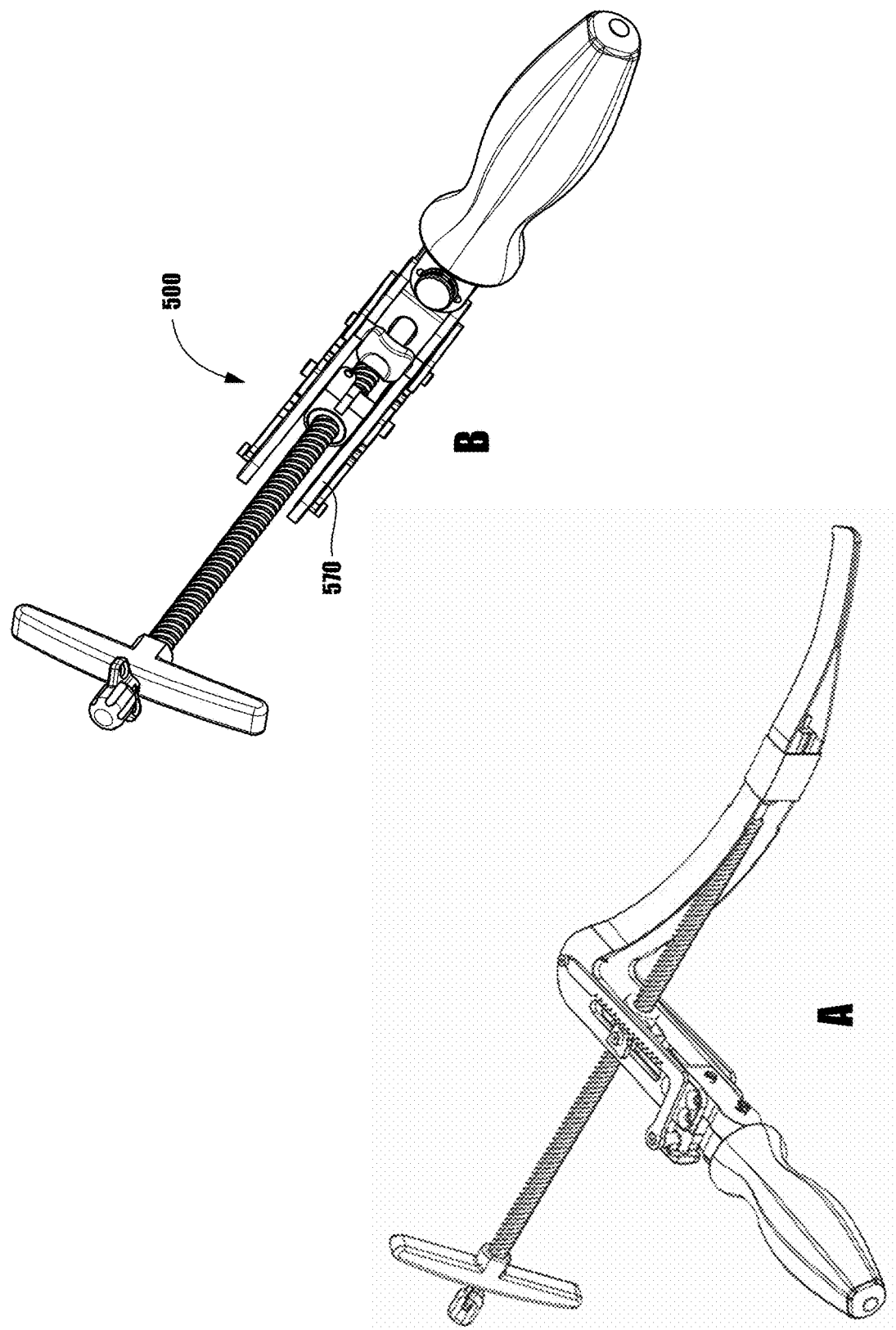
FIG. 32 includes in panels A, B, C, D, E, and F, respectively, oblique, top, oblique, oblique, side, and oblique views of a first embodiment of a tissue preparation device having a rotational drive in accordance with the disclosure.
Figure 32:
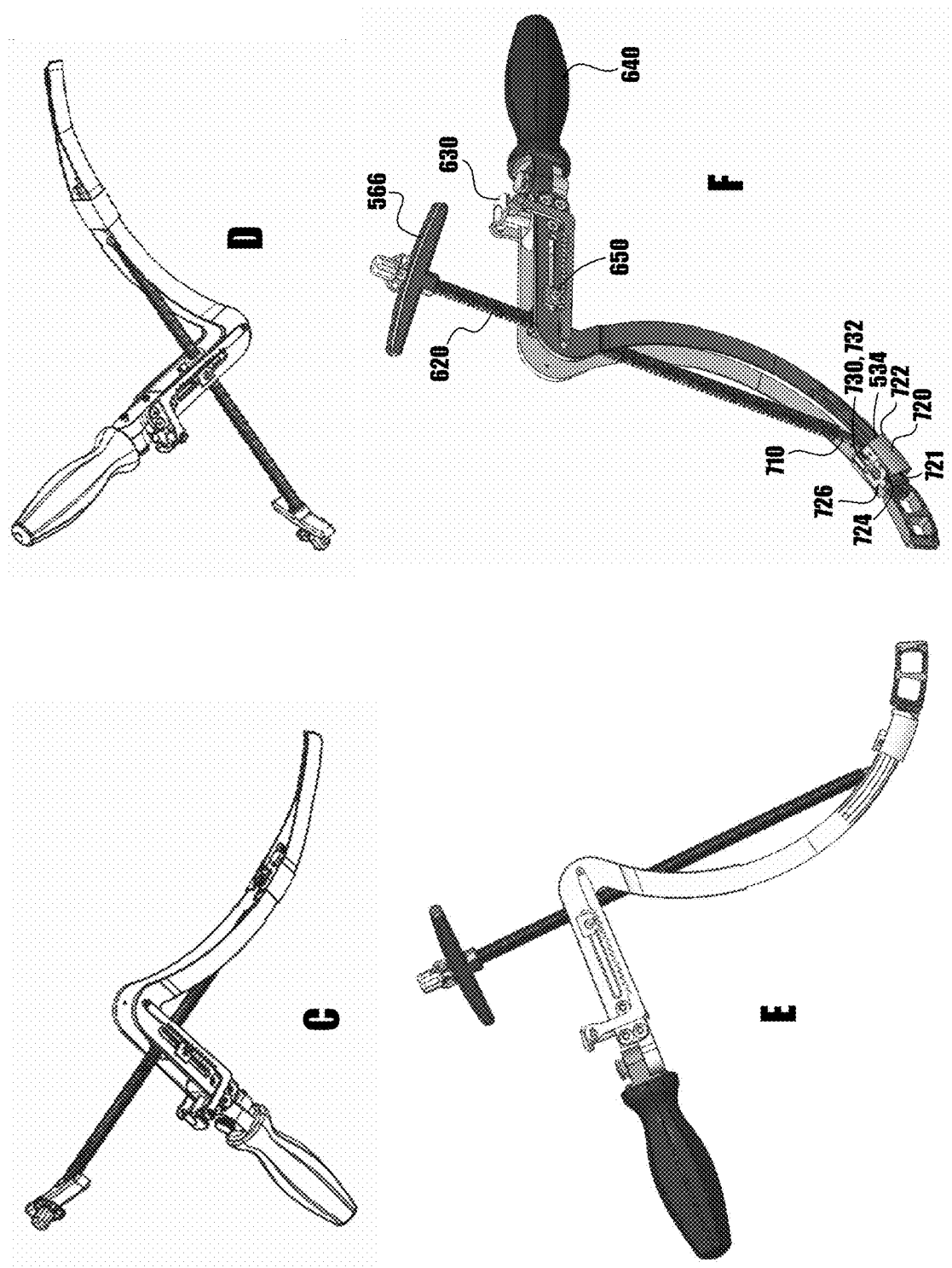

Referring now to FIG. 32, alternate views of another tissue preparation instrument is shown, the instrument comprising the drive system shown in FIG. 31B with an alternate tissue manipulator in the form of an interbody implant.

Tissue preparation instruments according to the disclosure include proximal ends that include drive components and distal ends that include tissue engagement components that include one or more tissue manipulators. The proximal end extends out of the surgical field and the distal end is insertable in the surgical field. In various embodiments, a tissue preparation instrument has a drive mechanism to drive distal and proximal movement of the insertion assembly for manipulating target tissue. In some embodiments, the drive mechanism is selected from a ratchet or gear system comprising one or more rack and pinion components, a walking beam and plates drive system, and, a threaded rod with a shift for providing rotational force. In some threaded rod embodiments, the drive component includes a threaded element affixed to the housing that is adapted to receive and engage with the threaded rod. In some such embodiments, the threaded element is a threaded bore. Rotation of the insertion rod within the threaded element results in movement of the insertion rod in one or the other of the distal or proximal directions. Engagement of a second tissue manipulator, such as for example, and implant directly or indirectly to the universal joint ensures that the tissue manipulator does not rotate when the insertion rod is rotated. Other known free-rotational or swivel mechanisms may be employed as alternatives to the universal joint.

As described herein above in connection with embodiments of the retractor, the retractor components and related instruments may be curvilinear or rectilinear, and those that are curvilinear have a radius of curvature that ranges from 5 to 60 cm or more. In accordance with the disclosure, at least the tissue engagement components of the tissue preparation instruments hereof may be either rectilinear or curvilinear. According to embodiments wherein the tissue engagement components are curvilinear, without being limiting, the radius of curvature of may be within a range from about 0 cm to about 60 cm or more, and more particularly from about 5 cm to about 25 cm, and in some embodiments the radius may be selected from one of 15 cm, 17 cm, 17.5 cm, 18 cm, 22 cm, 22.5 cm, and 25 cm. Of course other radii are possible within the range from 0 cm to more than 60 cm, including 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60, and incremental fractions thereof including 0.1, 0.2, 0.3, 0.4, 0.5, 0.6, 0.7, 0.8, 0.9 cm.

In various embodiments, the tissue manipulators according to the invention may include a housing that at least partially encloses all or a portion of each of the drive components and tissue engagement components. In some embodiments, the housing may be formed of an open frame, a closed frame, one or two pair of opposing slates. A frame may be all or at least partially curvilinear, and may include one or more fixed or adjustable, integrated or attachable/releasable handles. A representative embodiment of an open frame housing is shown, for example, in FIG. 30, and a representative embodiment of a frame comprising a pair of opposing slats is shown in FIG. 32 and FIG. 31B. It will be appreciated that the function of the housing is to support one or more of the drive and tissue engagement components in alignment with the delivery trajectory within a surgical field, including particularly for insertion in the channel formed by the modular retractor. Other housing configurations are possible and may include combinations.

Tissue manipulators in accordance with the disclosure include cutting instruments selected from a single blade, a plurality of blades, and a box shaped blade that has a central void and is rectangular in shape; opposing curvilinear elongated blades, each of the curvilinear blades having a distal end and a proximal end, wherein each of the blades has a radius of curvature from between 5 cm and 60 cm or more, and wherein the distal ends of the curvilinear blades are translatable from a collapsed orientation wherein the blades touch at least at their most distal ends, to a spread orientation wherein the blades are spread apart and not in contact; a distractor paddle; an implant trial; an endplate scraper; an implant; and a length adjuster frame that is adapted for actuation between a plurality of preset lengths to adjust the distance of a tissue manipulator for extension into the disc space. In some embodiments, tissue manipulator blades may be curved, bent or angled laterally (off the blade axis) such that they are deflected away from or toward each other along their lengths or In some such embodiments, at the distal end.

In some embodiments, an adjuster frame is used as an intermediate between the tissue manipulator and the driver, the adjuster frame being releasably engageable with the tissue manipulator such as through engagement pins. The adjuster frame may include one or more extension options for increasing the length of the extension of the manipulator from the driver. According to such embodiments that include a first tissue manipulator that includes a pair of blades, the adjuster frame is adapted to receive the opposing blades such that advancement of the adjuster frame proximal to distal spreads the distal ends of the blades, which aids in distraction of the disc space.

Thus, in various embodiments according to the disclosure, there is provided a spinal tissue preparation device comprising an insertion assembly having a proximal end that is adapted to extend outside of a surgical field and a distal end that is adapted to extend into the surgical field, and an actuator attached to the insertion assembly at its proximal end and adapted to engage with the drive component to direct force along the path between the proximal and distal ends, to selectively advance at least one tissue manipulator in a distal direction, and to withdraw the at least one tissue manipulator in a proximal direction.

According to some such embodiments, the tissue engagement component comprises a tissue engagement component comprising at least one tissue manipulator, and a drive component connected on its distal end to the proximal end of the tissue engagement component, and on its proximal end and to an actuator.

According to some such embodiments, at least the tissue engagement component of the insertion assembly is curvilinear and has a radius of curvature from between 5 cm and 40 cm. According to some such embodiments, the actuator is selected from a strike plate for directing either distal or proximally oriented concussive force to advance or withdraw the insertion assembly, a ratchet or gear system comprising one or more rack and pinion components, a walking beam and plates drive system, and, a threaded rod with a shift for providing rotational force to alternately drive distal and proximal movement of the insertion assembly.

According to some such embodiments, the device also comprises one or more of an adjustable and releasable stabilization handle for positioning and stabilizing the tissue preparation device, the handle being adjustable and releasable to avoid interference with other surgical instruments, and a vertical shift component for dorsal to ventral vertical adjustment and positional locking of the actuator to avoid interference between components of the insertion assembly and with other surgical instruments.

According to some specific embodiments the actuator comprises a strike plate, the drive component of the insertion assembly comprises a curvilinear housing that at least partially encloses the tissue manipulator and at least a portion of the distal end of the actuator, the housing further comprising at its distal end a tissue engagement seat comprising at least a pair of engagement teeth for penetrating target tissue and a guide for directing the tissue manipulator into engagement with the target tissue between the teeth, and comprising an elongate curvilinear push rod engageable at its distal end to the tissue manipulator and at its proximal end to the actuator, and the tissue manipulator comprises a cutting instrument releasably attachable to the drive component, the cutting instrument selected from a single blade, a plurality of blades, and a box shaped blade that has a central void and is rectangular in shape.

In such embodiments a spinal tissue preparation device comprise a first tissue manipulator that comprises a pair of opposing curvilinear elongated blades, each of the curvilinear blades having a distal end and a proximal end, wherein each of the blades has a radius of curvature from between 5 cm and 40 cm, and wherein the distal ends of the curvilinear blades are translatable from a collapsed orientation wherein the blades touch at least at their most distal ends, to a spread orientation wherein the blades are spread apart and not in contact. In some embodiments, the drive system is selected from a ratchet or gear system comprising one or more rack and pinion components, a walking beam and plates drive system, and, a threaded rod with a shift for providing rotational force to alternately drive distal and proximal movement of the insertion assembly.

According to such embodiments, the device comprises one or more of an adjustable and releasable stabilization handle for positioning and stabilizing the tissue preparation device, the handle being adjustable and releasable to avoid interference with other surgical instruments, and a vertical shift component for dorsal to ventral vertical adjustment and positional locking of the drive system actuator to avoid interference between components of the insertion assembly and with other surgical instruments.

According to such embodiments, the device includes a tissue manipulator attachment element comprising a universal joint attachable to the distal end of the drive system actuator, a frame having distal and proximal attachment ends and blade receiving sidewalls into which each of the respective blades are inserted, the frame attachable at its proximal end to the universal joint, and movable from the proximal to the distal ends of the blades to a terminal position defined by a positive stop on one or both blades, a releasable tissue manipulator fastener for engagement of a second tissue manipulator selected from a distractor paddle, an implant trial, a cutting instrument, an endplate scraper, and an implant; a length adjuster that is adapted for actuation between a plurality of preset lengths to adjust the distance of the second tissue manipulator from the frame.

According to such embodiments, in operation, the blades are insertable into the target tissue in their collapsed orientation with the frame at the proximal end of the blades, and positive actuation of the drive component directs the frame towards the tissue and expands the blades, driving the second tissue manipulator into contact with the target tissue, and upon further positive actuation, withdrawing the blades from the tissue leaving the extended second tissue manipulator within the target tissue. And According to such embodiments, negative actuation of the drive component withdraws the frame away from the tissue, drawing the frame toward the proximal end of the instrument and allowing the blades to collapse for easy withdrawal from the surgical field.

According to some embodiments in which a tissue manipulator comprises blades, each of the blades comprises inner and outer surfaces, and a thickness that may be continuous or may vary by narrowing from the proximal to the distal end, each blade having on its outer surface a surface feature to enhance engagement with the surface of tissue. According to such embodiments, the surface feature comprises one or more of ridges, ribs, knurls, hooks, spikes, teeth, or combinations of these, including one or combinations that are either distal, proximal, neutral, or variably directed.

EXAMPLE 3

Representative Surgical Technique to Release Disc Space

Insert tape measure into surgical field adjacent to visualized disc to determine disc height (ventral to dorsal) dimension and initially pierce disc using an elongate scalpel or dissector. Select osteotome blade based on measured ventral to dorsal height of disc. Insert osteotome and advance to contact spine. Using a mallet, impact strike-pad on osteotome body to engage distal opposing teeth with spine (FIG. 25A). Advance blade distally toward disc and using a mallet, impact strike-pad on osteotome body to advance blade through the discus pulpous toward the contralateral annulus (FIG. 25B). Confirm progress radiographically. Disengage osteotome from spine and remove from field. Perform annulotomy and basic nuclectomy using selected instruments (pituitary and other). Affix boxcutter blade to osteotome and insert into field (FIG. 26A). Using a mallet, impact strike-pad on osteotome body to advance box cutter through contralateral annulus. Confirm progress radiographically (FIG. 26B). Disengage osteotome box cutter from spine and remove from field. Insert a disc-cleaning tool to clear vertebral endplates of residual disc material. Remove disc-cleaning tool from field.

EXAMPLE 4

Representative Distraction and Implant Placement

Figure 28:
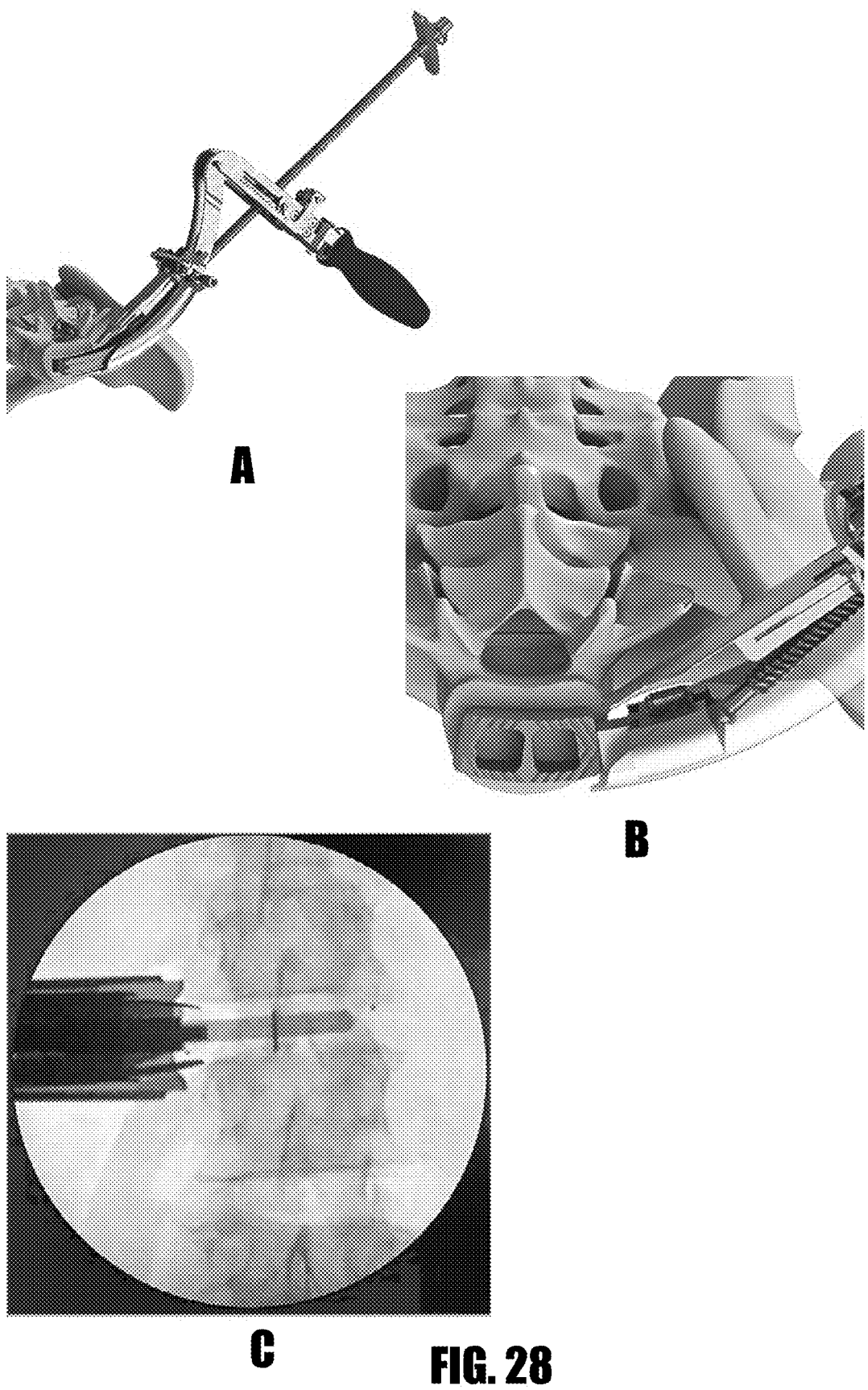
FIG. 28 includes in panel A a view of the tissue preparation device and attached implant inserted through a modular retractor and positioned adjacent to a spine depicting insertion of the implant into the disc space, and in panel B a schematic showing an a close up side view of the distal/front end of the modular retractor with the tissue preparation device inserted there through depicting positioning of the implant within the disc space, and in Panel C a radiographic image from a human model showing an anterior to posterior (AP) view of a human spine showing positioning the implant within the disc space as evidenced by the tantalum marker on the distal end of the implant contralateral to the position of the retractor.

Select implant (not shown) size based on shim placement (length) and trials (height). Insert paddle distractor with estimated trial based on measurements. Rotate trial to enhance distraction of disc space. Confirm progress radiographically (FIG. 27A). Place implant inserter device and trial to confirm implant size. To load the implant and place the implant inserter device: Push release button to disengage threads; Thread implant onto universal joint by turning the knob at the proximal end; Snap the appropriate size guide collar onto the universal joint; Position the implant in the proximal portion of the squid channel (FIG. 27B); Return release button to the flush position to engage the threads; Place implant (FIG. 28A and FIG. 28B), confirming position radiographically (FIG. 28C).

EXAMPLE 5

Representative Surgical Technique

In various embodiments according to the disclosure, there is provided a method for performing a surgical procedure on the spine of a patient, the method comprising, placing a first retractor having a distal end substantially adjacent to an anterior aspect of a spine at a target intervertebral space between a first vertebra and an adjacent vertebra, sliding adjacent to the first retractor a second retractor, the second retractor having a distal end that is adapted for manipulating soft tissue, manually directing the second retractor towards the spine and displacing the second retractor posteriorly and away from the first retractor so as to lift the soft tissue posteriorly/dorsally to enhance visualization of the spine, assembling the first and second retractors into engagement by coupling complimentary coupling elements at proximal ends of the retractors to form a channel between the two retractors having a longitudinal axis that runs distal to proximal, adjusting the coupled retractors pivotally around a pivot axis at their proximal ends to displace the distal ends of the retractors away from one another into an open position, and locking.

According to such embodiments, the method may also comprise selecting a tissue preparation device and fitting it with one of selected tissue manipulators, and proceeding with one or more of the following steps in the provided or any other order, including, inserting the tissue preparation device into the channel and into contact with the target vertebral space, the tissue preparation device fitted with a cutting instrument for penetrating a annulus of a disc within the target vertebral space, and actuating the drive component to direct the cutting instrument into contact with the target vertebral space to penetrate the annulus; actuating the drive component to withdraw and replace the cutting instrument with another cutting instrument for penetrating a contralateral annulus of the disc within the target vertebral space, actuating the drive component to insert the tissue manipulator into contact with the target vertebral space to penetrate the contralateral annulus.

According to such embodiments, the method may also comprise actuating the drive component to withdraw and replace the cutting instrument with a distraction paddle, actuating the drive component to insert the tissue manipulator into contact with the target vertebral space to deliver the paddle distractor which is actuated to enhance distraction of the adjacent vertebrae; actuating the drive component to withdraw and replace the distraction paddle with an endplate scraper, and actuating the drive component to insert the tissue manipulator into contact with the target vertebral space to deliver the scraper which is actuated to withdraw disc material from the disc space.

According to such embodiments, the method may also comprise actuating the drive component to withdraw and replace the endplate scraper with an implant trial and actuating the drive component to insert the tissue manipulator into contact with the target vertebral space to deliver the implant trial to determine implant size.

According to such embodiments, the method may also comprise actuating the drive component to withdraw and replace the implant trial with an implant, actuating the implant length adjuster to optimize centering of the implant in the disc space, actuating the drive component to insert the tissue manipulator into contact with the target vertebral space to deliver the implant, and actuating the release to deposit the implant in the vertebral space, and withdrawing the tissue preparation device from the channel.

Table Apparatus for Surgical Access

In accordance with the disclosure, methods and devices are disclosed that enable enhanced access to the spine, most particularly the lower lumbar region of the spine, for surgical procedures thereon. Included herein are new designs, additions and enhancements comprising pivoting supports 900 suitable for use with existing surgical table designs that allow for manipulation of a patient's anatomy to maximize access to a surgical site of interest, particularly lower lumbar spine access. In some exemplary embodiments, the pivoting supports 900 are useful with a patient in a prone position. The disclosed devices also enable surgical methods that are not possible using existing table and other support devices.

In exemplary embodiments as shown in the drawings at FIG. 33-FIG. 36, a pivoting supports 900 comprises at least two substantially planar platform elements comprising a support platform 950 and a pivot platform 960 that are movable relative to one another and attachable to a table via rails, posts or other means. The relative motion of the platforms 950, 960 is arcuate, and the support platform 950 pivots in a radius of about 42 inches (based essentially on a circle centered on the feet of the patient extending to the top of the pelvis/iliac crest of the average size person). In various alternate embodiments, the radius may be smaller or greater, and may range from 30 inches to 60 inches or more, including 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 inches or more. In various embodiments, the pivot from side to side may vary from about 10 to 60 degrees, and in some embodiments the pivot is about 30 degrees. Thus, the pivot angle may be 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 degrees.

The coupling mechanism or track between the at least two platforms 950, 960 enables smooth motion along the arc, effected with bearings, wheels or other smooth means of translation. The translation means will be resistant to compressive forces of the patient's pelvis and will be fully adjustable by actuation of the motion control.

In some embodiments, the support platform 950 comprises a bolster 954, for example for a thigh to hold the hips and thighs in place. In various embodiments, such bolster 954 may have an angulation typical for bolsters known in the art, for example about 45 degrees with exemplary dimensions of 6"×6"×6". Of course, any other dimensions of bolsters are possible and may be provided at any angulation, the examples given herein being non-limiting.

Figure 33:
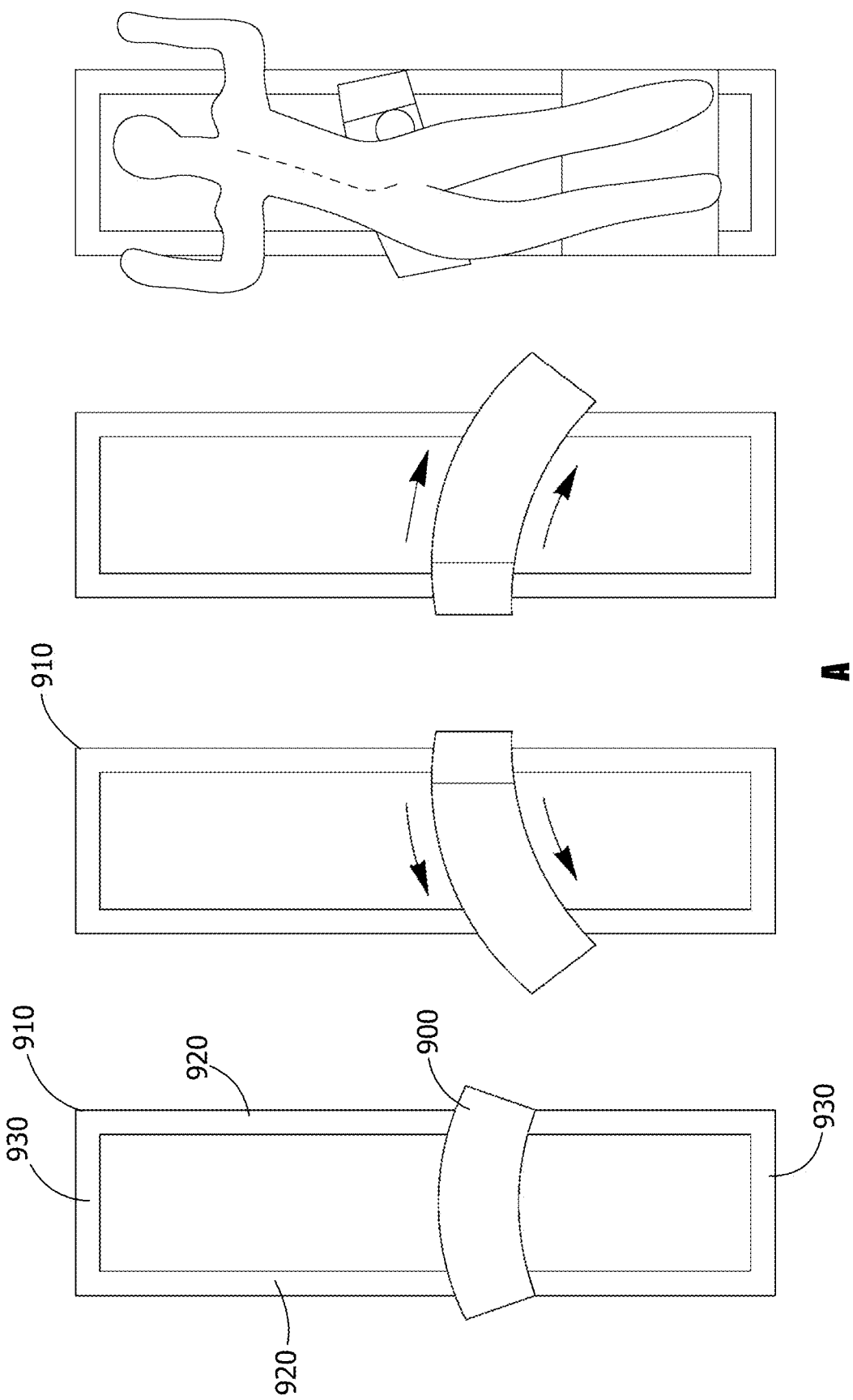
FIG. 33 includes in panel A top views of a surgical table according to the disclosure showing in successive frames a pivoting support in neutral and right pivot orientations and left pivot orientation with and without a prone subject, and in panel B top views as shown in panel A showing in successive frames the surgical table including conventional pads with and without a prone subject and with the support platform of the pivoting support removed, and in panel C an end view of the pivoting support showing opposing right and left bolsters and table frame tracks.
Figure 33:
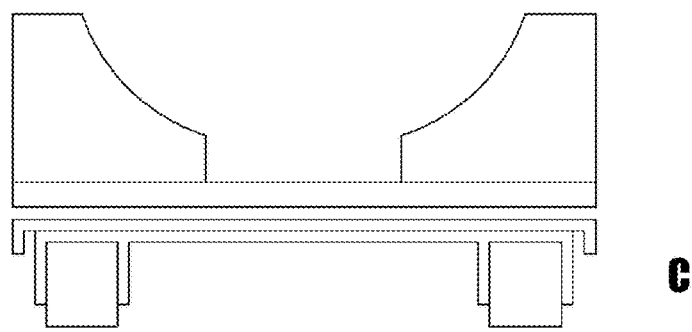
Figure 34:
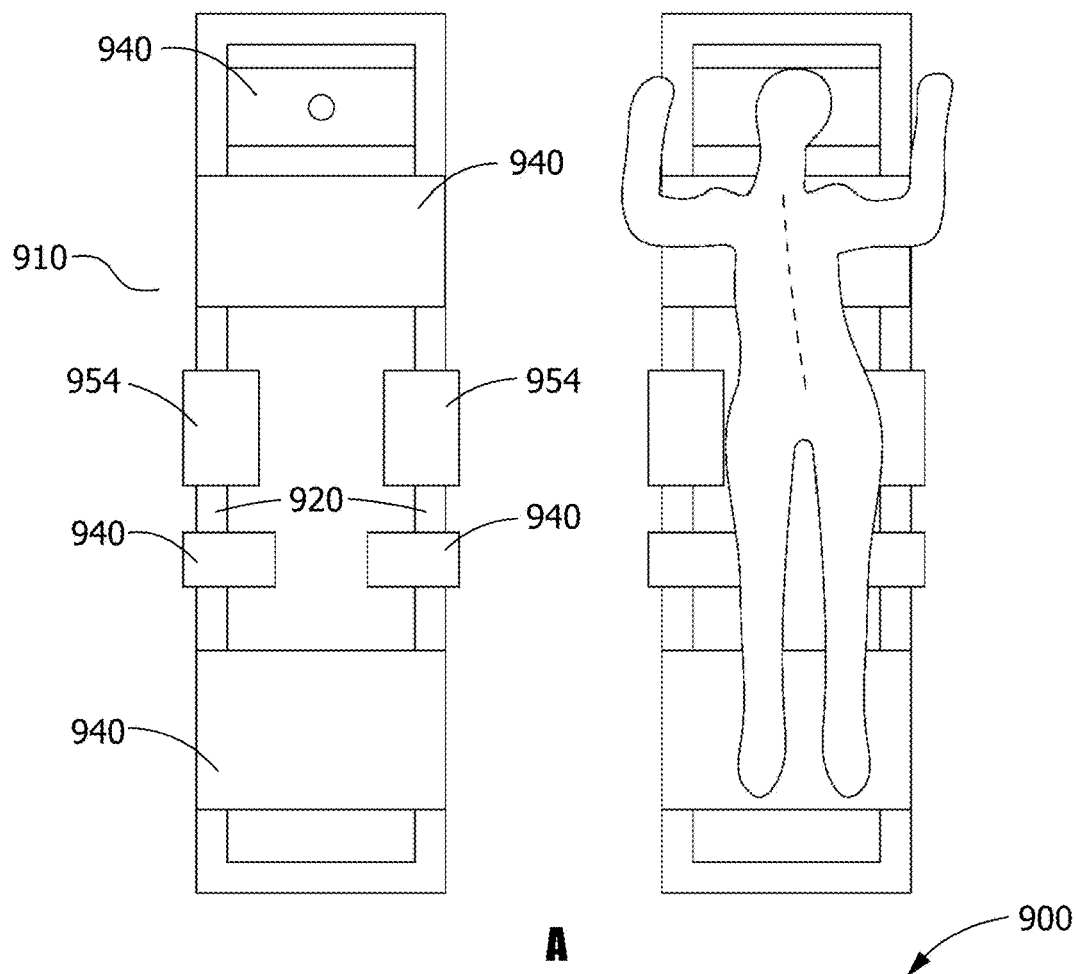
FIG. 34 includes in panel A top views of a conventional surgical table showing in successive frames conventional table pads with and without a prone subject, and in panel B an end view showing opposing right and left bolsters.
Figure 35:
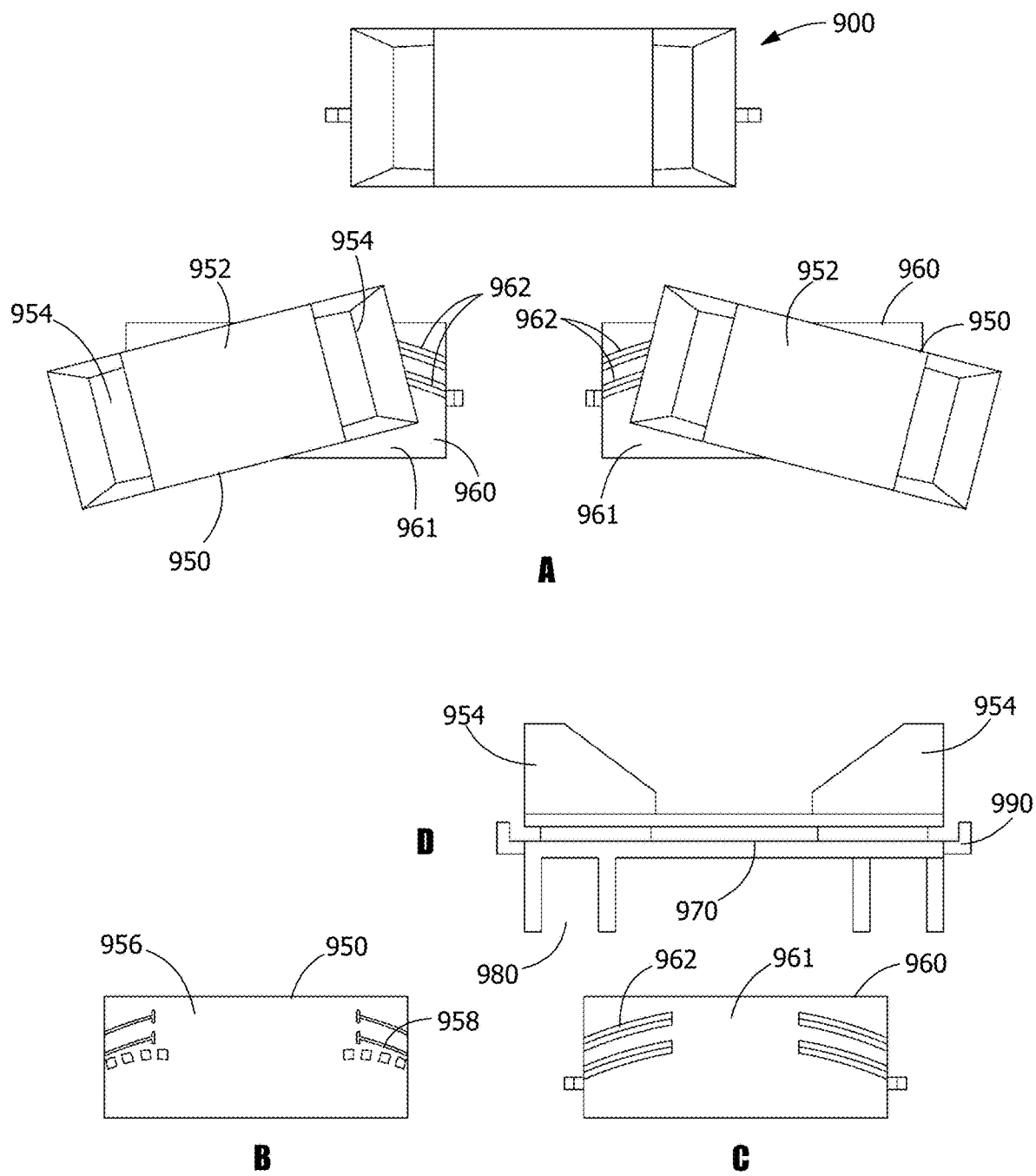
FIG. 35 includes in panel A top views of neutral, left and right pivot orientations of a pivoting support according to the disclosure, and in panel B a bottom view of the support platform of a pivoting support, and in panel C a top view of the pivot track of a pivot platform, and in panel D, alternate views of a crank/lock mechanism for actuating and locking the pivot position of a pivoting support.
Figure 36:
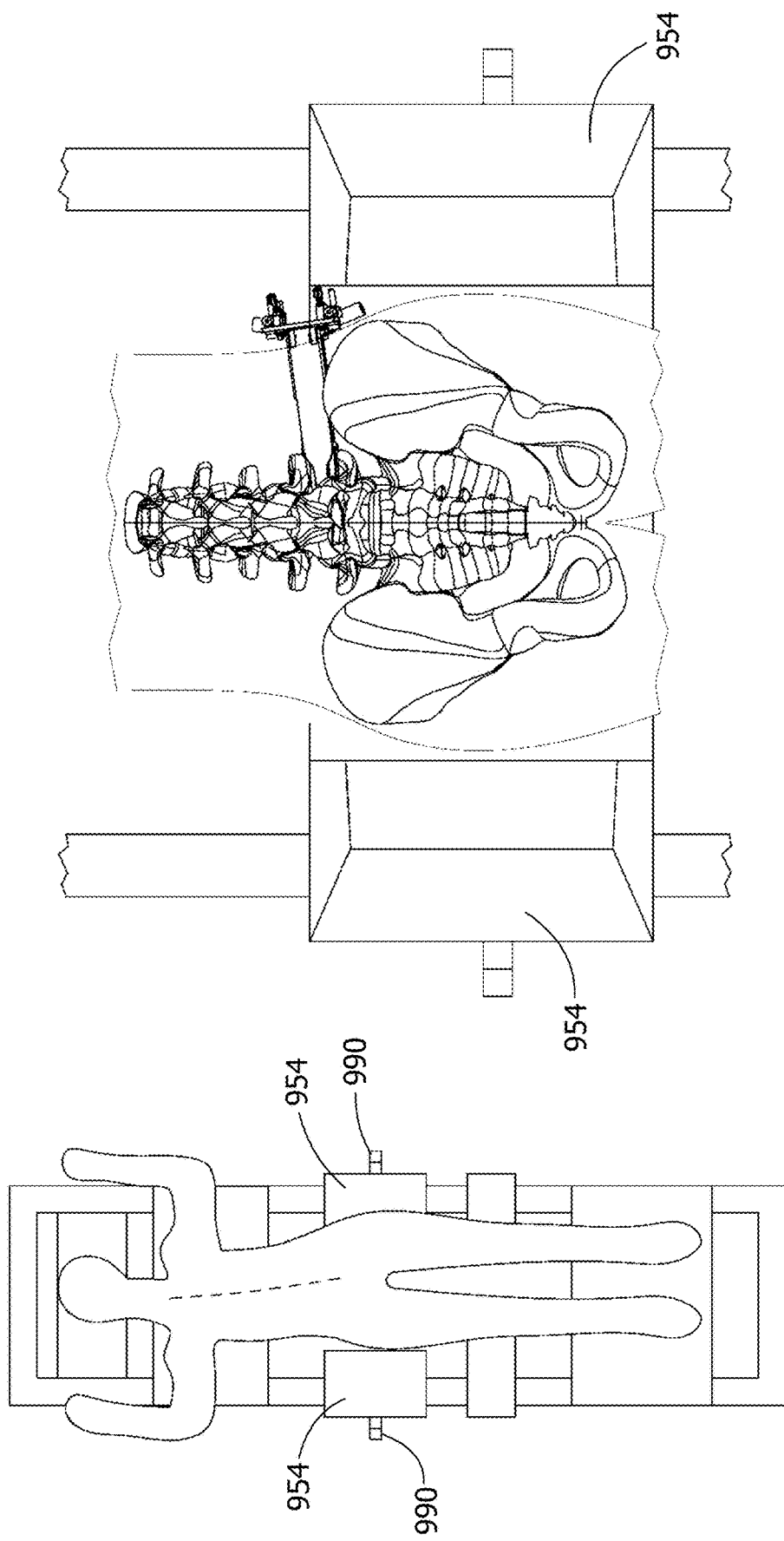
FIG. 36 includes in panel A a schematic showing an inferior to superior dorsal view of a portion of a lumbar spine in a neutral position featuring the relative position of the hip relative to the L4/L5 disc space, and in panel B a schematic showing an inferior to superior dorsal view of a portion of a lumbar spine in a left pivot position illustrating the relative shift of the hip to enhance exposure of the L4/L5 disc space.

Referring again to the drawings, pivoting support 900 devices shown in FIG. 33, FIG. 35 and FIG. 36 and described herein enable the adjustable positioning and support of a patient for example, in a prone position. A pivoting support 900 is provided that allows for lateral displacement from the spinal midline of a portion of the patient's spine, as illustrated in FIG. 33A. The pivoting support 900 can be placed, in a representative embodiment, at the hips of the patient and swung from to one or the other side to enhance access to a particular spinal region, such as for example L4/L5 vertebral joint. FIG. 34 shows top and end on views of a surgical table frame 910 with conventional body supports 940 which are components used for supporting one or more of the chest, thigh and head of a patient. FIG. 33B shows conventional support table components with a novel lumbar pivoting support 900 component that provides a lumbar access positioner system. The pivoting support 900 includes at least support and pivot platforms 950, 960 that are essentially planar, as shown in FIG. 35. Referring now to FIG. 35A, the support platform 950 includes on a first side an upper surface 952 for contact with the patient and may include cushioned material and optional positioning features, as described below. The support platform 950 includes on an opposite side of the cushion a lower surface 956 for engagement with the pivot platform 960, the lower surface 956 including engagement elements 958 to enable lateral motion when actuated. The engagement elements 958 are shown in FIG. 35B as curved rails in a parallel array that interface with corresponding arcuate tracks 962 on the pivot platform 960, as shown in FIG. 35C. It will be appreciated that other engagement features may be used to enable the relative pivotal motion between the two platforms 950, 960, and the disclosed means are not limiting.

In some embodiments, as shown in FIG. 35, the pivoting support 900 includes bolsters 954, either passively contact the patient to stabilize or elevate one or both sides of the hips. These supports 940, 900 may optionally be actively attached by gripping straps (not shown) to the patient to selectively secure a portion of the patient's anatomy such that when the pivoting support 900 is activated into motion, the degree of bend is enhanced thus enhancing the degree of exposure of the spinal region of interest. In accordance with such embodiments, the one or more pivoting supports 900 may include counter supports to secure the position of the patient's anatomy and prevent counter bending and reversion to a neutral spinal orientation. In alternate embodiments, features other than bolsters 954 may be used to stabilize and secure the patient's anatomy to the pivoting support 900, and the disclosed bolsters 954 are not intended to be limiting.

In some embodiments, the design preserves radiolucency under fluoroscopy when the table 910 is adjusted, and thus one or more of the supports 940, 900 or its components is radiolucent. In some embodiments the rollers and or rails 920, 930 supporting the supports 940, 900 are also formed of radiolucent material In various embodiments, the supports 940, 900 are attached in a secure manner to the table with engagement elements 980, for example with tracks for receiving table frame rails 920, 930, the tracks shown in FIG. 35D, and the pivoting supports 900 comprise actuators 990 for adjusting the lateral pivot angle. In some embodiments, the pivoting support 900 may also include positive locking elements to avoid inadvertent actuation and prevent injury to the operator or the patient. Further, in various embodiments, the support actuators 990 are lockable, and in some embodiments comprise positive locking elements to avoid inadvertent actuation. FIG. 35D (CONT) shows a possible locking actuator 990 that may be adapted for engagement with the pivot platform 960 or the support platform 950 to drive relative motion between them. The actuator 990 may be a pusher/puller with positive lock, or a rotary crank with a positive lock, and may further include a gauge that reflects the degree of rotation of the patient's anatomy from the neutral centerline of the table 910.

In use, the positioning apparatus is used to enable side-to-side rotation of a body part off the central axis of the table at a selected angle from a centerline and fixing that body part to the table frame in order to maintain position. In some embodiments, the body part positioned on the apparatus is the pelvis, and in some such embodiments, the tissue to be accessed is the spine. Referring now to FIG. 36A shows in the left frame a patient in prone and neutral (non-rotated) position, and in the right frame a close up anatomical depiction of the spine showing an assembled retractor according to the disclosure associated with the spine at the L4/L5 intervertebral space. It is evident from the drawing that the position of the patient's left hip relative to the inserted instrument interferes with and throws off the alignment therewith. Referring now to FIG. 36B, actuation of the pivot actuator 990 by swinging the support platform to the left causes the hip to rotate away from the spine, enhancing access to the vertebral space and enabling more desirable alignment of the distal end of the retractor assembly with the spine.

Thus, in various embodiments according to the disclosure, there is provided an apparatus for positioning a patient during surgery. In various embodiments, the apparatus may comprise modular adaptations to conventional surgical surfaces or tables, and in other embodiments may be a new surface or table. According to various embodiments, the apparatus comprises a pivoting support 900 mountable on a surgical table frame 910. Conventional table frames suitable for adaptation include, but are not limited to a surgical table frame 910 as shown in the drawings comprising two or more longitudinal rails 920 that are laterally spaced and two or more transverse rails 930, and one or more conventional modular body supports 940 selected from head, chest, abdomen, hip, thigh, and foot supports, which supports 940 are removably or permanently fixed on the frame 910 in a generally planar orientation, and which may be pivotally or otherwise adjusted to be above, below or transverse to the common plane. In other embodiments the table frame may have another configuration other than rods/rails and may also comprise more or fewer body supports.

According to the various embodiments of the disclosed apparatus, the pivoting support 900 comprises a support platform 950, a pivot platform 960, and surgical table engagement elements 980. According to such embodiments, the support platform 950 comprises on an upper surface 952 that may include a pad layer for providing cushioned support, two or more opposing bolsters 954 that are laterally spaced on the upper surface 952 relative to the pad, the bolsters 954 optionally comprising one or more straps for securing the body position between the laterally spaced bolsters 954 and comprising on a back surface 956 engagement elements 958 for engagement with the pivot platform 960. According to such embodiments, the pivot platform 960 comprises on an upper surface 961 a plurality of arcuate tracks 962 as engagement elements that are engageable with the engagement elements 958 on the back surface 956 of the support platform 950. And the pivot platform 960 includes on a back surface 970 adjustable and releasable surgical table engagement elements 980.

According to various embodiments, the pivoting support 900 enables positional adjustment of a portion of the body resting thereon by rotational movement of the support platform 950 along the path of the actuate tracks 962 of the pivot platform 960 to displace the supported body position in the direction of rotation. In various embodiments, the relative motion of the platforms 950, 960 is arcuate around a radius of curvature between 10 and 100 inches, including between 30 and 60 inches, and including a radius of about 42 inches. In various embodiments, the centerline of the arc is substantially parallel to the patient's spine and the longitudinal dimension of the table, and wherein the pivot platform 960 is rotated either left or right off the centerline wherein the extent of displacement from neutral position in each direction is between 10 degrees and 60 degrees, including between 20 and 40 degrees, and including 30 degrees.

According to various embodiments, the engagement elements 958 for engagement between the support platform 950 and the pivot platform 960 are selected from bearings, wheels and inter-fitting rails.

According to various embodiments, the pivoting support 900 comprises one or more of a pivoting actuator 990 for moving the support platform 950 relative to the pivot platform 960, the actuator 990 selected from a crank and a pusher/puller, a displacement guide for selecting the extent of displacement of the support platform from center along the arc, and a locking element for releasably locking the position of the displaced support platform.

According to various embodiments, the relative motion of the platforms 950, 960 is arcuate around a radius of curvature that is adjustably selectable and defined by a circle centered on the feet of the patient extending to the top of the pelvis/iliac crest.

In some specific embodiments, the pivot platform 900 is selected from an array of platforms each having plurality of arcuate tracks that correspond with a radius of curvature for a particular patient population, the array including at least one unique radius of curvature or ranges of radii of curvature, such as for example, small size having a radius range from 20-30 inches, medium size having a radius range from 30-40 inches, and large size having a radius range from 40-60 inches.

While the disclosed embodiments have been described and depicted in the drawings in the context of the human spine, it should be understood by one of ordinary skill that all or various aspects of the embodiments hereof may be used in in connection with other species and within any species on other parts of the body where deep access within the tissue is desirable.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

TABLE 1

| SCHEDULE OF FEATURES: | |
| --- | --- |
| Description | REF # |
| Modular surgical retractor | 10 |
| Retractor body | 20 |
| Proximal end | 21, 41 |
| Distal end | 22, 42 |
| Retractor body floor | 23 |
| Retractor body sidewalls | 24 |
| Chute | 25 |
| Bosses | 26 |
| Contoured distal end | 27, 47 |
| Tang Channel | 28 |
| Retractor body longitudinal axis | 29 |

TABLE 1-continued

| SCHEDULE OF FEATURES: | |
| --- | --- |
| Description | REF # |
| Retractor hood | 40 |
| Retractor hood body | 42 |
| Hood sidewalls | 44 |
| Retractor hood longitudinal axis | 45 |
| Lateral Slots | 46 |
| Soft tissue elevator | 47 |
| Releasable handle flange | 48 |
| Coupling element Tab Fastener | 52 |
| Coupling element Pin Fastener | 53 |
| Coupling element Receiver channel | 54 |
| Coupling element Receiver slot | 55 |
| Pivot axis | 56 |
| Yoke | 60 |
| Through channel | 64 |
| Central channel axis | 68 |
| Tissue fixation | 70 |
| A retractor securement element | 72 |
| Tissue securement element | 74 |
| Elongate Arm | 76 |
| Locking ring | 77 |
| Driver engageable with the guide | 78 |
| Tang | 86 |
| Tang grasping tab | 82 |
| Tang serrated blade | 84 |
| Slidable retractor blade | 90 |
| Compressed | 100 |
| Displaced vertically | 120 |
| Incision guidance instrument | 200 |
| Support base | 210 |
| Crosshair-oriented position indicators | 220 |
| A vertically adjustable depth indicator | 230 |
| Vertical extender with graduated markings | 234 |
| Linear pivot arm | 240 |
| Arcuate pointer | 245 |
| Support bracket adapter | 250 |
| Speculum shoehorn | 300 |
| Hand held retractor | 310 |
| Bilateral retractor | 320 |
| Hood handle | 330 |
| Shim | 340 |
| Awl | 360 |
| Tissue dilation system | 400 |
| Ribbon blade | 420 |
| First dilator | 430 |
| Second dilator | 440 |
| Tang awl | 460 |
| Tissue preparation device | 500 |
| Tissue engagement component | 510 |
| Tissue manipulator cutting instrument | 522 |
| Tissue manipulator pair of opposing curvilinear elongated blades | 530 |
| Collapsed orientation | 532 |
| A drive engagement component | 560 |
| Actuator strike plate engagement seat | 562 |
| Actuator rotating handle | 566 |
| Elongate curvilinear push rod | 570 |
| housing | 600 |
| Tissue engagement seat | 610 |
| Engagement teeth | 612 |
| Guide for directing the tissue manipulator | 614 |
| Threaded rod | 620 |
| Drive release button | 630 |
| Adjustable and releasable stabilization handle | 640 |
| A vertical shift component | 650 |
| Tissue manipulator attachment element | 700 |
| Universal joint | 710 |
| Extender frame | 720 |
| Distal and proximal attachment ends | 721, 722 |
| Blade receiving sidewalls | 724, 726 |
| A releasable tissue manipulator fastener | 730 |
| A length adjuster | 732 |
| Pivoting support | 900 |
| Surgical table frame | 910 |
| Longitudinal rails | 920 |
| Transverse rails | 930 |
| Modular body supports | 940 |

TABLE 1-continued

SCHEDULE OF FEATURES:

| Description | REF # |
| --- | --- |
| Support platform | 950 |
| Upper surface pad layer | 952 |
| Bolsters | 954 |
| Back surface, support platform | 956 |
| Engagement feature | 958 |
| Pivot platform | 960 |
| Upper surface pivot platform 960 | 961 |
| Plurality of arcuate tracks | 962 |
| Back surface pivot platform | 970 |
| Adjustable and releasable surgical table engagement elements | 980 |
| Actuator (eg, Crank) | 990 |

I claim:

1. An apparatus for positioning a patient during surgery, comprising:
 a surgical table frame having a longitudinal dimension, wherein the surgical table frame includes two or more longitudinal rails that are laterally spaced from a centerline between the longitudinal rails, the two or more laterally spaced longitudinal rails defining a generally planar surface of the surgical table frame; and
 at least one rotatable support mounted on the surgical table frame for supporting a portion of a body of the patient when resting thereon, the at least one rotatable support having a support surface that is substantially planar and generally parallel to the generally planar surface of the surgical table frame, the at least one rotatable support being rotatable around an axis that is perpendicular to the planar surface of the at least one rotatable support,
 wherein the at least one rotatable support includes two or more engagement elements, each of the two or more engagement elements engaging with the two or more longitudinal rails to mount the at least one rotatable support on the surgical table frame, the two or more engagement elements being in fixed arrangement relative to one another,
 wherein the at least one rotatable support enables positional adjustment of the portion of the body of the patient when resting thereon by rotational movement of the at least one rotatable support to displace the supported body position in one of first and second directions of rotation to thereby allow for manipulation of the patient's anatomy to maximize access to a surgical site of interest.

2. The apparatus for positioning a patient during surgery according to claim 1, comprising a plurality of rotatable supports.

3. The apparatus for positioning a patient during surgery according to claim 1, wherein the second direction of rotation is opposite to the first direction of rotation.

4. The apparatus for positioning a patient during surgery according to claim 1, comprising at least one bolster positioned on the at least one rotatable support at a lateral aspect relative to the centerline, the at least one bolster positioned for contacting and supporting a contacted lateral aspect of the portion of the body of the patient when resting on the at least one rotatable support.

5. The apparatus for positioning a patient during surgery according to claim 4, wherein the at least one rotatable support is positioned to support at least a hip region of the patient positioned thereon, and the at least one bolster is positioned to contact a lateral aspect of at least the hip region of the patient.

6. The apparatus for positioning a patient during surgery according to claim 1, comprising two or more modular body supports mounted on the surgical table frame, wherein the two or more modular body supports are configured on the surgical table frame to support at least one of head, abdomen, and feet, and wherein each of the two or more modular body supports may be rotatable or non-rotatable.

7. The apparatus for positioning a patient during surgery according to claim 6, wherein at least one of the two or more modular body supports is configured on the surgical table frame to support at least a hip region of the patient positioned thereon, and comprises at least one bolster positioned to contact a lateral aspect of the patient.

8. The apparatus for positioning a patient during surgery according to claim 1, comprising a pair of opposing bolsters on the at least one rotatable support, wherein the opposing bolsters are configured to one or both stabilize or elevate the supported portion of the body of the patient when resting on the at least one rotatable support.

9. The apparatus for positioning a patient during surgery according to claim 8, wherein the at least one rotatable support is positioned to support at least a hip region of the patient positioned thereon, and wherein the pair of bolsters are adapted to contact opposing lateral aspects of at least the hip region of the patient.

10. The apparatus for positioning a patient during surgery according to claim 1, wherein the at least one rotatable support includes one or more straps for securing the portion of the body of the patient when resting on the at least one rotatable support.

11. The apparatus for positioning a patient during surgery according to claim 1, wherein the two or more engagement elements are adjustable and releasable with respect to the longitudinal rails.

12. The apparatus for positioning a patient during surgery according to claim 1, wherein the at least one rotatable support comprises
 a. an actuator for moving the at least one rotatable support relative to the surgical table frame, the actuator selected from a crank and a pusher/puller;
 b. a locking element for releasably locking the position of the at least one rotatable support; or
 c. a combination thereof.

13. The apparatus for positioning a patient during surgery according to claim 1, wherein the apparatus is adapted for receiving a body of the patient positioned thereon in one of a prone and supine position.

14. The apparatus for positioning a patient during surgery according to claim 1, wherein the at least one rotatable support is rotatable at the centerline of the surgical table frame around an axis that is perpendicular to the planar surface of the at least one rotatable support.

15. An apparatus for positioning a patient during surgery, comprising:
 a surgical table frame having a longitudinal dimension, wherein the surgical table frame includes two or more longitudinal rails that are laterally spaced from a centerline between the longitudinal rails, the two or more laterally spaced longitudinal rails defining a generally planar surface of the surgical table frame;
 at least one rotatable support mounted on the surgical table frame for supporting a portion of a body of the patient when resting thereon, the at least one rotatable support having a support surface that is substantially planar and generally parallel to the generally planar surface of the surgical table frame, the at least one rotatable support being rotatable around an axis that is perpendicular to the planar surface of the at least one rotatable support;

a pair of opposing bolsters on the at least one rotatable support and opposing one another at a lateral aspect relative to the centerline, each of the pair of opposing bolsters positioned for contacting and one or both of stabilizing or elevating at least one contacted lateral aspect of the portion of the body of the patient when resting on the at least one rotatable support; and one or more straps for securing the portion of the body of the patient when resting on the at least one rotatable support wherein the apparatus is adapted for receiving a body of the patient positioned thereon in one of a prone and supine position, wherein the at least one rotatable support includes two or more engagement elements, each of the two or more engagement elements engaging with the two or more longitudinal rails to mount the at least one rotatable support on the surgical table frame, the two or more engagement elements being in fixed arrangement relative to one another, wherein the at least one rotatable support enables positional adjustment of the portion of the body of the patient when resting thereon by rotational movement of the at least one rotatable support to displace the supported body position in one of first and second directions of rotation to thereby allow for manipulation of the patient's anatomy to maximize access to a surgical site of interest.

16. The apparatus for positioning a patient during surgery according to claim 15, wherein the at least one rotatable support is positioned to support at least a hip region of the patient positioned thereon, and wherein the pair of bolsters are adapted to contact opposing lateral aspects of at least the hip region of the patient.

17. An apparatus for positioning a patient during surgery, comprising:
a surgical table frame having a longitudinal dimension, wherein the surgical table frame includes two or more longitudinal rails that are laterally spaced from a centerline between the longitudinal rails, the two or more laterally spaced longitudinal rails defining a generally planar surface of the surgical table frame;
at least one rotatable support mounted on the surgical table frame for supporting a portion of a body of the patient when resting thereon, the at least one rotatable support having a support surface that is substantially planar and generally parallel to the generally planar surface of the surgical table frame, the at least one rotatable support being rotatable relative to the surgical table frame to displace the supported body position in one of first and second directions of rotation to thereby allow for manipulation of the patient's anatomy to maximize access to a surgical site of interest;
at least one bolster positioned on the at least one rotatable support at a lateral aspect relative to the centerline, the at least one bolster positioned for contacting and one or both of stabilizing or elevating a contacted lateral aspect of the portion of the body of the patient when resting on the at least one rotatable support; and
one or more straps for securing the portion of the body of the patient when resting on the at least one rotatable support, wherein the at least one rotatable support includes two or more engagement elements, each of the two or more engagement elements engaging with the two or more longitudinal rails to mount the at least one rotatable support on the surgical table frame, the two or more engagement elements being in fixed arrangement relative to one another, wherein the apparatus is adapted for receiving a body of the patient positioned thereon in one of a prone and supine position.

18. The apparatus for positioning a patient during surgery according to claim 17, comprising a plurality of rotatable supports.

19. The apparatus for positioning a patient during surgery according to claim 17, wherein the second direction of rotation is opposite to the first direction of rotation.

20. The apparatus for positioning a patient during surgery according to claim 17, comprising two or more modular body supports mounted on the surgical table frame, wherein the two or more modular body supports are configured on the surgical table frame to support at least one of head, abdomen, and feet, and wherein each of the two or more modular body supports may be rotatable or non-rotatable.

21. The apparatus for positioning a patient during surgery according to claim 17, wherein the at least one rotatable support comprises a pad layer.

22. The apparatus for positioning a patient during surgery according to claim 17, wherein the at least one rotatable support is rotatable at the centerline of the surgical table frame around an axis that is perpendicular to the planar surface of the at least one rotatable support.

23. The apparatus for positioning a patient during surgery according to claim 17, comprising a pair of opposing bolsters on the at least one rotatable support and opposing one another at a lateral aspect relative to the centerline, each of the pair of opposing bolsters positioned for contacting and one or both of stabilizing or elevating at least one contacted lateral aspect of the portion of the body of the patient when resting on the at least one rotatable support.

24. The apparatus for positioning a patient during surgery according to claim 17, wherein the at least one rotatable support comprises
a. an actuator for moving the at least one rotatable support relative to the surgical table frame, the actuator selected from a crank and a pusher/puller;
b. a locking element for releasably locking the position of the at least one rotatable support; or
c. a combination thereof.

25. The apparatus for positioning a patient during surgery according to claim 17, wherein the at least one rotatable support is positioned to support at least a hip region of the patient positioned thereon, and the at least one bolster is positioned to contact a lateral aspect of at least the hip region of the patient.

26. An apparatus for positioning a patient during surgery, comprising:
a surgical table frame having a longitudinal dimension, wherein the surgical table frame includes two or more longitudinal rails that are laterally spaced from a centerline between the longitudinal rails, the two or more laterally spaced longitudinal rails defining a generally planar surface of the surgical table frame; and
at least one rotatable support mounted on the surgical table frame for supporting a portion of a body of the patient when resting thereon, the at least one rotatable support comprising a pair of opposing bolsters opposing one another at a lateral aspect relative to the centerline, each of the pair of opposing bolsters positioned for contacting and one or both of stabilizing or elevating, respectively, at least one contacted lateral aspect of the portion of the body of the patient when resting on the apparatus, the at least one rotatable support being rotatable around an axis that is perpendicular to the generally planar surface of the surgical table frame, the at least one rotatable support comprising two or more engagement elements, each one of the two or more engagement elements engaging respectively with each one of the two or more longitudinal rails to mount the at least one rotatable support on the surgical table frame, the two or more engagement elements being in fixed arrangement relative to one another, wherein the apparatus is adapted for receiving a body of the patient positioned thereon in one of a prone and supine position, wherein the at least one rotatable support enables positional adjustment of the portion of the body of the patient when resting thereon by rotational movement of the at least one rotatable support to displace the supported body position in one of first and second directions of rotation to thereby allow for manipulation of the patient's anatomy to maximize access to a surgical site of interest.

* * * * *